United States Patent
Bensen et al.

(10) Patent No.: US 7,410,800 B2
(45) Date of Patent: Aug. 12, 2008

(54) TRANSGENIC PLANTS WITH INCREASED GLYCINE-BETAINE

(75) Inventors: Robert Bensen, Niantic, CT (US); Paolo Castiglioni, Westerly, RI (US); John Korte, Westerly, RI (US); Erin Bell, Ladue, MO (US); Brendan Hinchey, Mystic, CT (US); Paul Loida, Kirkwood, MO (US); Jeffrey Ahrens, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 233 days.

(21) Appl. No.: 10/839,092

(22) Filed: May 5, 2004

(65) Prior Publication Data

US 2005/0160500 A1 Jul. 21, 2005

Related U.S. Application Data

(60) Provisional application No. 60/487,273, filed on Jul. 15, 2003, provisional application No. 60/467,910, filed on May 5, 2003.

(51) Int. Cl.
*A01H 5/00* (2006.01)
*A01H 5/10* (2006.01)
*C12N 15/82* (2006.01)

(52) U.S. Cl. .................. 435/468; 800/289; 800/298
(58) Field of Classification Search ......... 800/278–289; 435/320.1, 419, 468
See application file for complete search history.

(56) References Cited

OTHER PUBLICATIONS

Buell et al. (GenBank Accession No. AAP54879, pp. 1-2, Jun. 2003).*
Keskin et al. (Protein Science, 13:1043-1055, 2004).*
Thornton et al. (Nature structural Biology, structural genomics supplement, Nov. 2000).*
Nuccio et al. (Plant J., 16:487-496, 1998).*
EPO Communication EP04751446.8 - 2406 (PCT/US2004/014054) Supplementary European Search Report.
U.S. Appl. No. 11/520,715, filed Jan. 11, 2007, Jingdong Liu.
Appendix A (claims in U.S. Appl. No. 10/839,092 as allowed in the Notice of Allowance mailed Mar. 20, 2007), Petition for Withdrawal from Issue under 37 CFR §1.313(a) for U.S. Appl. No. 10/830,092, filed May 15, 2007.
Appendix B (claims pending in U.S. Appl. No. 11/520,715), Petition for Withdrawal from Issue under 37 CFR §1.313(a) for U.S. Appl. No. 10/839,092, filed May 15, 2007.
Appendix C (nucleic acid alignment between SEQ ID No. 19 of U.S. Appl. No. 10/839,092 and SEQ ID No. 25824 of U.S. Appl. No. 11/520,715), Petition for Withdrawal from Issue under 37 CRF §1.313(a) for U.S. Appl. No. 10/839,092, filed May 15, 2007.
Appendix D (amino acid alignment between SEQ ID No. 1 of U.S. Appl. No. 10/839,092 and SEQ ID No. 52139 of U.S. Appl. No. 10/839,092, filed May 15, 2007.

* cited by examiner

*Primary Examiner*—Ashwin Mehta
*Assistant Examiner*—Vinod Kumar
(74) *Attorney, Agent, or Firm*—Maria Margarita D. Unson; Thomas E. Kelley; Lawrence M. Lavin, Jr.

(57) ABSTRACT

Disclosed herein are transgenic plants and seed having an exogenous DNA which expresses a GB1 protein that imparts increased glycine-betaine content in plants.

14 Claims, 5 Drawing Sheets

Figure 1

```
Maize GB1      MIPYATAAEAEGALGRTMTWAETAWYEYSAVMPDSWLHCHTTFILFVIYS
Maize GB1-2    MMPYGTAAEAEAALGRSMTWAEALWFRYSAGMPDLCLTWHVSLVYLVLYA
Rice GB1-1     MLPYATAAEAEAAVGRGLTWAEAAWFRYSAAIPDYCLYCHNVPILLLVYT
Barley GB1-1   MLPYATTGDAEAALGRALTWAEAAWLRYSASVPDRYLHWPNIAITLVVYT
Consensus      MXPYXTXXXAEXAXGRXXTWAEXXWXXYSAXXPDXXL Maize GB1      IAPLPLLLLEQFAPSVVLPYKLQPRVRLPP--AASLSCYMDAACIFPLAV
Maize GB1-2    LVPLPVMVIQKLAPGYALRHKLQPGVPEPSPVSTYVEYIRDSRGVTLAAL
Rice GB1       LAPLPLALLELRR-HLPLPHKLQPGVRHPP--AAFLRCYAATARVLLLAV
Barley GB1     LAPLPLALFDLAAPAVAAPYKLQPKVQHPP--ATFFRCYMDAVRVSLLII Maize GB1      GLQFVSYPAVAKILRTRMGLPLPSVRETIAQLVVYSLVEDYLSYWMHRLL
Maize GB1-2    GPFPLIYSIAFKLFGVRTGLPLPSVWETATHLAVYSLVEDYTSYWLHRFL
Rice GB1       GPVQLASFPAVRAVGIRTGLPLPSAGETAAQVAVYLLVEDYLGYWIHRLL
Barley GB1     GPYQLISYPAAKIMDIRTGLPLPSMGEIAAQLTVYFLVEDYLNYWLHRLL Maize GB1      HTQWCYEKIHRVHHEFTAPTGFAMSYSHWAENVVLSIPALAGPVLVPCHV
Maize GB1-2    HTRWGYEKIHRVHHEKTAPSGFAAAYATGTELSLYLTTLFLGPAIVPSHV
Rice GB1       HTPWAYHHIHRVHHEFTAPMGYAAPYAHWAEILILGFPAFAGPAIVPCHM
Barley GB1     HTKWCYEKIHHVHHEFTAPMAYAAWYGHWAEMLILAXPSLAGPALVPCHV Maize GB1      TTQWLWFSIRLIEGINTHSGYHFPFSPCRLIPFYGGAAYHDYHHYAGGRS
Maize GB1-2    TTHWLLFSIRIMEAFDTHSGYHFPFSLARFIPFYGGAEFHDYHHYAGEKT
Rice GB1       TTFWLWFVLRHLEAIHIHSGFKLPFDPTKYIPLYGGVEYHDYHHFVGGHS
Barley GB1     TTLWIWFAARLVESLNIHSGFKLPFNAEKYIPFYGGAEHHDYHHYIGGQS Maize GB1      DYQSNFAPLFTYCLYRTDKGYRYHKLKQEKLKSLAENSADKGGNYSFDEG
Maize GB1-2    RSNFSSVFTYCDYIYGTNKGYMYHKRSLAELKTKEAEHSGKED-------
Rice GB1       QSNFSSVFTFCDYIYGTDRGYRYHKASLSKMRIFVRA-------------
Barley GB1     KSNFAPVFTYCDYIYGTDKGYRYHKATLAKLKELAGNEVQKGVDNGFNSG Maize GB1      KKNRYFCA
Maize GB1-2    --------
Rice GB1       --------
Barley GB1     KQE-----
```

Figure 2 (sheet 1)

```
     Maize GB1    MIPYATAAEAEGALGRTMTWAETAWYEYSAVMPDSWLHCHTTFIL
   Maize GB1-2    MMPYGTAAEAEAALGRSMTWAEALWFRYSAGMPDLCLTWHVSLVY
    Rice GB1-1    MLPYATAAEAEAAVGRGLTWAEAAWFRYSAAIPDYCLYCHNVPIL
  Barley GB1-1    MLPYATTGDAEAALGRALTWAEAAWLRYSASVPDRYLHWPNIAIT
  Maize GB1-3-1   MLPYATAAEAEAALGRPMTPAEALWFRYTAGVSDYHLYCCNILFL
   Leek GB1-3-1   MIPYPSLTAAEAALNRPLTYAETIWFNYSATIPDPLLYYHNTIFL
     At GB1-3-1   MIPYATVEEASIALGRNLTRLETLWFDYSATKSDYYLYCHNILFL
     At GB1-3-2   MIPYATIEEASIALSRNLTWLETLWFDYSATKSDYYLYCHNILFL
     At GB1-3-3   MIPYPTVEDASVALGRNLTWFETVWFDYSATKSNFHVYCHTILVL
     At GB1-3-4   MIPYATIEEASIALSRNLTWLETLWFDYSATKSDYYLYCHNILFL
     Bn GB1-3-1   MIPYATIEEASLALGRNLTTLETLWFDYSATKSDYYLYCHNILFL
    soy GB1-3-1   MLPYASIPEAVAALGRNLTFAETLWFNYSAAKSDYFLYCHNILFL
    soy GB1-3-2   MLPYHTLEGAQVALGRGLTLAETIWFKYSANKPDFVLHCHNTLFL
  barley GB1-3-1  MLPWATAAEAEAALGRPMTPAEALWFRWTAGTPDYGLYCLNILFL
    rice GB1-3-1  MLPYATAAEAEAALGRAMTAAESLWFRYSAGIPDYVLFWHNILFL
   wheat GB1-3-1  MLPWATAAEAEAALERAMTAAEALWFRWTAEASDYYLYCLNILFL
      Consensus   MXPXXXXXXXAXXAXXRXXTXXEXXWXXXXA Maize GB1    FVIYSIAPLPLLLLEQFAP--SVVLPYKLQPRVR--LPPAASLSC
   Maize GB1-2    LVLYALVPLPVMVIQKLAP--GYALRHKLQPGVPEPSPVSTYVEY
      Rice GB1    LLVYTLAPLPLALLELRR---HLPLPHKLQPGVR--HPPAAFLRC
    Barley GB1    LVVYTLAPLPLALFDLAAP--AVAAPYKLQPKVQ--HPPATFFRC
  Maize GB1-3-1   FVVFTVAPLPIALLELRAP--AAVSPYKLQPRVR--LSRAEFVRC
   Leek GB1-3-1   FVIFTLVPLPLALLELYWP--SVLKPFKIQPKVY--LSKSEFLEC
     At GB1-3-1   FLVFSLVPLPLVFVELARSASGLFNRYKIQPKVN--YSLSDMFKC
     At GB1-3-2   FLIFSLVPLPLVFIESSQSTSDLFNRYKIQPKVK--NSFSSMFKC
     At GB1-3-3   FLVFSLAPFPLVIVEWT----GWFDQFKIQKKVK--YSLSDMFQC
     At GB1-3-4   FLIFSLVPLPLVLIESAQSTSDLFNRYKIQPKVK--NSFSSMLKC
     Bn GB1-3-1   FLIFSLVPLPLVFVELARSASGWFDRYKIQPKVK--NSFSDMFRC
    soy GB1-3-1   FLVFSLVPLPLVFLEFKR--FSFVSSHKIQPKVR--LSLAETFKC
    soy GB1-3-2   CLFYSIAPIPFVLMELSG--YEKLNKHKIQPSVK--RSFKEMFKC
  barley GB1-3-1  LLVFTLAPLPVALLELRAP--RAVGPYKLQPRVR--LSRADFLKC
    rice GB1-3-1  FVVFTLAPLPVALLELRAP--AAVGPFKLQPKVR--LSREEFFRC
   wheat GB1-3-1  LVVFTLAPLPVALLELRAP--RAVGPYKLQPRVR--LSRAEFIKC Maize GB1    YMDAACIFPLAVGLQFVSYPAVAK----------ILRTRMGLPLP
   Maize GB1-2    IRDSRGVTLAALGPFPLIYSIAFK----------LFGVRTGLPLP
      Rice GB1    YAATARVLLLAVGPVQLASFPAVR----------AVGIRTGLPLP
    Barley GB1    YMDAVRVSLLIIGPYQLISYPAAK----------IMDIRTGLPLP
  Maize GB1-3-1   YKDVLRIFFLVIGPLQLVSYPAVK----------FVGIHTKLPLP
   Leek GB1-3-1   YKNVIKVFFLVVCPLQLLSYPTVK----------FVGIRTGLPLP
     At GB1-3-1   YKDVMTMFILVVGPLQLVSYPSIQ----------MIEIRSGLPLP
     At GB1-3-2   YKDVMKMFILVVGPLQLVSYPSIQVDFVFRVLKQMIEIRSGLPLP
     At GB1-3-3   YKEVMKLFLLVVGTLQIVSYPSIQ----------MVGIRSGLPLP
     At GB1-3-4   YKDVMKMFILVVGPLQLVSYPSIQ----------MIEIRSGLPLP
     Bn GB1-3-1   YRDVMKMFILVVGPLQLVSYPSIQ----------MIEIRSGLPLP
    soy GB1-3-1   YKDVMRMFFLVVGPLQLISYPSIQ----------MIGIRTGLPLP
    soy GB1-3-2   YKDVMETFVIAVSPLQIISYPTIK----------WIGIRTGLSLP
  barley GB1-3-1  YGDVMRIFFLVIGPLQLVSYPAVK----------MVGIHTGLPLP
    rice GB1-3-1  YRDVMRLFFLVIGPLQLVSYPTVK----------MVGIHTGLPLP
   wheat GB1-3-1  YGDVMRIFFLVIGPLQLVSYPAVK----------MVGIHTGLPLP
```

Figure 2 (sheet 2)

```
    Maize GB1   SVRETIAQLVVYSLVEDYLSYWMHRLLHTQWCYEKIHRVHHEFTA
  Maize GB1-2   SVWETATHLAVYSLVEDYTSYWLHRFLHTRWGYEKIHRVHHEKTA
     Rice GB1   SAGETAAQVAVYLLVEDYLGYWIHRLLHTPWAYHHIHRVHHEFTA
   Barley GB1   SMGEIAAQLTVYFLVEDYLNYWLHRLLHTKWCYEKIHHVHHEFTA
  Maize GB1-3-1 SLAELAAQLLVYFLVEDYLNYWIHRFLHGEWGYQNIHRVHHEFTA
   Leek GB1-3-1 SVWEVASQLAVYFLLEDFGNYWIHRWLHGKWGYEKIHKVHHEYTA
     At GB1-3-1 TITEMLSQLVVYFLIEDYTNYWVHRFFHSKWGYDKIHRVHHEYTA
     At GB1-3-2 SCMEIVAQLVVYFLVEDYTNYWVHRFFHCKWGYEKFHHIHHEYTA
     At GB1-3-3 SLMEIVAQLVVYFLIEDYTNYWIHRWMHCKWGYEKIHRIHHEYTS
     At GB1-3-4 SCMEIVAQFVVYFLVEDYTNYWVHRFFHCKWGYEKFHHIHHEYTA
     Bn GB1-3-1 SFGEIAAQLVVYFLVEDYTNYWVHRFFHSKWGYEKIHHIHHEYTA
    soy GB1-3-1 SWREILSQLLVYFLVEDYTNYWIHRFLHNDWGYEKIHRVHHEYHA
    soy GB1-3-2 SGWELFWQLFIYFVIEDFSNYWIHRMLHCKWAFEKIHKVHHEYVA
 barleyGB1-3-1  SLGEMAAQLVVYFLVEDYLNYWIHRLLHGEWGYEKIHRIHHEYTA
   rice GB1-3-1 SLGEMAAQLLVYFLVEDYLNYWIHRLLHGEWGYEKIHRVHHEFTA
  wheat GB1-3-1 SLGEMAAQLLVYFLVEDYLNYWIHRLLHGEWGYEKIHRIHHEYTA Maize GB1   PTGFAMSYSHWAENVVLSIPALAGPVLVPCHVTTQWLWFSIRLIE
  Maize GB1-2   PSGFAAAYATGTELSLYLTTLFLGPAIVPSHVTTHWLLFSIRIME
     Rice GB1   PMGYAAPYAHWAEILILGFPAFAGPAIVPCHMTTFWLWFVLRHLE
   Barley GB1   PMAYAAWYGHWAEMLILAXPSLAGPALVPCHVTTLWIWFAARLVE
  Maize GB1-3-1 PIGFAAPYAHWAEVLILGIPSFVGPAIVPGHMITFWLWIILRQVE
   Leek GB1-3-1 PIGFAAPYAHWAEVLILGIPSFLGPAIVPGHMITLWLWIALRQIE
     At GB1-3-1 PIGYAAPYAHWAEVLLLGIPTFMGPAIAPGHMITFWLWIALRQME
     At GB1-3-2 PIGYAAPYAHWAEVLLLGIPTFLGPAIAPGHMITFWLWIALRQIE
     At GB1-3-3 PIGYASPYAHWAEILILGIPTFLGPAIAPGHIMTFWLWISLRQFE
     At GB1-3-4 PIGYAAPYAHWAEVLLLGIPTFLGPAIAPGHMITFWLWIALRQIE
     Bn GB1-3-1 PIGYAAPYAHWAEVLLLGVPTFLGPAIAPGHMITFWLWIALRQIE
    soy GB1-3-1 PIGFAAPYAHWAEILILGIPSFLGPAMVPGHIITFWLWIALRQIE
    soy GB1-3-2 PIGLSAPYAHWAEIIILGIPXFLGPALVPGHITTYWLWFILRQLE
 barleyGB1-3-1  PIGFAAPYAHWAEVLILGIPSFAGPAIAPGHMITFWLWIILRQME
   rice GB1-3-1 PIGFAAPYAHWAEVLILGIPSFVGPALAPGHMITFWLWIVLRQME
  wheat GB1-3-1 PIGFAAPYAHWAEVLILGIPSFAGPAIAPGHMITFWLWIILRQME Maize GB1   GINTHSGYHFPFSPCRLIPFYGGAAYHDYHHYAGGRSQSNFAPLF
  Maize GB1-2   AFDTHSGYHFPFSLARFIPFYGGAEFHDYHHYAGEKTRSNFSSVF
     Rice GB1   AIHIHSGFKLPFDPTKYIPLYGGVEYHDYHHFVGGHSQSNFSSVF
   Barley GB1   SLNIHSGFKLPFNAEKYIPFYGGAEHHDYHHYIGGQSKSNFAPVF
  Maize GB1-3-1 AIETHSGFDFPFTPTKYIPFYGGAEYHDYHHYVGGQSQSNFASVF
   Leek GB1-3-1 ALDTHSGYDFPLSFTKFIPFYGGAEYHDYHHYVGGQSQSNFASVF
     At GB1-3-1 AIETHSGYDFPWSPTKYIPFYGGAEYHDYHHYVGGQSQSNFASVF
     At GB1-3-2 AIETHSGYDFPWSLTKYIPFYGGAEYHDYHHYVGGQSQSNFASVF
     At GB1-3-3 AIETHSGYDFPWSVTKLIPFYGGPEYHDYHHYVGGQSQSNFASVF
     At GB1-3-4 AIETHSGYDFPWSLTKYIPFYGGAEYHDYHHYVGGQSQSNFASVF
     Bn GB1-3-1 AIETHSGYDFPWTLTKFIPFYGGAEYHDYHHYVGGQSQSNFASVF
    soy GB1-3-1 AIDTHSGYDFPRSITKYIPFYGGAEYHDYHHYVGRQSQSNFASVF
    soy GB1-3-2 AIETHSGYDFSWEXTKYIPFYGGPAYHDYHHYVGGKSQSNFAS--
 barleyGB1-3-1  AIDTHSGFDFPFSLTKYIPFYGGAESHDYHHYVGGQSQSIFASVF
   rice GB1-3-1 AIETHSGFDFPFNLTKYIPFYGGAEYHDYHHYVGRQSQSNFASVF
  wheat GB1-3-1 AIDTHSGFDFPFSLTKYIPFYGGAEYHDYHHYVGGQSQSNFASVF
```

Figure 2 (sheet 3)

```
     Maize GB1      TYCDYLYRTDKGYRYHKLKQEKLKSLAENSADKGGNYSFDEGKKN
   Maize GB1-2      TYCDYIYGTNKGYMYHKRSLAELKTKEAEHSGKED----------
      Rice GB1      TFCDYIYGTDRGYRYHKASLSKMRIFVRA----------------
    Barley GB1      TYCDYIYGTDKGYRYHKATLAKLKELAGNEVQKGVDNGFNSGKQE
   Maize GB1-3-1    TYCDYLYGTDKGYRFHKTYLAKLKDLGHNDGQKGDGSGPSYVKLD
    Leek GB1-3-1    TYCDYVYGTDKGYRYRKACLSMMKEESENQNGVENSFQNQKSD--
      At GB1-3-1    TYCDYIYGTDKGYRFQKKLL-EQIKESS--KKSNKHNGGIKSD--
      At GB1-3-2    TYCDYIYGTDKGYRFQKKLLQQVNKYSIN----------------
      At GB1-3-3    TYCDYIYGTDKGYRIHKKLLHHQIKEEAEEKRVRKHD--------
      At GB1-3-4    TYCDYIYGTDKGYRFQKKLLQQMKEKSKKSNKLVNGGEKFD----
      Bn GB1-3-1    TYCDYIYGTDKGYRFQKKFLQQIKQESKKSN-MQNGGDKLD----
     soy GB1-3-1    TYCDYIYGTDKGYRYQKKILQKLKEELANGVEQNGGLYKTD----
     soy GB1-3-2    ---------------------------------------------
   barleyGB1-3-1    TYCDPLCGTDRGYRFHRASLPMLRALAPPAAKKDAPMGFSSAKGD
    rice GB1-3-1    TYCDYLYGTDKGYRYHKAYQAKMKALGQTEGEKADSNGLSYAKLD
   wheat GB1-3-1    TYCDYLYGTDRGYRFHKAYLAKLKDLAPSDGEKEGADGFAYAKLD Maize GB1      RYFCA
   Maize GB1-2      -----
      Rice GB1      -----
    Barley GB1      -----
   Maize GB1-3-1    -----
    Leek GB1-3-1    -----
      At GB1-3-1    -----
      At GB1-3-2    -----
      At GB1-3-3    -----
      At GB1-3-4    -----
      Bn GB1-3-1    -----
     soy GB1-3-1    -----
     soy GB1-3-2    -----
   barleyGB1-3-1    YVVL-
    rice GB1-3-1    -----
   wheat GB1-3-1    -----
```

TRANSGENIC PLANTS WITH INCREASED GLYCINE-BETAINE

REFERENCE TO RELATED APPLICATIONS

This application claims benefit under 35USC § 119(e) to U.S. Provisional Patent Applications Ser. No. 60/467,910, filed May 5, 2003 and Ser. No. 60/487,273, filed Jul. 15, 2003, each of which are incorporated herein by reference in their entirety.

INCORPORATION OF SEQUENCE LISTING

A sequence listing is contained in the file named "38-15 (52913)C Sequences.ST25.txt" which is 105 kilobytes (measured in MS-Windows 2000) and was created on Apr. 30, 2004 and is located in computer readable form on a 3.5 inch diskette filed herewith and incorporated herein by reference.

BACKGROUND OF THE INVENTION

Disclosed herein are polynucleotide sequences useful for producing transgenic plants with increased glycine-betaine content and methods of using such sequences for producing transgenic plants and seed. Such sequences are useful for producing transgenic plants with increased tolerance to stresses such as water-deficit and cold.

Stress, such as water-deficit, cold, heat, nutrient deficiency and the like, can have many adverse effects on plant performance such as yield reduction, increased susceptibility to disease and pests, reduced plant growth and reproductive failure. Considering the complexity of stress response in land plants, especially during conditions that produce water-deficit or cold, relatively few genes specifically associated with this aspect of physiology have been identified. It would be of benefit to the art to increase the number and variety of genes involved in regulating water use or temperature tolerance in plants, more particularly, in maize plants, and even more particularly in maize plants experiencing water-deficit and/or cold.

Glycine-betaine (N,N,N-trimethylglycine) is an osmoprotectant metabolite. Osmoprotectant metabolites, including betaines, such as glycine-betaine, sugars, sugar-alcohols, and amino acids, such as proline, are known to accumulate in plants under water-deficit and other stressful conditions such as cold conditions. Historically, applications of osmoprotectants to seeds and plants has been shown to have beneficial effects upon stress tolerance. Allard et al. (WO 99/01032) found that application of glycine-betaine to wheat plants increased the freezing tolerance of the plants by several degrees and Mottram (U.S. Pat. No. 5,952,267) disclose the foliar application of glycine-betaine to cotton plants under water-deficit which resulted in an increased number of cotton bolls.

The pathways for the synthesis of glycine-betaine are similar in higher plants and microorganisms. In both kingdoms, a two-step oxidation of choline occurs to produce glycine-betaine via an unstable glycine-betaine aldehyde intermediate. Choline is ubiquitous in higher plants. In spinach, the first step conversion of choline to glycine-betaine aldehyde utilizes a ferredoxin dependent choline monooxygenase. In *E. coli*, a membrane bound choline dehydrogenase performs this step. The second step, conversion of the unstable aldehyde to glycine-betaine, is carried out by glycine-betaine aldehyde dehydrogenase. This enzyme has been found to share strong similarity between plant and bacterial species.

Spinach, sugar beet and some varieties of maize are examples of higher plants in which glycine-betaine is found to accumulate under water-deficit stress. In contrast, many other plants, such as tomato, tobacco, rice and some varieties of maize, do not accumulate significant amounts of glycine-betaine, regardless of growing conditions.

Hanson et al., (U.S. Pat. No. 6,310,271) disclose tobacco transformed with a choline monooxygenase gene which exhibited increased accumulation of glycine-betaine. The transgenic plants also demonstrated increased tolerance to irrigation with saline solution when compared to non-transgenic controls. Bulow et al., (PCT Publication WO 98/26801) disclose the use of an *E. coli* choline dehydrogenase gene to impart increased freezing and choline tolerance in transformed potato plants. Allen et al., (U.S. application No. 2002/0123118A1) disclose the proposed use of choline oxidase, L-allo-threonine aldolase, phosphoserine phosphatase and sarcosine oxidase genes for altering the levels of glycine metabolism in a transformed cell. Adams et al., (U.S. Pat. No. 6,281,411; incorporated herein by reference in its entirety) disclose naturally occurring metabolites, such as glycine-betaine (Wyn-Jones and Storey, 1982) that are osmotically active and/or provide some direct protective effect during drought and/or desiccation.

We have discovered DNA useful for the production of a transgenic plant with increased glycine-betaine. As used herein "GB1" is the name of a protein and its homologs, e.g., a protein at least 40% identical to GB1, the expression of which results in increased glycine-betaine in plants and "gb1" is the name of the DNA coding sequence and its homologs encoding and used to express the GB1 protein. "GB" is used herein to refer to the glycine-betaine metabolite.

SUMMARY OF THE INVENTION

One aspect of this invention provides novel DNA constructs comprising DNA sequences which express GB1 proteins which, when expressed in a transgenic plant, can increase the glycine-betaine content of a transgenic plant. Certain plants expressing such DNA constructs for enhanced levels of glycine-betaine can exhibit increased tolerance to water-deficit, cold or freezing growing conditions or increased yield. The plants expressing the DNA constructs leading to increased glycine-betaine may be inbred or hybrid, preferably soybean, cotton, canola or maize.

In one aspect, the invention provides transgenic seed and plants having in the genome an exogenous DNA comprising a gb1 coding sequence having the sequence of SEQ ID NO:19 which expresses a GB1 protein having the amino acid sequence of SEQ ID NO:1 where the transgenic plants and seeds accumulate increased glycine-betaine as compared to plants and seed of substantially the same genotype lacking this exogenous DNA. In another aspect of the invention, the transgenic seed and plants accumulating increased glycine-betaine as a result of expressing an exogenous DNA comprising a gb1 coding sequence having the sequence of SEQ ID NO:19 which expresses a GB1 protein of SEQ ID NO:1, exhibit increased tolerance to water-deficit and to cold, and exhibit increased yield under normal growing conditions, water-deficit inducing conditions and cold conditions.

An important aspect of this invention provides transgenic seed and plants having in the genome an exogenous DNA comprising a gb1 coding sequence which expresses a protein having an amino acid sequence comprising at least 25 contiguous amino acids of the consensus amino acid sequence of SEQ ID NO:17 or SEQ ID NO:18. In yet another aspect of the invention such transgenic seed or plants have in the genome an exogenous DNA construct which expresses a GB1 protein having an amino acid sequence which is at least 40% identical SEQ ID NO:1. In another aspect, the invention provides transgenic seed and plants having in the genome an exogenous DNA comprising a gb1 coding sequence which has at least 98% identity to a nucleotide sequence in the group consisting of SEQ ID NOS:19-34, the sequences of which encode proteins having amino acid sequences of SEQ ID NOS:1-16, which result in increased accumulation of glycine-betaine in transgenic plants. The invention also provides transgenic seed and plants wherein the exogenous DNA comprising a gb1 DNA coding sequence is operably linked to a promoter which functions in plants. Operable promoters include constitutive, water-deficit-inducible, cold inducible, native, viral, tissue specific, or other promoters functional in a plant.

Still another aspect of this invention provides plants grown from such transgenic seed. The seed expressing exogenous DNA comprising gb1 coding sequence and GB1 protein leading to increased glycine-betaine may be inbred or hybrid, preferably soybean, cotton, canola or maize. Additionally, the invention provides for transgenic plants grown from the transgenic seed, for example, maize, cotton or soybean plants.

In another aspect, the invention provides for transgenic plants and seed comprising an exogenous DNA comprising a gb1 coding sequence which exhibit increased tolerance to cold temperatures. In one aspect, the transgenic plants and seed of the invention enable farmers to plant seed earlier and/or under cooler than normal temperatures for the seed type lacking the gb1 transgene, i.e., at a shorter relative maturity zone or a more polar latitude, increased germination under cold conditions, increased tolerance of newly germinated seed or young seedlings to cold, and increased tolerance of mature plants to cold allowing for later harvest and/or improved harvest, e.g. increased yield, under cold conditions, e.g., about ° C.-10° C. In another aspect, the invention provides transgenic plants and seed comprising an exogenous DNA comprising a gb1 coding sequence which exhibit increased germination, emergence and/or seedling survival at about 110 growing degree units (GDU) or less.

Additionally, the invention provides for a transgenic organism, e.g. a bacterium or plant, having in its genome an exogenous DNA construct which encodes a GB1 protein or homolog as define herein.

This invention also provides promoters for use in transgenic plants, e.g. a maize gb1 promoter and a coix hrgp promoter.

BRIEF DESCRIPTION OF THE DRAWINGS

FIG. 1 is an alignment of proteins of SEQ ID NOS:1-4 and a consensus sequence SEQ ID NO:17.

FIG. 2 is an alignment of proteins of SEQ ID NOS:1-16 and a consensus sequence SEQ ID NO:18.

DETAILED DESCRIPTION OF THE INVENTION

Sequences of the Invention

Figure 3:
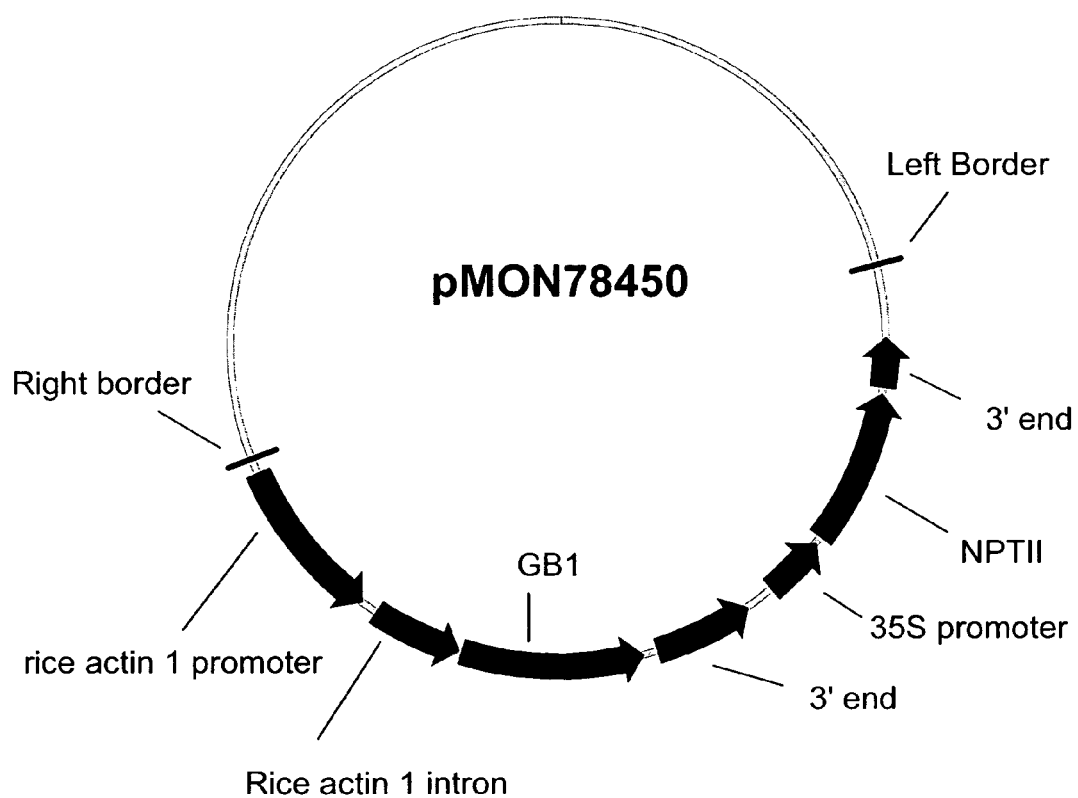
FIG. 3 is a plasmid map of pMON78450, the polynucleotide sequence from right border to left border is found in SEQ ID NO:57.

The following sequences are disclosed in the description of various aspects of this invention:

SEQ ID NO:1 is an amino acid sequence of a maize protein designated as GB1.

SEQ ID NO:2 is an amino acid sequence of a maize protein designated as maize GB1-2 homolog.

SEQ ID NO:3 is an amino acid sequence of a rice protein designated as rice GB1-1 homolog.

SEQ ID NO:4 is an amino acid sequence of a barley protein designated as barley GB1-1 homolog.

SEQ ID NO:5 is an amino acid sequence of a maize protein designated as maize GB1-3-1 homolog.

SEQ ID NO:6 is an amino acid sequence of a leek protein designated as leek GB1-3-1 homolog.

SEQ ID NO:7 is an amino acid sequence of an *Arabidopsis thaliana* protein designated as At GB1-3-1 homolog.

SEQ ID NO:8 is an amino acid sequence of an *Arabidopsis thaliana* protein designated as At GB1-3-2 homolog.

SEQ ID NO:9 is an amino acid sequence of an *Arabidopsis thaliana* protein designated as At GB1-3-3 homolog.

SEQ ID NO:10 is an amino acid sequence of an *Arabidopsis thaliana* protein designated as At GB1-3-4 homolog.

SEQ ID NO:11 is an amino acid sequence of a *Brassica napus* protein designated as Bn GB1-3-1 homolog.

SEQ ID NO:12 is an amino acid sequence of a soybean protein designated as soy GB1-3-1 homolog.

SEQ ID NO:13 is an amino acid sequence of a soybean protein designated as soy GB1-3-2 homolog.

SEQ ID NO:14 is an amino acid sequence of a barley protein designated as barley GB1-3-1 homolog.

SEQ ID NO:15 is an amino acid sequence of a rice protein designated as rice GB1-3-1 homolog.

SEQ ID NO:16 is an amino acid sequence of a wheat protein designated as wheat GB1-3-1 homolog.

SEQ ID NO:17 is a consensus amino acid sequence comprising amino acid residues of SEQ ID NOS:1-4.

SEQ ID NO:18 is a consensus amino acid sequence comprising amino acid residues of SEQ ID NOS:1-16.

SEQ ID NO:19 is a polynucleotide sequence of a maize gb1 coding sequence encoding the protein of SEQ ID NO:1.

SEQ ID NO:20 is a polynucleotide sequence of a maize gb1-2 homolog coding sequence encoding the protein of SEQ ID NO:2.

SEQ ID NO:21 is a polynucleotide sequence of a rice gb1-1 homolog coding sequence encoding the protein of SEQ ID NO:3.

SEQ ID NO:22 is a polynucleotide sequence of a barley gb1-1 homolog coding sequence encoding the protein of SEQ ID NO:4.

SEQ ID NO:23 is a polynucleotide sequence of a maize gb1-3-1 homolog coding sequence encoding the protein of SEQ ID NO:5.

SEQ ID NO:24 is a polynucleotide sequence of a leek gb1-3-1 homolog coding sequence encoding the protein of SEQ ID NO:6.

SEQ ID NO:25 is a polynucleotide sequence of an *Arabidopsis thaliana* gb1-3-1 homolog coding sequence encoding the protein of SEQ ID NO:7.

SEQ ID NO:26 is a polynucleotide sequence of an *Arabidopsis thaliana* gb1-3-2 homolog coding sequence encoding the protein of SEQ ID NO:8.

SEQ ID NO:27 is a polynucleotide sequence of an *Arabidopsis thaliana* gb1-3-3 homolog coding sequence encoding the protein of SEQ ID NO:9.

SEQ ID NO:28 is a polynucleotide sequence of an *Arabidopsis thaliana* gb1-3-4 homolog coding sequence encoding the protein of SEQ ID NO:10.

SEQ ID NO:29 is a polynucleotide sequence of a *Brassica napus* gb1-3-1 homolog coding sequence encoding the protein of SEQ ID NO:11.

SEQ ID NO:30 is a polynucleotide sequence of a soybean gb1-3-1 homolog coding sequence encoding the protein of SEQ ID NO:12.

SEQ ID NO:31 is a polynucleotide sequence of a soybean gb1-3-2 homolog coding sequence encoding the protein of SEQ ID NO:13.

SEQ ID NO:32 is a polynucleotide sequence of a barley gb1-3-1 homolog coding sequence encoding the protein of SEQ ID NO:14.

SEQ ID NO:33 is a polynucleotide sequence of a rice gb1-3-1 homolog coding sequence encoding the protein of SEQ ID NO:15.

SEQ ID NO:34 is a polynucleotide sequence of a wheat gb1-3-1 homolog coding sequence encoding the protein of SEQ ID NO:16.

SEQ ID NO:35 is a polynucleotide sequence of a rice actin 1 intron promoter.

SEQ ID NO:36 is a polynucleotide sequence of a maize hsp17.5 promoter.

SEQ ID NO:37 is a polynucleotide sequence of a maize hva22 promoter.

SEQ ID NO:38 is a polynucleotide sequence of a maize ca4h promoter.

SEQ ID NO:39 is a polynucleotide sequence of a maize rab-17 promoter.

SEQ ID NO:40 is a polynucleotide sequence of a maize rab-17 promoter.

SEQ ID NO:41 is a polynucleotide sequence of a rice hsp17.5 promoter.

SEQ ID NO:42 is a polynucleotide sequence of a rice hva22 promoter.

SEQ ID NO:43 is a polynucleotide sequence of a rice ca4h promoter.

SEQ ID NO:44 is a polynucleotide sequence of a rice hsp16.9 promoter.

SEQ ID NO:45 is a polynucleotide sequence of a rice hsp22 promoter.

SEQ ID NO:46 is a polynucleotide sequence of a rice rab-17 promoter.

SEQ ID NO:47 is a polynucleotide sequence of a maize gb1 promoter.

SEQ ID NO:48 is a polynucleotide sequence of a maize cvy-cik1 promoter.

SEQ ID NO:49 is a polynucleotide sequence of a maize cvy-cik1 promoter.

SEQ ID NO:50 is a polynucleotide sequence of a maize cvy-cik1 promoter.

SEQ ID NO:51 is a polynucleotide sequence of a maize cvy-cik1 promoter.

SEQ ID NO:52 is a polynucleotide sequence of a maize cvy-cik1 promoter.

SEQ ID NO:53 is a polynucleotide sequence of a rice cvy-cik1 promoter.

SEQ ID NO:54 is a polynucleotide sequence of a maize rtbv promoter.

SEQ ID NO:55 is a polynucleotide sequence of a maize nas promoter.

SEQ ID NO:56 is a polynucleotide sequence of a coix hrgp promoter.

SEQ ID NO:57 is a polynucleotide sequence from the right border to the left border, inclusive, of pMON78450 shown in FIG. 3. Base pairs 1 to 357 are the right border, base pairs 390 to 1232 are the rice actin 1 promoter, base pairs 1310 to 1778 are the rice actin 1 intron, base pairs 1781 to 2698 are the maize GB1 coding sequence of SEQ ID NO:19, base pairs 2767 to 3274 are the 3' untranslated region, base pairs 3409 to 3701 are the 35S promoter, base pairs 3766 to 4560 are the NPTII marker coding sequence, base pairs 4592 to 4844 are the nos 3' untranslated region, and base pairs 4924 to 5365 are the left border.

Traits of the Invention

A plant or seed that shows a desired trait, e.g., increased glycine-betaine, or increased tolerance or increased resistance to water-deficit condition, to cold condition, to freezing condition, or a plant with increased yield, is a plant or seed comprising a particular exogenous DNA which imparts a desired, measurable change in the trait in comparison to a control plant, e.g., a plant or seed of substantially the same genotype that lacks that particular exogenous DNA. Preferably, the enhanced desired trait is measured by comparing the trait in a transgenic plant or seed with the particular exogenous DNA associated with the enhanced desired trait to the trait in a control plant or seed. As used herein, a "control plant" or a "control seed" is a plant or seed of substantially the same genotype as the plant or seed it is being compared to, but lacking a particular exogenous DNA construct. A control plant or control seed can be a natural, non-transgenic wild-type plant preferably of the same species as the transgenic plant comprising the particular exogenous DNA. A control plant or control seed can be a second transgenic plant, preferably of the same species as the transgenic plant comprising the particular exogenous DNA, but lacking that same particular exogenous DNA. Preferably, the control plant or control seed lacking the exogenous DNA is a sibling of the plant or seed comprising the particular exogenous DNA, e.g. a negative segregant. Such a sibling control plant or control seed may comprise other exogenous DNA.

This invention provides for a transgenic maize plant exhibiting increased glycine-betaine content. The transgenic maize plant comprises an exogenous DNA comprising a gb1 coding sequence (SEQ ID NOS:19-34) expressing a GB1 protein (SEQ ID NOS:1-16) which exhibits at least about a 2-fold, about a 5-fold, about a 10-fold, about a 20-fold, about a 50-fold or even about a 70-fold or greater increase in glycine-betaine content as compared to a non-transgenic maize plant. Increased tolerance or resistance to water-deficit or cold or freezing may be exhibited by the plant accumulating at least a 2-fold increase in glycine-betaine and may be measured in a variety of ways including increased plant height, leaf length, leaf extension rate, number of leaves, root length, root mass, shoot mass, seed set, number of seed, yield, photosynthesis, turgor pressure, osmotic potential, amount of pollen, silking, germination, chlorophyll fluorescence, necrosis, and the like.

As used herein "stress response" is a plant or seed condition occurring in response to external influences capable of affecting the physical or biochemical characteristics of a plant or seed. These external influences are "stress." Stresses include, but are not limited to, all biotic and abiotic stresses that could influence a plant or seed, from infection to environment. For example, cold, heat, water-deficit, salinity, chemicals, weather conditions, fungal or bacterial infection, insect infestation, soil nutrient deficiencies or excesses, soil compaction or density, light, shade, or soil pH, or any combination of these conditions, are types of stresses a plant or seed may experience and respond to. Those physical or biochemical characteristics of a plant or seed that may be influenced by stress include, for example, yield, height, color, vigor, root growth, shoot growth, flowering times and qualities, seed quality, pollen quality, reproductive potential, germination or development, or any combination of these or other plant characteristics.

As used herein "water-deficit" is a plant condition characterized by water potential in a plant tissue of less than about −0.5 megapascals (MPa), e.g. −0.6 MPa. Water potential in maize is conveniently measured by clamping a leaf segment in a pressurizable container so that a cut cross section of leaf is open to atmospheric pressure. Gauge pressure (above atmospheric pressure) on the contained leaf section is increased until water begins to exude from the atmospheric-pressure-exposed cross section; the gauge pressure at incipient water exudation is reported as negative water potential in the plant tissue, e.g. 0.5 MPa gauge pressure is reported as −0.5 MPa water potential. A water-deficit may be induced in plant or seed by a number of manners, including growing in a geographical location in which rainfall is usually limiting, or growing in a growth chamber or greenhouse where water is provided or withheld in a monitored manner. In addition, water-deficit condition may be brought about in a plant or seed by exposure to solutions that may cause or mimic water-deficit such as saline solutions, PEG solutions and the like. A transgenic seed or plant is said to have improved water-deficit tolerance if it is able to germinate, germinate more quickly, grow, mature, and/or reproduce under water-deficit conditions as compared to a seed or plant of substantially the same genotype but lacking that exogenous DNA construct. A seed or plant with improved water-deficit tolerance would enable farmers to plant and grow crops in less than ideal water conditions, for example, in a drier location or in a location exposed with higher saline levels than normal in the soil and/or water used for irrigation, thus expanding the locations or conditions in which the plant or seed may be grown.

As used herein "non-water-deficit" conditions describe plant conditions characterized by water potential in a plant tissue of greater than about −0.5 megapascals (MPa), e.g. −0.4 MPa and may be measured as previously described. Non-water-deficit conditions may be induced in a plant by a number of manners, including growing plants in a geographical location in which rainfall is usually not limiting, growing plants in a geographical location in which rainfall is usually limiting and providing water by irrigation methods, or growing in a growth chamber or greenhouse where water is provided in a monitored manner.

As used herein "increased yield" identifies a measurable increase in the amount of useable product from a first plant, e.g., a plant comprising a particular exogenous DNA, compared to a second plant, e.g. a non-transgenic control plant or other control plant lacking a particular exogenous DNA, when the plants are grown under substantially identical conditions. Yield is based upon the weight of the grain produced from all the plants of a given line grown in a given plot and is measured in bushels per acre. Yield is typically measured in field trials using methods known to those of skill in the art.

As used herein, "cold tolerance" is defined as the ability of a seed, seedling, young plant, or mature plant, or parts thereof, to germinate and/or continue growth for a significant period of time after being placed at or exposed to a temperature below that normally encountered by a plant of that species at that growth stage. This invention provides a transgenic maize plant and seed with increased glycine-betaine comprising an exogenous DNA construct comprising a gb1 coding sequence (SEQ ID NOS:19-34) expressing a GB1 protein (SEQ ID NOS:1-16) that exhibits increased cold tolerance relative to a control plant or control seed.

"Germination" is defined as the beginning of growth or development in a seed, especially after a period of dormancy. Germination is often considered to begin when the seed takes up water (imbibes) and is considered to be essentially complete when the embryonic axis beings to elongate. As used herein, "cold germination" is germination occurring at temperatures below (two or more degrees Celsius below) those normal for a particular species or particular strain of plant. A transgenic seed is said to have improved cold germination if it is able to germinate more quickly in the cold temperature and/or if a greater percentage of the seed germinate in the cold temperature in a given amount of time as compared to a control seed or control plant. The temperature may be about 1° C. colder than normal, about 2° C. colder than normal, about 4° C., 6° C., 8° C. or even about 10° C. or more colder than normal.

A convenient way to measure cold stress conditions is to measure the accumulation of growing degree units (GDU) over time from the planting date. It is well known to one skilled in the art that approximately 120 GDUs are required for commercial maize hybrids to germinate and emerge from the soil. GDUs, which reflect the warming of the air, are measured on a daily basis in a cumulative manner using the following calculation:

$$GDU = \frac{(\text{Daily Max Temp}^* + \text{Daily Min Temp}^{**}) - 50}{2}$$

where * is the daily maximum temperature up to 86° F.; if the temperature exceeds 86° F. then the value of 86° F. is used and where ** is the daily minimum temperature down to 50° F.; if the temp is lower than 50° F. then the value of 50° F. is used.

Under cold conditions, therefore, it takes more days to reach a given number of GDUs and, conversely, under warm conditions it takes fewer days to reach that same number of GDUs. For example, the United States National Weather Service daily high and low normal temperatures for the last 30 years indicate that for Spencer, Iowa, (latitude 42.97, Longitude 90.10, a central location within the US maize growing territories) 20 days are required to accumulate 120 GDUs if planting occurs on April 15 whereas 11 days are required if planting occurs on May 15. Typically, it takes about 12 to about 15 days to accumulate the about 120 to 140 GDU required for maize to germinate in early spring conditions although one skilled in the art would know that this may vary slightly with respect to some variables such as planting depth and date of planting.

If it takes more than about 16, e.g., about 18, or 20 or even about 24 days, to accumulate about 120 to 140 GDUs, then a cold stress is imposed on a plant or seed. A transgenic seed having in its genome an exogenous DNA comprising a gb1 coding sequence, the expression of which results in increased glycine-betaine, will demonstrate improved germination and growth as compared to a control seed or control plant when about 16, or more, e.g. 18, 20 or 24 days are required to accumulate about 120 to 140 GDUs.

A transgenic maize seed having in its genome an exogenous DNA comprising a gb1 coding sequence resulting in increased glycine-betaine shows increased tolerance to cold conditions as compared to control plant or control seed. The transgenic maize seed germinates more quickly, emerges from the soil more rapidly and/or with more kernels germinated, and exhibits better seedling survival, in about 110 GDU, or less, e.g., 100 GDU or 90 GDU, than a control seed or control plant. It is known to one skilled in the art that hot and dry conditions during the reproductive phase damage the female organs and tissues, thereby reducing the harvested yield of commercial maize. The hot and dry conditions typically begin in early July within the US maize growing territories. A transgenic maize seed that emerges from the soil more quickly and/or with more kernels germinated and exhibits better seedling survival, in about 110 GDU or less, will reach reproductive developmental stages earlier in the growing season, thus avoiding damage during hot and dry conditions and thereby enabling farmers to effectively increase the harvested yield of maize in bushel/acre.

A seed or plant may be exposed to cold conditions at many points in time and thus it is desirable to have cold tolerance at many stages of development. For example, for a seed, cold germination is a form of cold tolerance that may be exhibited during germination at temperatures below the normal germination temperature for that seed. Cold tolerance may benefit a newly germinated seed as it may experience cold temperature after the embryonic axis begins to elongate. A young plant may benefit from cold tolerance as it may experience cold temperature as new leaves are developing above the ground. A more mature plant may benefit from cold tolerance as it may experience cold temperature during the periods of fertilization, seed set, grain fill and other reproductive activities. "Freezing tolerance" is defined as the ability of a seed, seedling, young plant, or mature plant, or parts thereof, to continue growth for a significant period of time after being placed at a temperature about freezing (e.g., about 32° F.) or below.

For a crop such as maize, a normal field planting is carried out when the temperature in the top two inches of soil is at least 10-12° C. during the day, therefore a transgenic seed that germinates more quickly and/or to a greater percentage at about 12° C., about 10° C., 8° C., 6° C., 4° C., or about 2° C. or even about 1° C. as compared to a seed or plant of substantially the same genotype but lacking that exogenous DNA construct, is considered to have improved or enhanced cold germination. A transgenic seed of the invention with enhanced cold tolerance, especially improved cold germination, would enable farmers to plant and grow crops at an earlier time in the season, in a cooler location than normal, at both an earlier time in the season and at a cooler location than normal, or allow for a later harvest, thus expanding the times and/or locations in which the plant may be grown as compared to control plants or control seed.

In a field, the cold temperatures may be imposed upon seeds and plants by planting at an earlier time than is normal for a particular location and/or planting at a geographical location that is typically colder than the geographical location in which the seed is normally planted, e.g., a shorter relative maturity (RM) zone. Relative maturity is a universal term of the art describing the time required for a given maize genotype to reach maturity. RM is determined during the development of a maize hybrid line by constantly assessing how many days the genotype takes to reach maturity in different environments. Most commercial hybrids fall into RM zones which range from 85 (in the more Northern areas of the US maize growing territories) to 125 (in the more Southern areas of the US maize growing territories). In other parts of the world growing maize, commercial hybrids typically have RMs of about 75-120 in Europe, about 108-138 in Africa, about 105-135 in Argentina, about 118-140 in Brazil, about 115-138 in Mexico and about 80-145 in Asia. Those skilled in the art know that maize varieties adapted to longer RM zones (100-120 or more) produce greater yield than those at shorter RM zones (85-100 or less); enabling farmers to grow a higher RM variety in a shorter RM zone would effectively increase the harvested yield of maize in bushel/acre worldwide. A transgenic seed or plant comprising an exogenous DNA comprising a gb1 DNA coding sequence of SEQ ID NOS:19-34 expressing proteins of SEQ ID NOS:1-16 exhibiting increased glycine-betaine and increased cold tolerance, would enable farmers to plant and grow crops in a shorter RM zone as compared to control seed or control plants.

Recombinant DNA Constructs

The present invention contemplates the use of polynucleotides which encode a protein effective for imparting increased tolerance to water-deficit or cold in plants, increased glycine-betaine, and/or increased yield. Such polynucleotides are assembled in recombinant DNA constructs using methods known to those of ordinary skill in the art. A useful technology for building DNA constructs and vectors for transformation is the GATEWAY™ cloning technology (available from Invitrogen Life Technologies, Carlsbad, Calif.) which uses the site-specific recombinase LR cloning reaction of the Integrase/att system from bacteriophage lambda for vector construction instead of restriction endonucleases and ligases. The LR cloning reaction is disclosed in U.S. Pat. Nos. 5,888,732 and 6,277,608, U.S. patent application Publications 2001283529, 2001282319 and 20020007051, all of which are incorporated herein by reference. The GATEWAY™ Cloning Technology Instruction Manual which is supplied by Invitrogen also provides concise directions for routine cloning of any desired RNA into a vector comprising operable plant expression elements.

As used herein "exogenous DNA" refers to DNA which is not normally found next to the adjacent DNA, i.e., a sequence not normally found in the host genome in an identical context, or any two sequences adjacent to each other which are not normally or naturally adjacent to each other. Exogenous DNA may include a DNA or RNA sequence native to the host genome or may comprise the native sequence altered by the addition or deletion of one or more different regulatory elements or other sequences as discussed below. The exogenous DNA may encode a protein or non-protein product. A DNA construct comprising a coding sequence of interest, which originates or is produced outside of an organism, is also an example of an exogenous DNA.

Exogenous DNA constructs used for transforming plant cells will comprise the coding sequence of interest and usually other elements as discussed below such as, but not limited to introns, 5' and 3' untranslated regions, and enhancers. An exogenous DNA of the present invention is exemplified by a rice actin 1 promoter and intron operably linked to a gb1 coding sequence operably linked to a 3' untranslated region. As used herein "transgene" means an exogenous DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the exogenous DNA.

As used herein "coding sequence" means a DNA sequence from which an RNA molecule is transcribed. The RNA may be an mRNA which encodes a protein product, an RNA which functions as an anti-sense molecule, or a structural RNA molecule such as a tRNA, rRNA, or snRNA, or other RNA. As used herein "expression" refers to the combination of intracellular processes, including transcription and translation, undergone by a DNA molecule to produce a protein or an RNA molecule. As used herein, a "gene" is a hereditary unit of DNA which comprises at least coding sequence; optionally included are other sequences such as introns, promoters, untranslated regions and other signal sequences.

As used herein "promoter" means a region of DNA sequence that is essential for the initiation of transcription of RNA from DNA; this region may also be referred to as a "5' regulatory region." Promoters are located upstream of DNA to be translated and have regions that act as binding sites for RNA polymerase and have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the site of initiation of transcription. The CAAT box element is usually located approximately 40 to 200 nucleotides upstream of the start site of transcription. The location of these basal promoter elements result in the synthesis of an RNA transcript comprising some number of nucleotides upstream of the translational ATG start site. The region of RNA upstream of the ATG is commonly referred to as a 5' untranslated region or 5' UTR. It is possible to use standard molecular biology techniques to make combinations of basal promoters, that is regions comprising sequences from the CAAT box to the translational start site, with other upstream promoter elements to enhance or otherwise alter promoter activity or specificity.

As is well known in the art, DNA constructs for use in transforming plants and expressing a coding sequence typically also comprise other regulatory elements in addition to a promoter, such as but not limited to 3' untranslated regions (such as polyadenylation sites), transit or signal peptides and marker coding sequences elements. For instance, see U.S. Pat. No. 6,437,217 which discloses a maize RS81 promoter. U.S. Pat. No. 5,641,876 which discloses a rice actin promoter, U.S. Pat. No. 6,426,446 which discloses a maize RS324 promoter. U.S. Pat. No. 6,429,362 which discloses a maize PR-1 promoter, U.S. Pat. No. 6,232,526 which discloses a maize A3 promoter, U.S. Pat. No. 6,177,611 which disdoses constitutive maize promoters, U.S. Pat. Nos. 5,322,938, 5,352,605, 5,359,142 and 5,530,196 which disclose a 35S promoter, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,294,714 which discloses light inducible promoters, U.S. Pat. No. 6,140,078 which discloses salt inducible promoters, U.S. Pat. No. 6,252, 138 which discloses pathogen inducible promoters, U.S. Pat. 6,175,060 which discloses phosphorus deficiency inducible promoters, U.S. Pat. No. 6,635,806 which discloses a coixin promoter, and U.S. patent application publication 2004/0216189 A1 which discloses a maize chloroplast aldolase promoter, all of which are incorporated herein by reference. One skilled in the art would know that various introns, enhancers, transit peptides, targeting signal sequences, 5' and 3' untranslated regions (UTRs) useful in the design of effective plant expression vectors, such as those disclosed, for example, in U.S. patent application Publication 2003/01403641 (incorporated herein by reference), may be used in the promoter and coding sequence combination clones, such as, for example, those described in Table 2, to obtain and optimize expression of the gb1 coding sequence (SEQ ID NO:19) and homologs (SEQ ID NOS:20-34) of the invention.

In some aspects of the invention it is preferred that the promoter element in the exogenous DNA construct should be capable of causing sufficient expression of SEQ ID NOS:19-34 to result in the production of an effective amount of the proteins of SEQ ID NOS:1-16 only under water-deficit conditions, cold conditions or other stress situations. By avoiding continuous high-level expression of transgenes, any undesired effects caused by continual over-expression of transgenes, or ectopic expression in various tissues or at various times, can be minimized or eliminated. Such promoters can be identified and isolated from the regulatory region of plant genes which are up-regulated in water-deficit conditions, cold or other stress conditions.

Specific water-deficit-inducible promoters for the expression of a maize gb1 coding sequence (SEQ ID NO:19) and homologs of a maize gb1 coding sequence (SEQ ID NOS:20-34) useful in the practice of this invention are derived from the 5' regulatory region of genes identified as a heat shock protein 17.5 gene (hsp17.5; SEQ ID NO:36), an HVA22 gene (hva22; SEQ ID NO:37), and a cinnamic acid 4-hydroxylase gene (ca4h; SEQ ID NO:38) of *Zea mays*. Such water-deficit-inducible promoters are disclosed in U.S. application Ser. No. 10/739,565, incorporated herein by reference. Additional specific water-deficit-inducible promoters useful in the practice of this invention are derived from the 5' regulatory region of genes identified as a heat shock protein 17.5 gene (hsp17.5; SEQ ID NO:41), an HVA22 gene (hva22; SEQ ID NO:42), a cinnamic acid 4-hydroxylase gene (ca4h; SEQ ID NO:43), an HSP16.9 gene (hsp16.9; SEQ ID NO:44), an HSP22 gene (hsp22; SEQ ID NO:45), and a rab-17 promoter (SEQ ID NO:47) of rice. Such water-deficit-inducible promoters are disclosed in U.S. provisional application Ser. No. 60/547761, incorporated herein by reference. Additionally preferred water-deficit inducible promoters contemplated to be particularly useful in the practice of this invention include the rab-17 promoter reported by Vilardell et al., (*Plant Molecular Biology*, 17(5):985-993, 1990; SEQ ID NO:39) as well as a second, independently isolated rab-17 promoter (SEQ ID NO:40; disclosed in U.S. application Ser. No. 10/739,565).

It is also contemplated that a cold inducible promoter is a useful promoter for the expression of a maize gb1 coding sequence (SEQ ID NO:19) and homologs of a maize gb1 coding sequence (SEQ ID NOS:20-34). Cold inducible promoters have been isolated from a variety of plants and useful promoters include, for example, a wcs120 promoter from wheat (Oullet, F. et al., *FEBS Letters*. 423: 324-328, 1998), a ci7 promoter from potato (Kirch, H. et al., *Plant Mol Biol.*, March;33(5):897-909, 1997), an hva22 coding sequence from barley (Shen, Q., et al., *Plant Mol Biol.*, February;45(3): 327-40, 2001), a cor15 promoter from *Arabidopsis* (Baker, S. et al., *Plant Mol Biol*. March;24(5):701-13, 1994), a kin1 or cor6.6 cold inducible promoter also from *Arabidopsis* (Wang H., et al., *Plant Mol Biol*. July;28(4):605-17, 1995) or the cold inducible promoters described in U.S. Pat. No. 6,084,089. A preferred cold inducible promoter is the maize cvy-cik1 promoter (SEQ ID NOS:48-52) or its rice homolog (SEQ ID NO:53). The cvy-cik1 promoter is induced in transgenic maize plants following cold treatment and is disclosed in U.S. provisional application Ser. No. 60/463,974, incorporated herein by reference in its entirety.

A useful promoter for expression a maize gb1 coding sequence is a promoter isolated from a maize gb1 gene (SEQ ID NO:47).

Tissue-specific promoters are also contemplated to be useful promoters for driving the expression of maize gb1 coding sequences and homologous sequences (SEQ ID NOS:19-34). Such promoters include, but are not limited to, a phloem specific rice tungro baciliform virus promoter (RTBV; SEQ ID NO:54 and U.S. Pat. No. 5,824,857), a maize root specific nicotianamine synthase promoter (SEQ ID NO:55), or a silk specific hydroxyproline rich glycoprotein promoter (hrgp; SEQ ID NOS:56).

During transformation, exogenous DNA may be introduced randomly, i.e. at a non-specific location, in the plant genome. In some cases, it may be useful to target an exogenous DNA insertion in order to achieve site-specific integration, e.g. to replace an existing gene sequence or region in the genome. In some other cases it may be useful to target an exogenous DNA integration into the genome at a predetermined site from which it is known that gene expression occurs. Several site-specific recombination systems exist which are known to function in plants include Cre/lox as disclosed in U.S. Pat. No. 4,959,317 and FLP/FRT as disclosed in U.S. Pat. No. 5,527,695, both incorporated herein by reference.

Constructs and vectors may also include a transit peptide for targeting of a protein or RNA product to a plant organelle, particularly to a chloroplast, leucoplast or other plastid organelle. For a description of the use of a chloroplast transit peptide see U.S. Pat. No. 5,188,642, incorporated herein by reference.

In practice DNA is introduced into only a small percentage of target cells in any one experiment. Marker genes are used to provide an efficient system for identification of those cells that are stably transformed by receiving and integrating an exogenous DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring coding sequence has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS; CP4). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Protein Molecules

Proteins of the present invention which represent whole proteins or at least a sufficient portion of the entire protein to impart the relevant biological activity of the protein, e.g. increased glycine-betaine content in a transgenic organism. The term "protein" also includes molecules consisting of one or more polypeptide chains. Thus, a protein useful in the present invention may constitute an entire gene product or one or more functional portions of a natural protein which provides the agronomic trait of this invention, i.e. increased glycine-betaine, increased yield despite exposure to water-deficit, increased yield despite exposure to cold, increased yield under non-water-deficit conditions or increased yield under normal growing temperatures.

Homologs of the proteins of the present invention may be identified by comparison of the amino acid sequence of the GB1 protein of SEQ ID NO:1 to amino acid sequences of proteins from the same or different plant sources, e.g. manually or by using known homology-based search algorithms such as those commonly known and referred to as BLAST, FASTA, and Smith-Waterman.

A further aspect of the invention provides coding sequences which encode functional homologous proteins which differ in one or more amino acids from those of a GB1 protein provided herein as the result of one or more of the well-known conservative amino acid substitutions, e.g. valine is a conservative substitute for alanine and threonine is a conservative substitute for serine. When such a homologous protein is expressed in a transgenic plant, the homologous protein will affect the transgenic plant in a substantially equivalent manner as the GB1 protein.

Conservative substitutions for an amino acid within the native protein sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine.

A further aspect of the invention comprises proteins which differ in one or more amino acids from those of a described GB1 protein sequence as the result of deletion or insertion of one or more amino acids in a native sequence. When such a homologous protein is expressed in a transgenic plant, the homologous protein will affect the transgenic plant in a substantially equivalent manner as the GB1 protein, e.g., result in increased glycine-betaine content.

Proteins of the present invention that are variants of the proteins provided herein will generally demonstrate significant identity with the proteins provided herein. Of particular interest are proteins having at least 50% sequence identity, more preferably at least about 70% sequence identity or higher, e.g. at least about 80% sequence identity with a consensus amino acid sequence of SEQ ID NO:17 or SEQ ID NO:18. Of course useful proteins also include those with higher identity to a consensus sequence, e.g. 90%, to 100% identity. Other proteins of interest have at least 50% or more, e.g. at least 60% or 70% of homology with the proteins as defined by SEQ ID NO:1 through SEQ ID NO:16. Of course useful proteins also include those with higher percentage homology with the amino acids in a protein segment of SEQ ID NO:1 through SEQ ID NO:16, e.g., 80%, 90%, 95%, 98% or up to 100% homology.

Transformation Methods and Transgenic Plants

Methods and compositions for transforming plants by introducing an exogenous DNA into a plant genome in the practice of this invention can include any of the well-known and demonstrated methods. Preferred methods of plant transformation are microprojectile bombardment as illustrated in U.S. Pat. Nos. 5,015,580; 5,550,318; 5,538,880; 6,160,208; 6,399,861 and 6,403,865 and *Agrobacterium*-mediated transformation as illustrated in U.S. Pat. Nos. 5,635,055; 5,824, 877; 5,591,616; 5,981,840 and 6,384,301, all of which are incorporated herein by reference.

Transformation methods of this invention to provide plants with increased water-deficit, cold or other stress tolerance are preferably practiced in tissue culture on media and in a controlled environment. "Media" refers to the numerous liquid, solid, or semi-solid nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. "Propagation" or "propagating" as used herein means the process of multiplying or breeding plant material. Therefore, propagation may involve maintaining a viable tissue on a media, e.g. a callus tissue on a solid medium, or growing a plant from seed or tissue, such as callus and cuttings.

As used herein "regeneration" means the process of growing a plant from a plant cell (e.g., plant protoplast, callus or explant). It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. No. 6,194,636 and U.S. patent application Ser. No. 09/757,089, both of which are incorporated herein by reference.

As used herein a "transgenic" organism is one whose genome has been altered by the incorporation of foreign genetic material or additional copies of native genetic material, e.g. by transformation or recombination. The transgenic organism may be a plant, mammal, fungus, bacterium or virus. As used herein "transgenic plant" means a plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences which are native to the plant being transformed, but wherein the exogenous DNA has been altered in order to alter the level or pattern of expression of the coding sequence.

As used herein an "$R_o$ transgenic plant" is a plant which has been directly transformed with an exogenous DNA or has been regenerated from a cell or cell cluster which has been transformed with an exogenous DNA. As used herein "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back crossed. Thus, a transgenic maize plant prepared according to the invention may be an Ro plant, and progeny plants may be inbred or hybrid maize plants and may be heterozygous or homozygous for the exogenous DNA insertion. As used herein "crop plants" of interest include, but are not limited to soy, cotton, canola, wheat, sunflower, sorghum, alfalfa, barley, millet, rice, tobacco, fruit and vegetable crops, and turf grass. A preferred crop plant is Zea mays, commonly known as maize or corn.

The seeds of this invention are harvested from fertile transgenic plants and used to grow progeny generations of plants of this invention including a hybrid plant line comprising the exogenous DNA encoding proteins of SEQ ID NOS:1-16 which provides the benefits of increased resistance and/or tolerance to stresses such as, but not limited to, water-deficit or cold and increase yield. The seeds of the invention also comprise increased glycine-betaine content as compared to a non-transgenic seed.

EXAMPLES

Having now generally described the invention, the same will be more readily understood through reference to the following examples which are provided by way of illustration, and are not intended to be limiting of the present invention, unless specified.

Example 1

Identification of a gb1 Gene from Zea mays

Plants from a number of non-transgenic inbred lines of Zea mays were field-grown under water-deficit (non-irrigated) or non-water-deficit (irrigated) conditions. Leaf samples were taken from plants before the tassel stage for each condition, and RNA and metabolites were isolated. RNA from the water-deficit and non-water-deficit samples was analyzed for differences using transcriptional profiling array methods. A number of RNAs were found to show differences in accumulation, to either higher or lower levels in the plants, depending upon the water treatment.

In addition to RNA transcription profiling, the glycine-betaine (GB) content was determined in leaf tissue samples from the inbred lines grown under water-deficit and non-water-deficit conditions. The characterized inbred maize lines were grouped into two categories: "GB accumulators," comprising greater than about 0.05 mM GB, and "GB non-accumulators," comprising less than about 0.05 mM GB.

One particular transcriptional profiling array element demonstrated an increase in RNA accumulation under water-deficit conditions compared to non-water-deficit conditions. In addition, under water-deficit conditions, plants in the study designated as "GB accumulators" were shown to have 3 to 12-fold higher levels of RNA transcript of this array element when compared to "GB non-accumulator" maize plants. These correlations were significant at the $p<0.005$ level across more than 85 commercial inbred lines of Zea mays. This array element was designated as the GB1 array element.

The GB1 array element was used as a probe in a Northern blot analysis using RNA samples from GB accumulator maize plants which were grown under both water-deficit and non-water-deficit conditions. The Northern blot analysis showed that the GB1 array element probe hybridized to a single RNA species which accumulated to much higher levels in water-deficit plants as compared to non-water-deficit plants. In contrast, when the GB1 array element was used as a probe against RNA samples from water-deficit and non-water-deficit plant tissues from GB non-accumulator lines, no hybridization was observed.

Sequence of the GB1 array element was used to identify a full-length sequence, designated the gb1 DNA, in a proprietary database of maize DNA sequences. Translation of the full-length gb1 DNA sequence (SEQ ID NO:19) indicated that the GB1 peptide sequence (SEQ ID NO:1) shares limited homology with particular histidine domains found in a sterol -4α-methyl oxidase cDNA from *Arabidopsis thaliana* (Darnet et al., 2001) and a C-4 methyl sterol oxidase from *Saccharomyces cerevisiae* (Bard et al., 1996). In these systems, however, these enzymes are thought to be involved in sterol metabolism and no role has been identified for the participation of these enzymes in the synthesis of glycine-betaine. Rafalski and Famodu (U.S. Pat. No. 6,479,733) propose the use of C-4 methyl sterol oxidase in the manipulation of sterol metabolism in a plant; the sequence of the present invention and that of Rafalski and Famodu are only distantly related at the polynucleotide and amino acid levels. Additionally, Lalgudi et al., (U.S. patent application Publication No. 2001/0051335 A1) disclose short DNA and protein fragments identified only as "corn tassel-derived polynucleotides (cdps) which encode corn tassel-derived proteins (CDPs)" which show sequence similarity to the GB1 sequence identified by the current inventors. Lalgudi et al., do not disclose a function for the cdps and CDPs in the synthesis of glycine-betaine, for water-deficit or cold tolerance, nor for increased yield. Alignments of proteins exhibiting homology to the maize GB1 protein of the current invention as well as alignments describing consensus regions are shown in FIG. 1 and FIG. 2 which are used to identify consensus amino acid sequences of SEQ ID NO:17 and SEQ ID NO:18, respectively.

Example 2

Over-Expression of Exogenous DNA Constructs Comprising gb1 Coding Sequence in Transgenic *Zea mays*

Transgenic *Zea mays* of a GB non-accumulator line was prepared with an exogenous DNA comprising a constitutive promoter region comprising a rice actin 1 promoter and a rice actin 1 intron operably linked to the gb1 coding sequence of SEQ ID NO:19 encoding the GB1 polynucleotide of SEQ ID NO:1 (see pMON78450 in FIG. 3 and SEQ ID NO:57). $R_o$ transgenic plants comprising low copy number events (that is, about 1-2 copies based upon molecular analysis) were selected for study. Transgenic non-accumulator plants comprising the gb1 exogenous DNA and non-transgenic control plants of both a GB non-accumulator line and a GB accumulator line were grown under greenhouse conditions and leaf samples taken at approximately the V6-V8 stage. Leaf samples from a total of 45 different transgenic events were examined for GB accumulation. Leaf samples were lyophilized, ground to a fine powder and metabolites extracted into an ethanol-based extraction buffer supplemented with deuterated glycine-betaine as an internal standard metabolite. Samples were analyzed by liquid chromatography-mass spectrometry/mass spectrometry and the amount of glycine-betaine (in mM) determined by analyzing the ratio of the deuterated and non-deuterated glycine-betaine in a sample.

Glycine-betaine was found to accumulate to significantly higher levels in the gb1 transgenic plants when compared to both the GB non-accumulator (LH59) and GB accumulator (FBLL) non-transgenic plants. On average, in the V6-V8 plants, the gb1 transgenic plants contained approximately 7.2 mM GB per sample as compared to 3.0 mM and 0.1 mM in the non-transgenic GB accumulator FBLL and GB non-accumulator LH244 lines, respectively. This represents an approximately 70-fold increase in GB in the transgenic plants compared to the non-transgenic GB non-accumulator lines and an approximately 2.4-fold increase compared to the GB non-transgenic accumulator line. As can been seen from Table 1, the range of accumulated GB in the transgenic plants was from 0.1 mM to 22.6 mM. $R_o$ transgenic plants were outcrossed and progeny seed prepared for propagation of $F_1$, $F_2$ and other generations of progeny plants and seeds and additional analysis of glycine-betaine indicated that the metabolite continued to accumulate to increased levels in the progeny plants (see for example, Tables 3 and 4 in Example 5).

Studies also indicated that the amount of GB in tissue increased with the age of the plant. For example, older VT leaves of a non-transgenic FBLL×LH59 hybrid accumulated more of the metabolite than younger V5 leaves.

TABLE 1

Glycine-betaine accumulation in $R_0$ gb1 transgenic plants.

| Line | Accumulator Type* | n | Mean GB(mM) | Std Dev | Min | Max |
|---|---|---|---|---|---|---|
| LH59/GB1 | Non-accumulator with transgene | 45[a] | 7.2 | 4.70 | 0.1 | 22.6 |
| LH59 | Non-accumulator | 11[b] | 0.1 | 0.14 | 0.008 | 0.4 |
| FBLL | Accumulator | 4[b] | 3.0 | 0.59 | 2.1 | 3.66 |

*Indicates characterization of maize line without transgene.
[a] = represents 45 different events, one plant from each event.
[b] = represents the number of individual plants of each non-transgenic line Example 3

Expression of Exogenous DNA Constructs Comprising gb1 Coding Sequence and Homologs in Transgenic *Zea mays*

In substantially the same manner as in Example 2, a variety of exogenous DNA constructs comprising a gb1 coding sequence are transformed into the GB non-accumulating maize line (LH59) and a GB accumulating maize line (FBLL MAB, U.S. patent application Publication 20040016030, incorporated herein by reference). The gb1-containing DNA constructs are substantially similar to the construct illustrated in FIG. 3 except for combinations of promoter and gb1 coding sequence as described Table 2 where the promoter identified by "promoter sequence" replaces the rice actin 1 promoter and the gb1 coding sequence identified by "gb1 DNA sequence" replaces the maize gb1 coding sequence. The rice actin 1 intron is retained or deleted or replaced with other introns in the various constructs.

TABLE 2

Coding sequence and promoter combinations for the expression of gb1 coding sequences.

| Promoter | Promoter sequence | gb1 | gb1 coding sequence |
|---|---|---|---|
| hsp17.5 promoter | SEQ ID NO:36 | maize gb1 | SEQ ID NO:19 |
| hva22 promoter | SEQ ID NO:37 | maize gb1 | SEQ ID NO:19 |
| ca4h promoter | SEQ ID NO:38 | maize gb1 | SEQ ID NO:19 |
| rab-17 promoter | SEQ ID NO:39 | maize gb1 | SEQ ID NO:19 |
| rab-17 promoter | SEQ ID NO:40 | maize gb1 | SEQ ID NO:19 |
| hsp17.5 promoter | SEQ ID NO:41 | maize gb1 | SEQ ID NO:19 |
| hva22 promoter | SEQ ID NO:42 | maize gb1 | SEQ ID NO:19 |
| ca4h promoter | SEQ ID NO:43 | maize gb1 | SEQ ID NO:19 |
| hsp16.9 promoter | SEQ ID NO:44 | maize gb1 | SEQ ID NO:19 |
| hsp22 promoter | SEQ ID NO:45 | maize gb1 | SEQ ID NO:19 |
| rab-17 promoter | SEQ ID NO:46 | maize gb1 | SEQ ID NO:19 |
| maize gb1 promoter | SEQ ID NO:47 | maize gb1 | SEQ ID NO:19 |
| maize cvy-cik1 promoter | SEQ ID NO:48 | maize gb1 | SEQ ID NO:19 |
| maize cvy-cik1 promoter | SEQ ID NO:49 | maize gb1 | SEQ ID NO:19 |
| maize cvy-cik1 promoter | SEQ ID NO:50 | maize gb1 | SEQ ID NO:19 |
| maize cvy-cik1 promoter | SEQ ID NO:51 | maize gb1 | SEQ ID NO:19 |

TABLE 2-continued

Coding sequence and promoter combinations for the expression of gb1 coding sequences.

| Promoter | Promoter sequence | gb1 | gb1 coding sequence |
|---|---|---|---|
| maize cvy-cik1 promoter | SEQ ID NO:52 | maize gb1 | SEQ ID NO:19 |
| rice cvy-cik1 promoter | SEQ ID NO:53 | maize gb1 | SEQ ID NO:19 |
| rtbv promoter | SEQ ID NO:54 | maize gb1 | SEQ ID NO:19 |
| maize nas promoter | SEQ ID NO:55 | maize gb1 | SEQ ID NO:19 |
| coix hrgp promoter | SEQ ID NO:56 | maize gb1 | SEQ ID NO:19 |
| rice actin 1 promoter and intron | SEQ ID NO:35 | maize gb1-2 | SEQ ID NO:20 |
| hsp17.5 promoter | SEQ ID NO:36 | maize gb1-2 | SEQ ID NO:20 |
| hva22 promoter | SEQ ID NO:37 | maize gb1-2 | SEQ ID NO:20 |
| ca4h promoter | SEQ ID NO:38 | maize gb1-2 | SEQ ID NO:20 |
| rab-17 promoter | SEQ ID NO:39 | maize gb1-2 | SEQ ID NO:20 |
| rab-17 promoter | SEQ ID NO:40 | maize gb1-2 | SEQ ID NO:20 |
| hsp17.5 promoter | SEQ ID NO:41 | maize gb1-2 | SEQ ID NO:20 |
| hva22 promoter | SEQ ID NO:42 | maize gb1-2 | SEQ ID NO:20 |
| ca4h promoter | SEQ ID NO:43 | maize gb1-2 | SEQ ID NO:20 |
| hsp16.9 promoter | SEQ ID NO:44 | maize gb1-2 | SEQ ID NO:20 |
| hsp22 promoter | SEQ ID NO:45 | maize gb1-2 | SEQ ID NO:20 |
| rab-17 promoter | SEQ ID NO:46 | maize gb1-2 | SEQ ID NO:20 |
| maize gb1 promoter | SEQ ID NO:47 | maize gb1-2 | SEQ ID NO:20 |
| maize cvy-cik1 promoter | SEQ ID NO:48 | maize gb1-2 | SEQ ID NO:20 |
| maize cvy-cik1 promoter | SEQ ID NO:49 | maize gb1-2 | SEQ ID NO:20 |
| maize cvy-cik1 promoter | SEQ ID NO:50 | maize gb1-2 | SEQ ID NO:20 |
| maize cvy-cik1 promoter | SEQ ID NO:51 | maize gb1-2 | SEQ ID NO:20 |
| maize cvy-cik1 promoter | SEQ ID NO:52 | maize gb1-2 | SEQ ID NO:20 |
| rice cvy-cik1 promoter | SEQ ID NO:53 | maize gb1-2 | SEQ ID NO:20 |
| rtbv promoter | SEQ ID NO:54 | maize gb1-2 | SEQ ID NO:20 |
| maize nas promoter | SEQ ID NO:55 | maize gb1-2 | SEQ ID NO:20 |
| coix hrgp promoter | SEQ ID NO:56 | maize gb1-2 | SEQ ID NO:20 |
| rice actin 1 promoter and intron | SEQ ID NO:35 | rice gb1-1 | SEQ ID NO:21 |
| hsp17.5 promoter | SEQ ID NO:36 | rice gb1-1 | SEQ ID NO:21 |
| hva22 promoter | SEQ ID NO:37 | rice gb1-1 | SEQ ID NO:21 |
| ca4h promoter | SEQ ID NO:38 | rice gb1-1 | SEQ ID NO:21 |
| rab-17 promoter | SEQ ID NO:39 | rice gb1-1 | S

TABLE 2-continued

Coding sequence and promoter combinations for the expression of gb1 coding sequences.

| Promoter | Promoter sequence | gb1 | gb1 coding sequence |
|---|---|---|---|
| hsp17.5 promoter | SEQ ID NO:36 | maize gb1-3-1 | SEQ ID NO:23 |
| hva22 promoter | SEQ ID NO:37 | maize gb1-3-1 | SEQ ID NO:23 |
| ca4h promoter | SEQ ID NO:38 | maize gb1-3-1 | SEQ ID NO:23 |
| rab-17 promoter | SEQ ID NO:39 | maize gb1-3-1 | SEQ ID NO:23 |
| rab-17 promoter | SEQ ID NO:40 | maize gb1-3-1 | SEQ ID NO:23 |
| hsp17.5 promoter | SEQ ID NO:41 | maize gb1-3-1 | SEQ ID NO:23 |
| hva22 promoter | SEQ ID NO:42 | maize gb1-3-1 | SEQ ID NO:23 |
| ca4h promoter | SEQ ID NO:43 | maize gb1-3-1 | SEQ ID NO:23 |
| hsp16.9 promoter | SEQ ID NO:44 | maize gb1-3-1 | SEQ ID NO:23 |
| hsp22 promoter | SEQ ID NO:45 | maize gb1-3-1 | SEQ ID NO:23 |
| rab-17 promoter | SEQ ID NO:46 | maize gb1-3-1 | SEQ ID NO:23 |
| maize gb1 promoter | SEQ ID NO:47 | maize gb1-3-1 | SEQ ID NO:23 |
| maize cvy-cik1 promoter | SEQ ID NO:48 | maize gb1-3-1 | SEQ ID NO:23 |
| maize cvy-cik1 promoter | SEQ ID NO:49 | maize gb1-3-1 | SEQ ID NO:23 |
| maize cvy-cik1 promoter | SEQ ID NO:50 | maize gb1-3-1 | SEQ ID NO:23 |
| maize cvy-cik1 promoter | SEQ ID NO:51 | maize gb1-3-1 | SEQ ID NO:23 |
| maize cvy-cik1 promoter | SEQ ID NO:52 | maize gb1-3-1 | SEQ ID NO:23 |
| rice cvy-cik1 promoter | SEQ ID NO:53 | maize gb1-3-1 | SEQ ID NO:23 |
| rtbv promoter | SEQ ID NO:54 | maize gb1-3-1 | SEQ ID NO:23 |
| maize nas promoter | SEQ ID NO:55 | maize gb1-3-1 | SEQ ID NO:23 |
| coix hrgp promoter | SEQ ID NO:56 | maize gb1-3-1 | SEQ ID NO:23 |
| rice actin 1 promoter and intron | SEQ ID NO:35 | leek gb1-3-1 | SEQ ID NO:24 |
| hsp17.5 promoter | SEQ ID NO:36 | leek gb1-3-1 | SEQ ID NO:24 |
| hva22 promoter | SEQ ID NO:37 | leek gb1-3-1 | SEQ ID NO:24 |
| ca4h promoter | SEQ ID NO:38 | leek gb1-3-1 | SEQ ID NO:24 |
| rab-17 promoter | SEQ ID NO:39 | leek gb1-3-1 | SEQ ID NO:24 |
| rab-17 promoter | SEQ ID NO:40 | leek gb1-3-1 | SEQ ID NO:24 |
| hsp17.5 promoter | SEQ ID NO:41 | leek gb1-3-1 | SEQ ID NO:24 |
| hva22 promoter | SEQ ID NO:42 | leek gb1-3-1 | SEQ ID NO:24 |
| ca4h promoter | SEQ ID NO:43 | leek gb1-3-1 | SEQ ID NO:24 |
| hsp16.9 promoter | SEQ ID NO:44 | leek gb1-3-1 | SEQ ID NO:24 |
| hsp22 promoter | SEQ ID NO:45 | leek gb1-3-1 | SEQ ID NO:24 |
| rab-17 promoter | SEQ ID NO:46 | leek gb1-3-1 | SEQ ID NO:24 |
| maize gb1 promoter | SEQ ID NO:47 | leek gb1-3-1 | SEQ ID NO:24 |
| maize cvy-cik1 promoter | SEQ ID NO:48 | leek gb1-3-1 | SEQ ID NO:24 |
| maize cvy-cik1 promoter | SEQ ID NO:49 | leek gb1-3-1 | SEQ ID NO:24 |
| maize cvy-cik1 promoter | SEQ ID NO:50 | leek gb1-3-1 | SEQ ID NO:24 |
| maize cvy-cik1 promoter | SEQ ID NO:51 | leek gb1-3-1 | SEQ ID NO:24 |
| maize cvy-cik1 promoter | SEQ ID NO:52 | leek gb1-3-1 | SEQ ID NO:24 |
| rice cvy-cik1 promoter | SEQ ID NO:53 | leek gb1-3-1 | SEQ ID NO:24 |
| rtbv promoter | SEQ ID NO:54 | leek gb1-3-1 | SEQ ID NO:24 |
| maize nas promoter | SEQ ID NO:55 | leek gb1-3-1 | SEQ ID NO:24 |
| coix hrgp promoter | SEQ ID NO:56 | leek gb1-3-1 | SEQ ID NO:24 |
| rice actin 1 promoter and intron | SEQ ID NO:35 | At gb1-3-1 | SEQ ID NO:25 |
| hsp17.5 promoter | SEQ ID NO:36 | At gb1-3-1 | SEQ ID NO:25 |
| hva22 promoter | SEQ ID NO:37 | At gb1-3-1 | SEQ ID NO:25 |
| ca4h promoter | SEQ ID NO:38 | At gb1-3-1 | SEQ ID NO:25 |
| rab-17 promoter | SEQ ID NO:39 | At gb1-3-1 | SEQ ID NO:25 |
| rab-17 promoter | SEQ ID NO:40 | At gb1-3-1 | SEQ ID NO:25 |
| hsp17.5 promoter | SEQ ID NO:41 | At gb1-3-1 | SEQ ID NO:25 |
| hva22 promoter | SEQ ID NO:42 | At gb1-3-1 | SEQ ID NO:25 |
| ca4h promoter | SEQ ID NO:43 | At gb1-3-1 | SEQ ID NO:25 |
| hsp16.9 promoter | SEQ ID NO:44 | At gb1-3-1 | SEQ ID NO:25 |
| hsp22 promoter | SEQ ID NO:45 | At gb1-3-1 | SEQ ID NO:25 |
| rab-17 promoter | SEQ ID NO:46 | At gb1-3-1 | SEQ ID NO:25 |
| maize gb1 promoter | SEQ ID NO:47 | At gb1-3-1 | SEQ ID NO:25 |
| maize cvy-cik1 promoter | SEQ ID NO:48 | At gb1-3-1 | SEQ ID NO:25 |
| maize cvy-cik1 promoter | SEQ ID NO:49 | At gb1-3-1 | SEQ ID NO:25 |
| maize cvy-cik1 promoter | SEQ ID NO:50 | At gb1-3-1 | SEQ ID NO:25 |
| maize cvy-cik1 promoter | SEQ ID NO:51 | At gb1-3-1 | SEQ ID NO:25 |
| maize cvy-cik1 promoter | SEQ ID NO:52 | At gb1-3-1 | SEQ ID NO:25 |
| rice cvy-cik1 promoter | SEQ ID NO:53 | At gb1-3-1 | SEQ ID NO:25 |
| rtbv promoter | SEQ ID NO:54 | At gb1-3-1 | SEQ ID NO:25 |
| maize nas promoter | SEQ ID NO:55 | At gb1-3-1 | SEQ ID NO:25 |
| coix hrgp promoter | SEQ ID NO:56 | At gb1-3-1 | SEQ ID NO:25 |
| rice actin 1 promoter and intron | SEQ ID NO:35 | At gb1-3-2 | SEQ ID NO:26 |
| hsp17.5 promoter | SEQ ID NO:36 | At gb1-3-2 | SEQ ID NO:26 |
| hva22 promoter | SEQ ID NO:37 | At gb1-3-2 | SEQ ID NO:26 |
| ca4h promoter | SEQ ID NO:38 | At gb1-3-2 | SEQ ID NO:26 |
| rab-17 promoter | SEQ ID NO:39 | At gb1-3-2 | SEQ ID NO:26 |
| rab-17 promoter | SEQ ID NO:40 | At gb1-3-2 | SEQ ID NO:26 |
| hsp17.5 promoter | SEQ ID NO:41 | At gb1-3-2 | SEQ ID NO:26 |

TABLE 2-continued

Coding sequence and promoter combinations for the expression of gb1 coding sequences.

| Promoter | Promoter sequence | gb1 | gb1 coding sequence |
|---|---|---|---|
| hva22 promoter | SEQ ID NO:42 | At gb1-3-2 | SEQ ID NO:26 |
| ca4h promoter | SEQ ID NO:43 | At gb1-3-2 | SEQ ID NO:26 |
| hsp16.9 promoter | SEQ ID NO:44 | At gb1-3-2 | SEQ ID NO:26 |
| hsp22 promoter | SEQ ID NO:45 | At gb1-3-2 | SEQ ID NO:26 |
| rab-17 promoter | SEQ ID NO:46 | At gb1-3-2 | SEQ ID NO:26 |
| maize gb1 promoter | SEQ ID NO:47 | At gb1-3-2 | SEQ ID NO:26 |
| maize cvy-cik1 promoter | SEQ ID NO:48 | At gb1-3-2 | SEQ ID NO:26 |

TABLE 2-continued

Coding sequence and promoter combinations for the expression of gb1 coding sequences.

| Promoter | Promoter sequence | gb1 | gb1 coding sequence |
|---|---|---|---|
| maize cvy-cik1 promoter | SEQ ID NO:48 | Bn gb1-3-1 | SEQ ID NO:29 |
| maize cvy-cik1 promoter | SEQ ID NO:49 | Bn gb1-3-1 | SEQ ID NO:29 |
| maize cvy-cik1 promoter | SEQ ID NO:50 | Bn gb1-3-1 | SEQ ID NO:29 |
| maize cvy-cik1 promoter | SEQ ID NO:51 | Bn gb1-3-1 | SEQ ID NO:29 |
| maize cvy-cik1 promoter | SEQ ID NO:52 | Bn gb1-3-1 | SEQ ID NO:29 |
| rice cvy-cik1 promoter | SEQ ID NO:53 | Bn gb1-3-1 | SEQ ID NO:29 |
| rt

TABLE 2-continued

Coding sequence and promoter combinations for the expression of gb1 coding sequences.

| Promoter | Promoter sequence | gb1 | gb1 coding sequence |
|---|---|---|---|
| rtbv promoter | SEQ ID NO:54 | barley gb1-3-1 | SEQ ID NO:32 |
| maize nas promoter | SEQ ID NO:55 | barley gb1-3-1 | SEQ ID NO:32 |
| coix hrgp promoter | SEQ ID NO:56 | barley gb1-3-1 | SEQ ID NO:32 |
| rice actin 1 promoter and intron | SEQ ID NO:35 | rice gb1-3-1 | SEQ ID NO:33 |
| hsp17.5 promoter | SEQ ID NO:36 | rice gb1-3-1 | SEQ ID NO:33 |
| hva22 promoter | SEQ ID NO:37 | rice gb1-3-1 | SEQ ID NO:33 |
| ca4h promoter | SEQ ID NO:38 | rice gb1-3-1 | SEQ ID NO:33 |
| rab-17 promoter | SEQ ID NO:39 | rice gb1-3-1 | SEQ ID NO:33 |
| rab-17 promoter | SEQ ID NO:40 | rice gb1-3-1 | SEQ ID NO:33 |
| hsp17.5 promoter | SEQ ID NO:41 | rice gb1-3-1 | SEQ ID NO:33 |
| hva22 promoter | SEQ ID NO:42 | rice gb1-3-1 | SEQ ID NO:33 |
| ca4h promoter | SEQ ID NO:43 | rice gb1-3-1 | SEQ ID NO:33 |
| hsp16.9 promoter | SEQ ID NO:44 | rice gb1-3-1 | SEQ ID NO:33 |
| hsp22 promoter | SEQ ID NO:45 | rice gb1-3-1 | SEQ ID NO:33 |
| rab-17 promoter | SEQ ID NO:46 | rice gb1-3-1 | SEQ ID NO:33 |
| maize gb1 promoter | SEQ ID NO:47 | rice gb1-3-1 | SEQ ID NO:33 |
| maize cvy-cik1 promoter | SEQ ID NO:48 | rice gb1-3-1 | SEQ ID NO:33 |
| maize cvy-cik1 promoter | SEQ ID NO:49 | rice gb1-3-1 | SEQ ID NO:33 |
| maize cvy-cik1 promoter | SEQ ID NO:50 | rice gb1-3-1 | SEQ ID NO:33 |
| maize cvy-cik1 promoter | SEQ ID NO:51 | rice gb1-3-1 | SEQ ID NO:33 |
| maize cvy-cik1 promoter | SEQ ID NO:52 | rice gb1-3-1 | SEQ ID NO:33 |
| rice cvy-cik1 promoter | SEQ ID NO:53 | rice gb1-3-1 | SEQ ID NO:33 |
| rtbv promoter | SEQ ID NO:54 | rice gb1-3-1 | SEQ ID NO:33 |
| maize nas promoter | SEQ ID NO:55 | rice gb1-3-1 | SEQ ID NO:33 |
| coix hrgp promoter | SEQ ID NO:56 | rice gb1-3-1 | SEQ ID NO:33 |
| rice actin 1 promoter and intron | SEQ ID NO:35 | wheat gb1-3-1 | SEQ ID NO:34 |
| hsp17.5 promoter | SEQ ID NO:36 | wheat gb1-3-1 | SEQ ID NO:34 |
| hva22 promoter | SEQ ID NO:37 | wheat gb1-3-1 | SEQ ID NO:34 |
| ca4h promoter | SEQ ID NO:38 | wheat gb1-3-1 | SEQ ID NO:34 |
| rab-17 promoter | SEQ ID NO:39 | wheat gb1-3-1 | SEQ ID NO:34 |
| rab-17 promoter | SEQ ID NO:40 | wheat gb1-3-1 | SEQ ID NO:34 |
| hsp17.5 promoter | SEQ ID NO:41 | wheat gb1-3-1 | SEQ ID NO:34 |
| hva22 promoter | SEQ ID NO:42 | wheat gb1-3-1 | SEQ ID NO:34 |
| ca4h promoter | SEQ ID NO:43 | wheat gb1-3-1 | SEQ ID NO:34 |
| hsp16.9 promoter | SEQ ID NO:44 | wheat gb1-3-1 | SEQ ID NO:34 |
| hsp22 promoter | SEQ ID NO:45 | wheat gb1-3-1 | SEQ ID NO:34 |
| rab-17 promoter | SEQ ID NO:46 | wheat gb1-3-1 | SEQ ID NO:34 |
| maize gb1 promoter | SEQ ID NO:47 | wheat gb1-3-1 | SEQ ID NO:34 |
| maize cvy-cik1 promoter | SEQ ID NO:48 | wheat gb1-3-1 | SEQ ID NO:34 |
| maize cvy-cik1 promoter | SEQ ID NO:49 | wheat gb1-3-1 | SEQ ID NO:34 |
| maize cvy-cik1 promoter | SEQ ID NO:50 | wheat gb1-3-1 | SEQ ID NO:34 |
| maize cvy-cik1 promoter | SEQ ID NO:51 | wheat gb1-3-1 | SEQ ID NO:34 |
| maize cvy-cik1 promoter | SEQ ID NO:52 | wheat gb1-3-1 | SEQ ID NO:34 |
| rice cvy-cik1 promoter | SEQ ID NO:53 | wheat gb1-3-1 | SEQ ID NO:34 |
| rtbv promoter | SEQ ID NO:54 | wheat gb1-3-1 | SEQ ID NO:34 |
| maize nas promoter | SEQ ID NO:55 | wheat gb1-3-1 | SEQ ID NO:34 |
| coix hrgp promoter | SEQ ID NO:56 | wheat gb1-3-1 | SEQ ID NO:34 |

Transgenic plants produced with a water-deficit-inducible, cold inducible, other stress inducible or any other promoter operably linked to an exogenous gb1 coding sequence of the present invention (see for example, Table 2) are subjected to various growing conditions to demonstrate the effect of expressing a gb1 coding sequence in the transgenic plants. Plants are exposed to cold conditions, water-deficit conditions, heat, saline and other stresses in the field and under green house conditions. The plants are exposed to the stress condition for a period of time long enough and/or severe enough to induce the action of a stress-inducible promoter, e.g. withholding water for at least three days, before the collection of leaf tissue samples. Sample tissue is collected from transgenic plants expressing an exogenous gb1 coding sequence of the present invention for evaluation. Leaf tissue is collected from leaves of several ages (V2, V4, V6, V8 and VT) following water-deficit treatment or root tissue is collected at 12 hour intervals after a cold treatment. When collected tissue from the transgenic plant comprising and expressing an exogenous gb1 coding sequence described in Table 2 is analyzed for glycine-betaine, elevated levels of glycine-betaine compared to the non-transgenic maize line are measured, similar to elevated levels produced in the transgenic plant reported in the preceding Example 2 and increased stress-protection resulting from the expression of the gb1 coding sequence in the tissues is demonstrated.

Example 4

Tolerance to Water Deficit by Transgenic Plants and Seed

Transgenic maize and seed, prepared as described in Examples 2 and 3, are subjected to water-deficit conditions and examined for increased tolerance to water-deficit.

In a controlled environment such as a greenhouse, water-deficit is imposed upon the plants and seeds by germinating seed under water-deficit conditions, and imposing water-deficit conditions on seedlings and plants at various stage of development, such as at V2, V4, V6, V8 and VT. Water-deficit is induced by withholding or limiting water. Water-deficit is also induced by the application of saline and PEG solutions which induce water-deficit. In a less controlled environment, such as a field, water-deficit conditions are achieved by growing in a geographical location in which rainfall is usually limiting and by withholding irrigation.

Several parameters are measured to determine increased tolerance to water-deficit: plant height, leaf length, shoot mass, seed set, number of seed, yield, photosynthesis, turgor pressure, osmotic potential, leaf extension rate, and germination. In the practice of the current invention, maize plants and seeds expressing an exogenous gb1 coding sequence and producing enhanced glycine-betaine demonstrate increased tolerance to water-deficit compared to control plants lacking the transgene, e.g., a non-transgenic segregant, a plant treated with GB or a plant that naturally accumulates GB. Moreover, a water-deficit tolerant maize plant and seed expressing an exogenous gb1 coding sequence has improved yield similar to, or increased upon, yield inherent in a GB accumulator maize line.

Transgenic soybean, cotton, canola and tobacco plants and seed are prepared with similar DNA constructs as described for maize, and similar water deficit studies carried out as described for maize. As compared to control plants and control seed lacking the exogenous DNA constructs, transgenic soybean cotton, canola and tobacco plants and seed with increased glycine-betaine content show increased tolerance for water-deficit conditions.

Example 5

Tolerance to Cold by Transgenic Plants and Seed

Transgenic maize, prepared as described in Examples 2 and 3, are subjected to cold conditions and examined for increased tolerance to cold. Of particular interest is the ability of the seed of the transgenic maize to germinate under cold temperatures, to tolerate a period of cold temperature after germination, and the ability of a young seedling to tolerate a period of cold temperature.

Several parameters are measured to determine increased tolerance to cold such as measuring germination, plant height, leaf length, root length, root mass, shoot mass, chlorophyll fluorescence, and yield. In the practice of the current invention, transgenic maize plants and seed expressing an exogenous gb1 coding sequence and producing enhanced glycine-betaine demonstrate increased tolerance to cold conditions compared to control plants lacking the transgene, e.g., a non-transgenic segregant, a plant treated with GB or a plant that naturally accumulates GB. For example, a transgenic cold tolerant maize plant or seed expressing an exogenous gb1 coding sequence has improved yield similar to, or increased upon, yield inherent in a GB accumulator maize line.

Germination Under Cold Condition

Hybrid seeds were produced by crossing pMON78450 (FIG. 3) transgenic $R_2$ plants prepared in Example 2 with two different tester lines: FBLL which naturally accumulates glycine-betaine, or LH244 which is naturally a non-accumulator line. The hybrid seeds from several different transgenic events comprising the exogenous gb1 coding sequence from pMON78450, as well as non-transgenic negative segregant maize kernels, were germinated under cold conditions. One hundred kernels were tested for each transgenic event and non-transgenic negative segregant. Batches of ten kernels each were germinated in Petri dishes lined with moistened filter paper in a growth chamber at approximately 9.5-9.8° C. in constant darkness. Water was added to the plates throughout the test as necessary.

Each day, the number of seeds germinated per plate was counted. A seed was considered to be germinated when the root radicle reached 1 cm. At the end of the test, root tip tissue was sampled from a number of seedlings per event and metabolites were extracted in order to determine the levels of glycine-betaine. For glycine-betaine measurements, samples were lyophilized, ground to a fine powder and metabolites extracted into an ethanol-based extraction buffer supplemented with deuterated glycine-betaine as an internal standard metabolite. Samples were analyzed by liquid chromatography-mass spectrometry/mass spectrometry and the amount of glycine-betaine (in ppm) determined by analyzing the ratio of the deuterated and non-deuterated glycine-betaine in comparison to a standard curve.

A control experiment was also performed under non-cold conditions. Batches of ten kernels each were germinated in Petri dishes lined with moistened filter paper in a growth chamber set at 27° C. in constant darkness. Fifty kernels were tested for each transgenic event and non-transgenic negative segregant.

Three different calculations were used to analyze the cold germination data:

1. Germination Index: This is a calculation which takes into account the time required by a given set of seeds, e.g., the 100 kernels representing a transgenic event, to germinate relative to other sets of seeds in the test as well as the total number of seed which germinate in a given experiment. A higher germination index number indicates a faster germination time and better overall germination performance for a given set of seeds. The formula used is:

Germination index=$((T \times P1)+((T-1) \times P2)+((T-2) \times P3)+ \ldots +(1 \times PT))/T$ In which T=the total number of days of the test P1, P2, P3, and PT=the percentage of seeds which germinated on that specific day of the test 2. Total Percent Germination: The percent of seeds which germinated for each set of seeds at the end of an experiment.

3. Days Until 50% Germination: This calculates the average number of days until half of the seeds being tested for a particular set of seeds have germinated. The model used to estimate the days to 50% germination is a three-parameter logistic model. This nonlinear model was fit using the statistical software package, JMP® (JMP®, version 5.1, 1989-2003 SAS Institute Inc. Cary, N.C.). The fitted model was found using an iterative optimization procedure.

Germination Under Non-Cold Condition Followed by Cold Condition: Early Seedling Test Seeds from a number of gb1 transgenic events and non-transgenic negative segregants were germinated on moistened vertical rolls of germination paper. Three rolls were set up for each selection, with 16 kernels used for each roll. For the cold assay, the seedlings were first germinated at about 23° C. for three days before being transferred to a chamber at a constant 12° C. for an additional 10 days. For the non-cold assay, seedlings were germinated in rolled germination paper at about 23° C. for five days. At the end of the test period, root and shoot length were determined for the seeds exposed to cold and non-cold conditions.

Germination Under Non-Cold Condition Followed by Cold Condition: Young Seedling Soil Test Seeds from a number of gb1 transgenic events and non-transgenic negative segregants were germinated in individual pots of soil at 23° C. until they reached the V1 stage for testing (about 10 days; 12 hour light/dark cycle). The young seedlings were then transferred to cold condition (about 8° C. during the light cycles, 5° C. in the dark cycles) for 8 days, after which they were transferred back to non-cold condition (about 23° C.) for recovery. On the fourth day of the cold treatment, the chlorophyll fluorescence of each of the young seedlings was measured. Three days after the young seedlings were returned to 23° C., two measurements were made: 1) leaf necrosis of each young seedling was estimated on the V2 leaf by visually estimating the percent of each V2 leaf which was still green at this stage and 2) the length of the V3 leaf (from soil to tip) was measured. This length was measured again at six days after recovery, to compare the growth rates after recovery for the transgenic and non-transgenic control young seedlings.

Tables 3 and 4 summarize the results of expressing an exogenous gb1 coding sequence having the sequence of SEQ ID NO:19 encoding a GB1 protein having an amino acid sequence of SEQ ID NO:1 which results in increased glycine-betaine on cold germination of transgenic hybrid maize seeds where one parent was a non-accumulating line (LH244; Table 3) or where one parent naturally accumulated glycine-betaine (FBLL; Table 4). The values for the Germination Index, Total Percent Germination and Days Until 50% Germination are reported as is the average amount of glycine-betaine accumulated by the transgenic or control negative segregant germinating root tip tissue.

The data indicate that of the eight gb1 transgenic events tested in the LH244 hybrid (Table 3), four events exhibited a statistically significant improvement in germination index and in total percent germination relative to the negative segregant seed. In addition, four events also demonstrated an improved germination time, as shown by the reduced number of days until 50% germination was achieved. In the early seedling test, the roots and shoots of the seedlings from one transgenic event were longer relative to the negative segregant, and in the young seedling soil test, the leaf length of one transgenic event was increased relative to the negative segregant. All events exhibiting an improvement in at least one cold germination, early seedling or young seedling characteristic accumulated at least 75 ppm glycine-betaine in the root tip tissue of the germinating seed. One event accumulating more than 75 ppm glycine-betaine did not exhibit an improvement in any of the measured parameters. On average, for all events in the LH244 hybrid plants, the improvement in germination index and total % germination in the cold were statistically significant at P<0.0015 and P<0.0017, respectively. The results from the non-cold condition germination test indicated that all of the seed used in the test were of good quality.

The data indicate that of the eight gb1 transgenic events tested in the FBLL hybrid (Table 4), three events exhibited a statistically significant improvement in germination index as well as in germination time relative to the negative segregant seed. One event demonstrated an improved total percent germination relative to the negative segregant seed. In the early seedling test, the roots and/or shoots of the seedlings from three transgenic events were longer relative to the negative segregant, and in the young seedling soil test, the leaf length of one transgenic event was increased relative to the negative segregant. On average, for all events in the FBLL hybrid plants, the improvement in germination index and total % germination in the cold were statistically significant at P<0.0037 and P<0.1403, respectively. The results from the non-cold condition germination test indicate that all of the seed used in the test were of good quality.

The results reported in Tables 3 and 4 show that over-expression of the maize gb1 transgene, and resultant increase in glycine-betaine accumulation, increases the cold germination of the non-accumulator LH244 seeds to a greater degree than that of the naturally accumulating FBLL line in these tests.

TABLE 3

Effect of gb1 over-expression in LH244 (non-accumulating line)

| Event | Trans-gene[a] | ppm GB Avg[b] | Germination Index Avg[c] | Total % Germination Avg[c] | Days to 50% Germination Avg[c] |
|---|---|---|---|---|---|
| M44196 | POS | 151 | 27.81 | 77 | 16.7 |
| M44196 | neg | 2 | 41.78 | 98 | 15.6 |
| M44199 | POS | 269 | 41.77 | 96 | 15.3^ |
| M44199 | neg | 2 | 38.06 | 93 | 16.2 |
| M44202 | POS | 113 | 31.82**** | 89* | 16.8^ |
| M44202 | neg | 1 | 19.82 | 77 | 19.2 |
| M45434 | POS | 76 | 31.99 | 90 | 17.3^ |
| M45434 | neg | 2 | 27.74 | 85 | 18.1 |
| M45441 | POS | 48 | 29.91 | 90 | 18.0 |
| M45441 | neg | 2 | 32.36 | 94 | 17.3 |
| M45444 | POS | 181 | 25.19**** | 87*** | 18.8^ |
| M45444 | neg | 2 | 13.34 | 57 | 19.8 |
| M46403 | POS | 184 | 29.74**** | 82**** | 17.1 |
| M46403 | neg | 1 | 17.96 | 48 | 16.6 |
| M46411 | POS | 124 | 27.91* | 83* | 17.9 |
| M46411 | neg | 2 | 22.71 | 72 | 17.9 |
| Average | POS | | 31.2** | 87.2** | |
| Average | Neg | | 27 | 79.4 | |

[a]Pos = presence of the exogenous maize gb1 coding sequence (pMON78450; SEQ ID NO: 19);
Neg = the absence of the gb1 transgenic coding sequence.
[b]Average is per 3 replicates of 3 pieces of root tissue measured under cold condition
[c]Average is per set of 100 kernels
*P < 0.06, positive improvement
**P < 0.01, positive improvement
***P < 0.001, positive improvement
****P < 0.0001, positive improvement
^high and low confidence limit values did not overlap and at least about 1 day of improvement

TABLE 4

Effect of gb1 over-expression in FBLL (accumulating line)

| Event | Trans-gene[a] | ppm gb Avg[b] | Germination Index Avg[c] | Total % Germination Avg[c] | Days to 50% Germination Avg[c] |
|---|---|---|---|---|---|
| M44196 | POS | 109 | 46.9** | 99 | 14.4^ |
| M44196 | neg | 12 | 40.5 | 99 | 15.7 |
| M44199 | POS | 204 | 39.9 | 97 | 15.5 |
| M44199 | neg | 3 | 43.7 | 100 | 15.4 |
| M44202 | POS | 114 | 46.4 | 98 | 14.4 |
| M44202 | neg | 4 | 43.4 | 95 | 14.8 |
| M45434 | POS | 95 | 45.6*** | 99* | 14.6^ |
| M45434 | neg | 2 | 39.4 | 94 | 15.6 |
| M45441 | POS | 45 | 44.1* | 96 | 14.8^ |
| M45441 | neg | 2 | 38.1 | 91 | 15.9 |
| M45444 | POS | 133 | 40.6 | 94 | 15.0 |
| M45444 | neg | 7 | 39.2 | 94 | 15.7 |
| M45445 | POS | 99 | 42.2 | 97 | 14.8 |
| M45445 | neg | 1 | 42.8 | 96 | 15.1 |
| M46403 | POS | 140 | 36.9 | 94 | 16 |
| M46403 | neg | 2 | 37.9 | 90 | 15.7 |
| Average | POS | | 42.5** | 96.8 | |
| Average | Neg | | 40.2 | 95.3 | |

[a]Pos = presence of the exogenous maize gb1 coding sequence (pMON78450; SEQ ID NO: 19);
Neg = the absence of the gb1 transgenic coding sequence.
[b]Average is per 3 replicates of 3 pieces of root tissue measured under cold condition. Note that by the V2 stage, the non-transgenic FBLL line accumulated about 25–30 ppm GB compared to about 2–2.5 ppm for the non-transgenic LH244 line.
[c]Average is per set of 100 kernels
*P < 0.06, positive improvement
**P < 0.01, positive improvement
***P < 0.001, positive improvement
****P < 0.0001, positive improvement
^high and low confidence limit values did not overlap and at least about 1 day of improvement Transgenic soybean, cotton, canola and tobacco are prepared with similar DNA constructs as described for maize, and similar studies carried out as described for maize. As compared to plants lacking the exogenous DNA constructs, e.g., non-gb1 plants, transgenic soybean, cotton, canola and tobacco with increased glycine-betaine content show increased tolerance for cold conditions.

---

We claim:

1. A transgenic seed having in its genome an exogenous DNA comprising a gb1 coding sequence which expresses a protein having the amino acid sequence of SEQ ID NO:1, wherein the activity of said protein increases glycine-betaine in a transgenic plant grown from said transgenic seed.

2. The transgenic seed of claim 1 wherein said exogenous DNA comprising a gb1 coding sequence has at least 98% identity to the nucleotide sequence of SEQ ID NO:19.

3. The transgenic seed of claim 2 wherein said exogenous DNA comprising a gb1 coding sequence has the nucleotide sequence of SEQ ID NO:19.

4. The transgenic seed of claim 1 wherein said exogenous DNA comprising a gb1 coding sequence is operably linked to a promoter functional in plants.

5. The transgenic seed of claim 4 wherein said promoter is selected from the promoters indicated in Table 2.

6. The transgenic seed of claim 1 wherein said transgenic seed produces a transgenic plant which is a crop plant selected from the group consisting of a variety of maize, soybean, rice, wheat, canola, cotton, sorghum, tobacco, sunflower, alfalfa, barley, millet, and turfgrass.

7. The transgenic seed of claim 6 wherein said transgenic seed is an inbred or hybrid transgenic maize seed.

8. A transgenic plant grown from a transgenic seed of claim 6.

9. The transgenic plant of claim 8 wherein said transgenic plant is an inbred or hybrid maize transgenic plant.

10. The transgenic seed according to claim 1 wherein said transgenic seed exhibits increased cold tolerance when exposed to temperatures between about 0° C. and about 10° C., wherein said exposure occurs
    a) within one week of planting; or
    b) within two weeks of planting; or
    c) within one month of planting; or
    d) because of an early planting date; or
    e) because of planting in a shorter relative maturity zone.

11. A method comprising multiplying or breeding plant material to obtain a transgenic crop plant from the transgenic seed of claim 1.

12. The method according to claim 11, wherein said transgenic crop plant exhibits
    a) increased tolerance to water-deficit; or
    b) increased yield under water-deficit growing conditions; or
    c) increased yield under non-water deficit growing conditions; or
    d) increased tolerance to cold; or
    e) increased tolerance to freezing, as compared to a control plant lacking said exogenous DNA.

13. The method of claim 12 wherein said transgenic crop plant exhibits increased cold tolerance when exposed to temperatures between about 0° C. and about 10° C., wherein said exposure occurs
    a) within one week of planting; or
    b) within two weeks of planting; or
    c) within one month of planting; or
    d) within one month of harvest; or
    e) because of an early planting date; or
    f) because of planting in a shorter relative maturity zone.

14. The method of claim 12 wherein said transgenic seed exhibits increased cold tolerance when exposed to temperatures between about 0° C. and about 10° C., wherein said exposure occurs
    a) within one week of planting; or
    b) within two weeks of planting; or
    c) within one month of planting; or
    d) because of an early planting date; or
    e) because of planting in a shorter relative maturity zone.

* * * * *

UNITED STATES PATENT AND TRADEMARK OFFICE
CERTIFICATE OF CORRECTION

| | |
|---|---|
| PATENT NO. | : 7,410,800 B2 |
| APPLICATION NO. | : 10/839092 |
| DATED | : August 12, 2008 |
| INVENTOR(S) | : Robert Bensen et al. |

Page 1 of 1

It is certified that error appears in the above-identified patent and that said Letters Patent is hereby corrected as shown below:

Title page item 75
In accordance with the attached coverletter, the following inventors should be removed from the list of inventors: John Korte and Brendan Hinchey.

The correct inventors are: Robert Bensen, Paolo Castiglioni, Erin Bell, Paul Loida, and Jeffrey Ahrens.

Signed and Sealed this

Twenty-fifth Day of November, 2008

JON W. DUDAS
*Director of the United States Patent and Trademark Office*

SEQUENCE LISTING

<160> NUMBER OF SEQ ID NOS: 57

<210> SEQ ID NO 1
<211> LENGTH: 306
<212> TYPE: PRT
<213> ORGANISM: Zea mays

<400> SEQUENCE: 1

```
Met Ile Pro Tyr Ala Thr Ala Ala Glu Ala Glu Gly Ala Leu Gly Arg
1               5                   10                  15

Thr Met Thr Trp Ala Glu Thr Ala Trp Tyr Glu Tyr Ser Ala Val Met
            20                  25                  30

Pro Asp Ser Trp Leu His Cys His Thr Thr Phe Ile Leu Phe Val Ile
        35                  40                  45

Tyr Ser Ile Ala Pro Leu Pro Leu Leu Leu Glu Gln Phe Ala Pro
    50                  55                  60

Ser Val Val Leu Pro Tyr Lys Leu Gln Pro Arg Val Arg Leu Pro Pro
65                  70                  75                  80

Ala Ala Ser Leu Ser Cys Tyr Met Asp Ala Ala Cys Ile Phe Pro Leu
                85                  90                  95

Ala Val Gly Leu Gln Phe Val Ser Tyr Pro Ala Val Ala Lys Ile Leu
            100                 105                 110

Arg Thr Arg Met Gly Leu Pro Leu Pro Ser Val Arg Glu Thr Ile Ala
            115                 120                 125

Gln Leu Val Val Tyr Ser Leu Val Glu Asp Tyr Leu Ser Tyr Trp Met
    130                 135                 140

His Arg Leu Leu His Thr Gln Trp Cys Tyr Glu Lys Ile His Arg Val
145                 150                 155                 160

His His Glu Phe Thr Ala Pro Thr Gly Phe Ala Met Ser Tyr Ser His
                165                 170                 175

Trp Ala Glu Asn Val Val Leu Ser Ile Pro Ala Leu Ala Gly Pro Val
            180                 185                 190

Leu Val Pro Cys His Val Thr Thr Gln Trp Leu Trp Phe Ser Ile Arg
            195                 200                 205

Leu Ile Glu Gly Ile Asn Thr His Ser Gly Tyr His Phe Pro Phe Ser
    210                 215                 220

Pro Cys Arg Leu Ile Pro Phe Tyr Gly Gly Ala Ala Tyr His Asp Tyr
225                 230                 235                 240

His His Tyr Ala Gly Gly Arg Ser Gln Ser Asn Phe Ala Pro Leu Phe
                245                 250                 255

Thr Tyr Cys Asp Tyr Leu Tyr Arg Thr Asp Lys Gly Tyr Arg Tyr His
            260                 265                 270

Lys Leu Lys Gln Glu Lys Leu Lys Ser Leu Ala Glu Asn Ser Ala Asp
            275                 280                 285

Lys Gly Gly Asn Tyr Ser Phe Asp Glu Gly Lys Lys Asn Arg Tyr Phe
    290                 295                 300

Cys Ala
305
```

<210> SEQ ID NO 2
<211> LENGTH: 293

```
<212> TYPE: PRT
<213> ORGANISM: Zea mays

<400> SEQUENCE: 2

Met Met Pro Tyr Gly Thr Ala Ala Glu Ala Glu Ala Ala Leu Gly Arg
1               5                   10                  15

Ser Met Thr Trp Ala Glu Ala Leu Trp Phe Arg Tyr Ser Ala Gly Met
            20                  25                  30

Pro Asp Leu Cys Leu Thr Trp His Val Ser Leu Val Tyr Leu Val Leu
        35                  40                  45

Tyr Ala Leu Val Pro Leu Pro Val Met Val Ile Gln Lys Leu Ala Pro
    50                  55                  60

Gly Tyr Ala Leu Arg His Lys Leu Gln Pro Gly Val Pro Glu Pro Ser
65                  70                  75                  80

Pro Val Ser Thr Tyr Val Glu Tyr Ile Arg Asp Ser Arg Gly Val Thr
                85                  90                  95

Leu Ala Ala Leu Gly Pro Phe Pro Leu Ile Tyr Ser Ile Ala Phe Lys
            100                 105                 110

Leu Phe Gly Val Arg Thr Gly Leu Pro Leu Pro Ser Val Trp Glu Thr
        115                 120                 125

Ala Thr His Leu Ala Val Tyr Ser Leu Val Glu Asp Tyr Thr Ser Tyr
    130                 135                 140

Trp Leu His Arg Phe Leu His Thr Arg Trp Gly Tyr Glu Lys Ile His
145                 150                 155                 160

Arg Val His His Glu Lys Thr Ala Pro Ser Gly Phe Ala Ala Ala Tyr
                165                 170                 175

Ala Thr Gly Thr Glu Leu Ser Leu Tyr Leu Thr Thr Leu Phe Leu Gly
            180                 185                 190

Pro Ala Ile Val Pro Ser His Val Thr Thr His Trp Leu Leu Phe Ser
        195                 200                 205

Ile Arg Ile Met Glu Ala Phe Asp Thr His Ser Gly Tyr His Phe Pro
    210                 215                 220

Phe Ser Leu Ala Arg Phe Ile Pro Phe Tyr Gly Gly Ala Glu Phe His
225                 230                 235                 240

Asp Tyr His His Tyr Ala Gly Glu Lys Thr Arg Ser Asn Phe Ser Ser
                245                 250                 255

Val Phe Thr Tyr Cys Asp Tyr Ile Tyr Gly Thr Asn Lys Gly Tyr Met
            260                 265                 270

Tyr His Lys Arg Ser Leu Ala Glu Leu Lys Thr Lys Glu Ala Glu His
        275                 280                 285

Ser Gly Lys Glu Asp
    290

<210> SEQ ID NO 3
<211> LENGTH: 284
<212> TYPE: PRT
<213> ORGANISM: Oryza sativa

<400> SEQUENCE: 3

Met Leu Pro Tyr Ala Thr Ala Ala Glu Ala Glu Ala Ala Val Gly Arg
1               5                   10                  15

Gly Leu Thr Trp Ala Glu Ala Ala Trp Phe Arg Tyr Ser Ala Ala Ile
            20                  25                  30

Pro Asp Tyr Cys Leu Tyr Cys His Asn Val Pro Ile Leu Leu Leu Val
        35                  40                  45
```

```
Tyr Thr Leu Ala Pro Leu Pro Leu Ala Leu Leu Glu Leu Arg Arg His
        50                  55                  60

Leu Pro Leu Pro His Lys Leu Gln Pro Gly Val Arg His Pro Ala
 65                  70                  75                  80

Ala Phe Leu Arg Cys Tyr Ala Ala Thr Ala Arg Val Leu Leu Leu Ala
                 85                  90                  95

Val Gly Pro Val Gln Leu Ala Ser Phe Pro Ala Val Arg Ala Val Gly
            100                 105                 110

Ile Arg Thr Gly Leu Pro Leu Pro Ser Ala Gly Glu Thr Ala Ala Gln
            115                 120                 125

Val Ala Val Tyr Leu Leu Val Glu Asp Tyr Leu Gly Tyr Trp Ile His
        130                 135                 140

Arg Leu Leu His Thr Pro Trp Ala Tyr His His Ile His Arg Val His
145                 150                 155                 160

His Glu Phe Thr Ala Pro Met Gly Tyr Ala Ala Pro Tyr Ala His Trp
                165                 170                 175

Ala Glu Ile Leu Ile Leu Gly Phe Pro Ala Phe Ala Gly Pro Ala Ile
                180                 185                 190

Val Pro Cys His Met Thr Thr Phe Trp Leu Trp Phe Val Leu Arg His
            195                 200                 205

Leu Glu Ala Ile His Ile His Ser Gly Phe Lys Leu Pro Phe Asp Pro
        210                 215                 220

Thr Lys Tyr Ile Pro Leu Tyr Gly Gly Val Glu Tyr His Asp Tyr His
225                 230                 235                 240

His Phe Val Gly Gly His Ser Gln Ser Asn Phe Ser Ser Val Phe Thr
                245                 250                 255

Phe Cys Asp Tyr Ile Tyr Gly Thr Asp Arg Gly Tyr Arg Tyr His Lys
            260                 265                 270

Ala Ser Leu Ser Lys Met Arg Ile Phe Val Arg Ala
        275                 280

<210> SEQ ID NO 4
<211> LENGTH: 301
<212> TYPE: PRT
<213> ORGANISM: Hordeum vulgare
<220> FEATURE:
<221> NAME/KEY: misc_feature
<222> LOCATION: (185)..(185)
<223> OTHER INFORMATION: Xaa can be any naturally occurring amino acid

<400> SEQUENCE: 4

Met Leu Pro Tyr Ala Thr Thr Gly Asp Ala Glu Ala Ala Leu Gly Arg
  1               5                  10                  15

Ala Leu Thr Trp Ala Glu Ala Ala Trp Leu Arg Tyr Ser Ala Ser Val
                 20                  25                  30

Pro Asp Arg Tyr Leu His Trp Pro Asn Ile Ala Ile Thr Leu Val Val
             35                  40                  45

Tyr Thr Leu Ala Pro Leu Pro Leu Ala Leu Phe Asp Leu Ala Ala Pro
         50                  55                  60

Ala Val Ala Ala Pro Tyr Lys Leu Gln Pro Lys Val Gln His Pro Pro
 65                  70                  75                  80

Ala Thr Phe Phe Arg Cys Tyr Met Asp Ala Val Arg Val Ser Leu Leu
                 85                  90                  95

Ile Ile Gly Pro Tyr Gln Leu Ile Ser Tyr Pro Ala Ala Lys Ile Met
            100                 105                 110

Asp Ile Arg Thr Gly Leu Pro Leu Pro Ser Met Gly Glu Ile Ala Ala
```

```
                115                 120                 125
Gln Leu Thr Val Tyr Phe Leu Val Glu Asp Tyr Leu Asn Tyr Trp Leu
    130                 135                 140

His Arg Leu Leu His Thr Lys Trp Cys Tyr Glu Lys Ile His His Val
145                 150                 155                 160

His His Glu Phe Thr Ala Pro Met Ala Tyr Ala Ala Trp Tyr Gly His
                165                 170                 175

Trp Ala Glu Met Leu Ile Leu Ala Xaa Pro Ser Leu Ala Gly Pro Ala
            180                 185                 190

Leu Val Pro Cys His Val Thr Thr Leu Trp Ile Trp Phe Ala Ala Arg
        195                 200                 205

Leu Val Glu Ser Leu Asn Ile His Ser Gly Phe Lys Leu Pro Phe Asn
    210                 215                 220

Ala Glu Lys Tyr Ile Pro Phe Tyr Gly Gly Ala Glu His His Asp Tyr
225                 230                 235                 240

His His Tyr Ile Gly Gly Gln Ser Lys Ser Asn Phe Ala Pro Val Phe
                245                 250                 255

Thr Tyr Cys Asp Tyr Ile Tyr Gly Thr Asp Lys Gly Tyr Arg Tyr His
            260                 265                 270

Lys Ala Thr Leu Ala Lys Leu Lys Glu Leu Ala Gly Asn Glu Val Gln
        275                 280                 285

Lys Gly Val Asp Asn Gly Phe Asn Ser Gly Lys Gln Glu
    290                 295                 300

<210> SEQ ID NO 5
<211> LENGTH: 301
<212> TYPE: PRT
<213> ORGANISM: Zea mays

<400> SEQUENCE: 5

Met Leu Pro Tyr Ala Thr Ala Ala Glu Ala Glu Ala Ala Leu Gly Arg
1               5                   10                  15

Pro Met Thr Pro Ala Glu Ala Leu Trp Phe Arg Tyr Thr Ala Gly Val
            20                  25                  30

Ser Asp Tyr His Leu Tyr Cys Cys Asn Ile Leu Phe Leu Phe Val Val
        35                  40                  45

Phe Thr Val Ala Pro Leu Pro Ile Ala Leu Leu Glu Leu Arg Ala Pro
    50                  55                  60

Ala Ala Val Ser Pro Tyr Lys Leu Gln Pro Arg Val Arg Leu Ser Arg
65                  70                  75                  80

Ala Glu Phe Val Arg Cys Tyr Lys Asp Val Leu Arg Ile Phe Phe Leu
                85                  90                  95

Val Ile Gly Pro Leu Gln Leu Val Ser Tyr Pro Ala Val Lys Phe Val
            100                 105                 110

Gly Ile His Thr Lys Leu Pro Leu Pro Ser Leu Ala Glu Leu Ala Ala
        115                 120                 125

Gln Leu Leu Val Tyr Phe Leu Val Glu Asp Tyr Leu Asn Tyr Trp Ile
    130                 135                 140

His Arg Phe Leu His Gly Glu Trp Gly Tyr Gln Asn Ile His Arg Val
145                 150                 155                 160

His His Glu Phe Thr Ala Pro Ile Gly Phe Ala Ala Pro Tyr Ala His
                165                 170                 175

Trp Ala Glu Val Leu Ile Leu Gly Ile Pro Ser Phe Val Gly Pro Ala
            180                 185                 190
```

```
Ile Val Pro Gly His Met Ile Thr Phe Trp Leu Trp Ile Ile Leu Arg
            195                 200                 205

Gln Val Glu Ala Ile Glu Thr His Ser Gly Phe Asp Phe Pro Phe Thr
        210                 215                 220

Pro Thr Lys Tyr Ile Pro Phe Tyr Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Leu Tyr Gly Thr Asp Lys Gly Tyr Arg Phe His
            260                 265                 270

Lys Thr Tyr Leu Ala Lys Leu Lys Asp Leu Gly His Asn Asp Gly Gln
        275                 280                 285

Lys Gly Asp Gly Ser Gly Pro Ser Tyr Val Lys Leu Asp
    290                 295                 300

<210> SEQ ID NO 6
<211> LENGTH: 299
<212> TYPE: PRT
<213> ORGANISM: Allium porrum

<400> SEQUENCE: 6

Met Ile Pro Tyr Pro Ser Leu Thr Ala Ala Glu Ala Ala Leu Asn Arg
1               5                   10                  15

Pro Leu Thr Tyr Ala Glu Thr Ile Trp Phe Asn Tyr Ser Ala Thr Ile
            20                  25                  30

Pro Asp Pro Leu Leu Tyr Tyr His Asn Thr Ile Phe Leu Phe Val Ile
        35                  40                  45

Phe Thr Leu Val Pro Leu Pro Leu Ala Leu Leu Glu Leu Tyr Trp Pro
    50                  55                  60

Ser Val Leu Lys Pro Phe Lys Ile Gln Pro Lys Val Tyr Leu Ser Lys
65              70                  75                  80

Ser Glu Phe Leu Glu Cys Tyr Lys Asn Val Ile Lys Val Phe Phe Leu
                85                  90                  95

Val Val Cys Pro Leu Gln Leu Leu Ser Tyr Pro Thr Val Lys Phe Val
            100                 105                 110

Gly Ile Arg Thr Gly Leu Pro Leu Pro Ser Val Trp Glu Val Ala Ser
        115                 120                 125

Gln Leu Ala Val Tyr Phe Leu Leu Glu Asp Phe Gly Asn Tyr Trp Ile
    130                 135                 140

His Arg Trp Leu His Gly Lys Trp Gly Tyr Glu Lys Ile His Lys Val
145                 150                 155                 160

His His Glu Tyr Thr Ala Pro Ile Gly Phe Ala Ala Pro Tyr Ala His
                165                 170                 175

Trp Ala Glu Val Leu Ile Leu Gly Ile Pro Ser Phe Leu Gly Pro Ala
            180                 185                 190

Ile Val Pro Gly His Met Ile Thr Leu Trp Leu Trp Ile Ala Leu Arg
        195                 200                 205

Gln Ile Glu Ala Leu Asp Thr His Ser Gly Tyr Asp Phe Pro Leu Ser
    210                 215                 220

Phe Thr Lys Phe Ile Pro Phe Tyr Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Val Tyr Gly Thr Asp Lys Gly Tyr Arg Tyr Arg
            260                 265                 270
```

Lys Ala Cys Leu Ser Met Met Lys Glu Glu Ser Glu Asn Gln Asn Gly
            275                 280                 285

Val Glu Asn Ser Phe Gln Asn Gln Lys Ser Asp
        290                 295

<210> SEQ ID NO 7
<211> LENGTH: 298
<212> TYPE: PRT
<213> ORGANISM: Arabidopsis thaliana

<400> SEQUENCE: 7

Met Ile Pro Tyr Ala Thr Val Glu Glu Ala Ser Ile Ala Leu Gly Arg
1               5                   10                  15

Asn Leu Thr Arg Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Val
        35                  40                  45

Phe Ser Leu Val Pro Leu Pro Leu Val Phe Val Glu Leu Ala Arg Ser
    50                  55                  60

Ala Ser Gly Leu Phe Asn Arg Tyr Lys Ile Gln Pro Lys Val Asn Tyr
65                  70                  75                  80

Ser Leu Ser Asp Met Phe Lys Cys Tyr Lys Asp Val Met Thr Met Phe
                85                  90                  95

Ile Leu Val Val Gly Pro Leu Gln Leu Val Ser Tyr Pro Ser Ile Gln
            100                 105                 110

Met Ile Glu Ile Arg Ser Gly Leu Pro Leu Pro Thr Ile Thr Glu Met
        115                 120                 125

Leu Ser Gln Leu Val Val Tyr Phe Leu Ile Glu Asp Tyr Thr Asn Tyr
    130                 135                 140

Trp Val His Arg Phe Phe His Ser Lys Trp Gly Tyr Asp Lys Ile His
145                 150                 155                 160

Arg Val His His Glu Tyr Thr Ala Pro Ile Gly Tyr Ala Ala Pro Tyr
                165                 170                 175

Ala His Trp Ala Glu Val Leu Leu Leu Gly Ile Pro Thr Phe Met Gly
            180                 185                 190

Pro Ala Ile Ala Pro Gly His Met Ile Thr Phe Trp Leu Trp Ile Ala
        195                 200                 205

Leu Arg Gln Met Glu Ala Ile Glu Thr His Ser Gly Tyr Asp Phe Pro
    210                 215                 220

Trp Ser Pro Thr Lys Tyr Ile Pro Phe Tyr Gly Gly Ala Glu Tyr His
225                 230                 235                 240

Asp Tyr His His Tyr Val Gly Gly Gln Ser Gln Ser Asn Phe Ala Ser
                245                 250                 255

Val Phe Thr Tyr Cys Asp Tyr Ile Tyr Gly Thr Asp Lys Gly Tyr Arg
            260                 265                 270

Phe Gln Lys Lys Leu Leu Glu Gln Ile Lys Glu Ser Ser Lys Lys Ser
        275                 280                 285

Asn Lys His Asn Gly Gly Ile Lys Ser Asp
    290                 295

<210> SEQ ID NO 8
<211> LENGTH: 297
<212> TYPE: PRT
<213> ORGANISM: Arabidopsis thaliana

<400> SEQUENCE: 8

Met Ile Pro Tyr Ala Thr Ile Glu Glu Ala Ser Ile Ala Leu Ser Arg
1               5                   10                  15

Asn Leu Thr Trp Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Ile
            35                  40                  45

Phe Ser Leu Val Pro Leu Pro Leu Val Phe Ile Glu Ser Ser Gln Ser
50                  55                  60

Thr Ser Asp Leu Phe Asn Arg Tyr Lys Ile Gln Pro Lys Val Lys Asn
65                  70                  75                  80

Ser Phe Ser Ser Met Phe Lys Cys Tyr Lys Asp Val Met Lys Met Phe
                85                  90                  95

Ile Leu Val Val Gly Pro Leu Gln Leu Val Ser Tyr Pro Ser Ile Gln
            100                 105                 110

Val Asp Phe Val Phe Arg Val Leu Lys Gln Met Ile Glu Ile Arg Ser
            115                 120                 125

Gly Leu Pro Leu Pro Ser Cys Met Glu Ile Val Ala Gln Leu Val Val
130                 135                 140

Tyr Phe Leu Val Glu Asp Tyr Thr Asn Tyr Trp Val His Arg Phe Phe
145                 150                 155                 160

His Cys Lys Trp Gly Tyr Glu Lys Phe His His Ile His Glu Tyr
                165                 170                 175

Thr Ala Pro Ile Gly Tyr Ala Ala Pro Tyr Ala His Trp Ala Glu Val
            180                 185                 190

Leu Leu Leu Gly Ile Pro Thr Phe Leu Gly Pro Ala Ile Ala Pro Gly
            195                 200                 205

His Met Ile Thr Phe Trp Leu Trp Ile Ala Leu Arg Gln Ile Glu Ala
            210                 215                 220

Ile Glu Thr His Ser Gly Tyr Asp Phe Pro Trp Ser Leu Thr Lys Tyr
225                 230                 235                 240

Ile Pro Phe Tyr Gly Gly Ala Glu Tyr His Asp Tyr His His Tyr Val
            245                 250                 255

Gly Gly Gln Ser Gln Ser Asn Phe Ala Ser Val Phe Thr Tyr Cys Asp
            260                 265                 270

Tyr Ile Tyr Gly Thr Asp Lys Gly Tyr Arg Phe Gln Lys Lys Leu Leu
            275                 280                 285

Gln Gln Val Asn Lys Tyr Ser Ile Asn
290                 295

<210> SEQ ID NO 9
<211> LENGTH: 291
<212> TYPE: PRT
<213> ORGANISM: Arabidopsis thaliana

<400> SEQUENCE: 9

Met Ile Pro Tyr Pro Thr Val Glu Asp Ala Ser Val Ala Leu Gly Arg
1               5                   10                  15

Asn Leu Thr Trp Phe Glu Thr Val Trp Phe Asp Tyr Ser Ala Thr Lys
            20                  25                  30

Ser Asn Phe His Val Tyr Cys His Thr Ile Leu Val Leu Phe Leu Val
            35                  40                  45

Phe Ser Leu Ala Pro Phe Pro Leu Val Ile Val Glu Trp Thr Gly Trp
50                  55                  60

Phe Asp Gln Phe Lys Ile Gln Lys Lys Val Lys Tyr Ser Leu Ser Asp

```
                65                  70                  75                  80
Met Phe Gln Cys Tyr Lys Glu Val Met Lys Leu Phe Leu Val Val
                    85                  90                  95
Gly Thr Leu Gln Ile Val Ser Tyr Pro Ser Ile Gln Met Val Gly Ile
                    100                 105                 110
Arg Ser Gly Leu Pro Leu Pro Ser Leu Met Glu Ile Val Ala Gln Leu
                    115                 120                 125
Val Val Tyr Phe Leu Ile Glu Asp Tyr Thr Asn Tyr Trp Ile His Arg
            130                 135                 140
Trp Met His Cys Lys Trp Gly Tyr Glu Lys Ile His Arg Ile His His
145                 150                 155                 160
Glu Tyr Thr Ser Pro Ile Gly Tyr Ala Ser Pro Tyr Ala His Trp Ala
                    165                 170                 175
Glu Ile Leu Ile Leu Gly Ile Pro Thr Phe Leu Gly Pro Ala Ile Ala
                    180                 185                 190
Pro Gly His Ile Met Thr Phe Trp Leu Trp Ile Ser Leu Arg Gln Phe
            195                 200                 205
Glu Ala Ile Glu Thr His Ser Gly Tyr Asp Phe Pro Trp Ser Val Thr
        210                 215                 220
Lys Leu Ile Pro Phe Tyr Gly Gly Pro Glu Tyr His Asp Tyr His His
225                 230                 235                 240
Tyr Val Gly Gly Gln Ser Gln Ser Asn Phe Ala Ser Val Phe Thr Tyr
                    245                 250                 255
Cys Asp Tyr Ile Tyr Gly Thr Asp Lys Gly Tyr Arg Ile His Lys Lys
                    260                 265                 270
Leu Leu His His Gln Ile Lys Glu Glu Ala Glu Glu Lys Arg Val Arg
            275                 280                 285
Lys His Asp
    290

<210> SEQ ID NO 10
<211> LENGTH: 299
<212> TYPE: PRT
<213> ORGANISM: Arabidopsis thaliana

<400> SEQUENCE: 10

Met Ile Pro Tyr Ala Thr Ile Glu Glu Ala Ser Ile Ala Leu Ser Arg
1               5                   10                  15
Asn Leu Thr Trp Leu Glu Thr Leu Trp Phe Asp Tyr Ser Ala Thr Lys
                20                  25                  30
Ser Asp Tyr Tyr Leu Tyr Cys His Asn Ile Leu Phe Leu Phe Leu Ile
            35                  40                  45
Phe Ser Leu Val Pro Leu Pro Leu Val Leu Ile Glu Ser Ala Gln Ser
        50                  55                  60
Thr Ser Asp Leu Phe Asn Arg Tyr Lys Ile Gln Pro Lys Val Lys Asn
65                  70                  75                  80
Ser Phe Ser Ser Met Leu Lys Cys Tyr Lys Asp Val Met Lys Met Phe
                85                  90                  95
Ile Leu Val Val Gly Pro Leu Gln Leu Val Ser Tyr Pro Ser Ile Gln
                    100                 105                 110
Met Ile Glu Ile Arg Ser Gly Leu Pro Leu Pro Ser Cys Met Glu Ile
            115                 120                 125
Val Ala Gln Phe Val Val Tyr Phe Leu Val Glu Asp Tyr Thr Asn Tyr
        130                 135                 140
```

```
Trp Val His Arg Phe Phe His Cys Lys Trp Gly Tyr Glu Lys Phe His
145                 150                 155                 160

His Ile His His Glu Tyr Thr Ala Pro Ile Gly Tyr Ala Ala Pro Tyr
                165                 170                 175

Ala His Trp Ala Glu Val Leu Leu Gly Ile Pro Thr Phe Leu Gly
        180                 185                 190

Pro Ala Ile Ala Pro Gly His Met Ile Thr Phe Trp Leu Trp Ile Ala
            195                 200                 205

Leu Arg Gln Ile Glu Ala Ile Glu Thr His Ser Gly Tyr Asp Phe Pro
        210                 215                 220

Trp Ser Leu Thr Lys Tyr Ile Pro Phe Tyr Gly Ala Glu Tyr His
225                 230                 235                 240

Asp Tyr His His Tyr Val Gly Gln Ser Gln Ser Asn Phe Ala Ser
                245                 250                 255

Val Phe Thr Tyr Cys Asp Tyr Ile Tyr Gly Thr Asp Lys Gly Tyr Arg
                260                 265                 270

Phe Gln Lys Lys Leu Leu Gln Gln Met Lys Glu Lys Ser Lys Lys Ser
            275                 280                 285

Asn Lys Leu Val Asn Gly Gly Glu Lys Phe Asp
        290                 295
```

```
<210> SEQ ID NO 11
<211> LENGTH: 298
<212> TYPE: PRT
<213> ORGANISM: Brassica napus

<400> SEQUENCE: 11
```

```
Met Ile Pro Tyr Ala Thr Ile Glu Glu Ala Ser Leu Ala Leu Gly Arg
1               5                   10                  15

Asn Leu Thr Thr Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Ile
        35                  40                  45

Phe Ser Leu Val Pro Leu Pro Leu Val Phe Val Glu Leu Ala Arg Ser
50                  55                  60

Ala Ser Gly Trp Phe Asp Arg Tyr Lys Ile Gln Pro Lys Val Lys Asn
65                  70                  75                  80

Ser Phe Ser Asp Met Phe Arg Cys Tyr Arg Asp Val Met Lys Met Phe
                85                  90                  95

Ile Leu Val Val Gly Pro Leu Gln Leu Val Ser Tyr Pro Ser Ile Gln
            100                 105                 110

Met Ile Glu Ile Arg Ser Gly Leu Pro Leu Pro Ser Phe Gly Glu Ile
        115                 120                 125

Ala Ala Gln Leu Val Val Tyr Phe Leu Val Glu Asp Tyr Thr Asn Tyr
    130                 135                 140

Trp Val His Arg Phe Phe His Ser Lys Trp Gly Tyr Glu Lys Ile His
145                 150                 155                 160

His Ile His His Glu Tyr Thr Ala Pro Ile Gly Tyr Ala Ala Pro Tyr
                165                 170                 175

Ala His Trp Ala Glu Val Leu Leu Gly Val Pro Thr Phe Leu Gly
        180                 185                 190

Pro Ala Ile Ala Pro Gly His Met Ile Thr Phe Trp Leu Trp Ile Ala
            195                 200                 205

Leu Arg Gln Ile Glu Ala Ile Glu Thr His Ser Gly Tyr Asp Phe Pro
        210                 215                 220
```

Trp Thr Leu Thr Lys Phe Ile Pro Phe Tyr Gly Gly Ala Glu Tyr His
225                 230                 235                 240

Asp Tyr His His Tyr Val Gly Gly Gln Ser Gln Ser Asn Phe Ala Ser
            245                 250                 255

Val Phe Thr Tyr Cys Asp Tyr Ile Tyr Gly Thr Asp Lys Gly Tyr Arg
            260                 265                 270

Phe Gln Lys Lys Phe Leu Gln Gln Ile Lys Gln Glu Ser Lys Lys Ser
            275                 280                 285

Asn Met Gln Asn Gly Gly Asp Lys Leu Asp
            290                 295

<210> SEQ ID NO 12
<211> LENGTH: 297
<212> TYPE: PRT
<213> ORGANISM: Glycine max

<400> SEQUENCE: 12

Met Leu Pro Tyr Ala Ser Ile Pro Glu Ala Val Ala Ala Leu Gly Arg
1               5                   10                  15

Asn Leu Thr Phe Ala Glu Thr Leu Trp Phe Asn Tyr Ser Ala Ala Lys
            20                  25                  30

Ser Asp Tyr Phe Leu Tyr Cys His Asn Ile Leu Phe Leu Phe Leu Val
            35                  40                  45

Phe Ser Leu Val Pro Leu Pro Leu Val Phe Leu Glu Phe Lys Arg Phe
        50                  55                  60

Ser Phe Val Ser Ser His Lys Ile Gln Pro Lys Val Arg Leu Ser Leu
65                  70                  75                  80

Ala Glu Thr Phe Lys Cys Tyr Lys Asp Val Met Arg Met Phe Phe Leu
                85                  90                  95

Val Val Gly Pro Leu Gln Leu Ile Ser Tyr Pro Ser Ile Gln Met Ile
            100                 105                 110

Gly Ile Arg Thr Gly Leu Pro Leu Pro Ser Trp Arg Glu Ile Leu Ser
            115                 120                 125

Gln Leu Leu Val Tyr Phe Leu Val Glu Asp Tyr Thr Asn Tyr Trp Ile
    130                 135                 140

His Arg Phe Leu His Asn Asp Trp Gly Tyr Glu Lys Ile His Arg Val
145                 150                 155                 160

His His Glu Tyr His Ala Pro Ile Gly Phe Ala Ala Pro Tyr Ala His
                165                 170                 175

Trp Ala Glu Ile Leu Ile Leu Gly Ile Pro Ser Phe Leu Gly Pro Ala
            180                 185                 190

Met Val Pro Gly His Ile Ile Thr Phe Trp Leu Trp Ile Ala Leu Arg
            195                 200                 205

Gln Ile Glu Ala Ile Asp Thr His Ser Gly Tyr Asp Phe Pro Arg Ser
    210                 215                 220

Ile Thr Lys Tyr Ile Pro Phe Tyr Gly Gly Ala Glu Tyr His Asp Tyr
225                 230                 235                 240

His His Tyr Val Gly Arg Gln Ser Gln Ser Asn Phe Ala Ser Val Phe
                245                 250                 255

Thr Tyr Cys Asp Tyr Ile Tyr Gly Thr Asp Lys Gly Tyr Arg Tyr Gln
            260                 265                 270

Lys Lys Ile Leu Gln Lys Leu Lys Glu Glu Leu Ala Asn Gly Val Glu
            275                 280                 285

Gln Asn Gly Gly Leu Tyr Lys Thr Asp

```
<210> SEQ ID NO 13
<211> LENGTH: 254
<212> TYPE: PRT
<213> ORGANISM: Glycine max
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid

<400> SEQUENCE: 13

Met Leu Pro Tyr His Thr Leu Glu Gly Ala Gln Val Ala Leu Gly Arg
1               5                   10                  15

Gly Leu Thr Leu Ala Glu Thr Ile Trp Phe Lys Tyr Ser Ala Asn Lys
            20                  25                  30

Pro Asp Phe Val Leu His Cys His Asn Thr Leu Phe Leu Cys Leu Phe
        35                  40                  45

Tyr Ser Ile Ala Pro Ile Pro Phe Val Leu Met Glu Leu Ser Gly Tyr
    50                  55                  60

Glu Lys Leu Asn Lys His Lys Ile Gln Pro Ser Val Lys Arg Ser Phe
65                  70                  75                  80

Lys Glu Met Phe Lys Cys Tyr Lys Asp Val Met Glu Thr Phe Val Ile
                85                  90                  95

Ala Val Ser Pro Leu Gln Ile Ile Ser Tyr Pro Thr Ile Lys Trp Ile
            100                 105                 110

Gly Ile Arg Thr Gly Leu Ser Leu Pro Ser Gly Trp Glu Leu Phe Trp
        115                 120                 125

Gln Leu Phe Ile Tyr Phe Val Ile Glu Asp Phe Ser Asn Tyr Trp Ile
    130                 135                 140

His Arg Met Leu His Cys Lys Trp Ala Phe Glu Lys Ile His Lys Val
145                 150                 155                 160

His His Glu Tyr Val Ala Pro Ile Gly Leu Ser Ala Pro Tyr Ala His
                165                 170                 175

Trp Ala Glu Ile Ile Ile Leu Gly Ile Pro Xaa Phe Leu Gly Pro Ala
            180                 185                 190

Leu Val Pro Gly His Ile Thr Thr Tyr Trp Leu Trp Phe Ile Leu Arg
        195                 200                 205

Gln Leu Glu Ala Ile Glu Thr His Ser Gly Tyr Asp Phe Ser Trp Glu
    210                 215                 220

Xaa Thr Lys Tyr Ile Pro Phe Tyr Gly Pro Ala Tyr His Asp Tyr
225                 230                 235                 240

His His Tyr Val Gly Gly Lys Ser Gln Ser Asn Phe Ala Ser
                245                 250

<210> SEQ ID NO 14
<211> LENGTH: 305
<212> TYPE: PRT
<213> ORGANISM: Hordeum vulgare

<400> SEQUENCE: 14

Met Leu Pro Trp Ala Thr Ala Ala Glu Ala Glu Ala Ala Leu Gly Arg
1               5                   10                  15

Pro Met Thr Pro Ala Glu Ala Leu Trp Phe Arg Trp Thr Ala Gly Thr
            20                  25                  30
```

```
Pro Asp Tyr Gly Leu Tyr Cys Leu Asn Ile Leu Phe Leu Leu Leu Val
            35                  40                  45

Phe Thr Leu Ala Pro Leu Pro Val Ala Leu Glu Leu Arg Ala Pro
     50                  55                  60

Arg Ala Val Gly Pro Tyr Lys Leu Gln Pro Arg Val Arg Leu Ser Arg
 65                  70                  75                  80

Ala Asp Phe Leu Lys Cys Tyr Gly Asp Val Met Arg Ile Phe Phe Leu
                 85                  90                  95

Val Ile Gly Pro Leu Gln Leu Val Ser Tyr Pro Ala Val Lys Met Val
                100                 105                 110

Gly Ile His Thr Gly Leu Pro Leu Pro Ser Leu Gly Glu Met Ala Ala
             115                 120                 125

Gln Leu Val Val Tyr Phe Leu Val Glu Asp Tyr Leu Asn Tyr Trp Ile
         130                 135                 140

His Arg Leu Leu His Gly Glu Trp Gly Tyr Glu Lys Ile His Arg Ile
145                 150                 155                 160

His His Glu Tyr Thr Ala Pro Ile Gly Phe Ala Ala Pro Tyr Ala His
                 165                 170                 175

Trp Ala Glu Val Leu Ile Leu Gly Ile Pro Ser Phe Ala Gly Pro Ala
                 180                 185                 190

Ile Ala Pro Gly His Met Ile Thr Phe Trp Leu Trp Ile Ile Leu Arg
             195                 200                 205

Gln Met Glu Ala Ile Asp Thr His Ser Gly Phe Asp Phe Pro Phe Ser
         210                 215                 220

Leu Thr Lys Tyr Ile Pro Phe Tyr Gly Gly Ala Glu Ser His Asp Tyr
225                 230                 235                 240

His His Tyr Val Gly Gly Gln Ser Gln Ser Ile Phe Ala Ser Val Phe
                 245                 250                 255

Thr Tyr Cys Asp Pro Leu Cys Gly Thr Asp Arg Gly Tyr Arg Phe His
                 260                 265                 270

Arg Ala Ser Leu Pro Met Leu Arg Ala Leu Ala Pro Pro Ala Ala Lys
             275                 280                 285

Lys Asp Ala Pro Met Gly Phe Ser Ser Ala Lys Gly Asp Tyr Val Val
         290                 295                 300

Leu
305

<210> SEQ ID NO 15
<211> LENGTH: 301
<212> TYPE: PRT
<213> ORGANISM: Oryza sativa

<400> SEQUENCE: 15

Met Leu Pro Tyr Ala Thr Ala Ala Glu Ala Glu Ala Ala Leu Gly Arg
 1               5                  10                  15

Ala Met Thr Ala Ala Glu Ser Leu Trp Phe Arg Tyr Ser Ala Gly Ile
             20                  25                  30

Pro Asp Tyr Val Leu Phe Trp His Asn Ile Leu Phe Leu Phe Val Val
             35                  40                  45

Phe Thr Leu Ala Pro Leu Pro Val Ala Leu Leu Glu Leu Arg Ala Pro
     50                  55                  60

Ala Ala Val Gly Pro Phe Lys Leu Gln Pro Lys Val Arg Leu Ser Arg
 65                  70                  75                  80

Glu Glu Phe Phe Arg Cys Tyr Arg Asp Val Met Arg Leu Phe Phe Leu
```

```
                    85                  90                  95
Val Ile Gly Pro Leu Gln Leu Val Ser Tyr Pro Thr Val Lys Met Val
                100                 105                 110

Gly Ile His Thr Gly Leu Pro Leu Pro Ser Leu Gly Glu Met Ala Ala
            115                 120                 125

Gln Leu Leu Val Tyr Phe Leu Val Glu Asp Tyr Leu Asn Tyr Trp Ile
        130                 135                 140

His Arg Leu Leu His Gly Glu Trp Gly Tyr Glu Lys Ile His Arg Val
145                 150                 155                 160

His His Glu Phe Thr Ala Pro Ile Gly Phe Ala Ala Pro Tyr Ala His
                165                 170                 175

Trp Ala Glu Val Leu Ile Leu Gly Ile Pro Ser Phe Val Gly Pro Ala
                180                 185                 190

Leu Ala Pro Gly His Met Ile Thr Phe Trp Leu Trp Ile Val Leu Arg
            195                 200                 205

Gln Met Glu Ala Ile Glu Thr His Ser Gly Phe Asp Phe Pro Phe Asn
        210                 215                 220

Leu Thr Lys Tyr Ile Pro Phe Tyr Gly Gly Ala Glu Tyr His Asp Tyr
225                 230                 235                 240

His His Tyr Val Gly Arg Gln Ser Gln Ser Asn Phe Ala Ser Val Phe
                245                 250                 255

Thr Tyr Cys Asp Tyr Leu Tyr Gly Thr Asp Lys Gly Tyr Arg Tyr His
                260                 265                 270

Lys Ala Tyr Gln Ala Lys Met Lys Ala Leu Gly Gln Thr Glu Gly Glu
            275                 280                 285

Lys Ala Asp Ser Asn Gly Leu Ser Tyr Ala Lys Leu Asp
        290                 295                 300

<210> SEQ ID NO 16
<211> LENGTH: 301
<212> TYPE: PRT
<213> ORGANISM: Triticum sp.

<400> SEQUENCE: 16

Met Leu Pro Trp Ala Thr Ala Ala Glu Ala Glu Ala Ala Leu Glu Arg
1               5                   10                  15

Ala Met Thr Ala Ala Glu Ala Leu Trp Phe Arg Trp Thr Ala Glu Ala
                20                  25                  30

Ser Asp Tyr Tyr Leu Tyr Cys Leu Asn Ile Leu Phe Leu Leu Val Val
            35                  40                  45

Phe Thr Leu Ala Pro Leu Pro Val Ala Leu Leu Glu Leu Arg Ala Pro
        50                  55                  60

Arg Ala Val Gly Pro Tyr Lys Leu Gln Pro Arg Val Arg Leu Ser Arg
65                  70                  75                  80

Ala Glu Phe Ile Lys Cys Tyr Gly Asp Val Met Arg Ile Phe Phe Leu
                85                  90                  95

Val Ile Gly Pro Leu Gln Leu Val Ser Tyr Pro Ala Val Lys Met Val
                100                 105                 110

Gly Ile His Thr Gly Leu Pro Leu Pro Ser Leu Gly Glu Met Ala Ala
            115                 120                 125

Gln Leu Leu Val Tyr Phe Leu Val Glu Asp Tyr Leu Asn Tyr Trp Ile
        130                 135                 140

His Arg Leu Leu His Gly Glu Trp Gly Tyr Glu Lys Ile His Arg Ile
145                 150                 155                 160
```

-continued

```
His His Glu Tyr Thr Ala Pro Ile Gly Phe Ala Ala Pro Tyr Ala His
                165                 170                 175

Trp Ala Glu Val Leu Ile Leu Gly Ile Pro Ser Phe Ala Gly Pro Ala
            180                 185                 190

Ile Ala Pro Gly His Met Ile Thr Phe Trp Leu Trp Ile Ile Leu Arg
        195                 200                 205

Gln Met Glu Ala Ile Asp Thr His Ser Gly Phe Asp Phe Pro Phe Ser
210                 215                 220

Leu Thr Lys Tyr Ile Pro Phe Tyr Gly Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Leu Tyr Gly Thr Asp Arg Gly Tyr Arg Phe His
            260                 265                 270

Lys Ala Tyr Leu Ala Lys Leu Lys Asp Leu Ala Pro Ser Asp Gly Glu
        275                 280                 285

Lys Glu Gly Ala Asp Gly Phe Ala Tyr Ala Lys Leu Asp
290                 295                 300

<210> SEQ ID NO 17
<211> LENGTH: 37
<212> TYPE: PRT
<213> ORGANISM: Artificial
<220> FEATURE:
<223> OTHER INFORMATION: consensus of SEQ ID NOS:1-4
<220> FEATURE:
<221> NAME/KEY: misc_feature
<222> LOCATION: (2)..(2)
<223> OTHER INFORMATION: Xaa can be Leu or Ile or Met
<220> FEATURE:
<221> NAME/KEY: misc_feature
<222> LOCATION: (5)..(5)
<223> OTHER INFORMATION: Xaa can be Ala or Gly
<220> FEATURE:
<221> NAME/KEY: misc_feature
<222> LOCATION: (7)..(7)
<223> OTHER INFORMATION: Xaa can be Thr or Ala
<220> FEATURE:
<221> NAME/KEY: misc_feature
<222> LOCATION: (8)..(8)
<223> OTHER INFORMATION: Xaa can be Gly or Ala
<220> FEATURE:
<221> NAME/KEY: misc_feature
<222> LOCATION: (9)..(9)
<223> OTHER INFORMATION: Xaa can be Asp or Glu
<220> FEATURE:
<221> NAME/KEY: misc_feature
<222> LOCATION: (12)..(12)
<223> OTHER INFORMATION: Xaa can be Ala or Gly
<220> FEATURE:
<221> NAME/KEY: misc_feature
<222> LOCATION: (14)..(14)
<223> OTHER INFORMATION: Xaa can be Leu or Val
<220> FEATURE:
<221> NAME/KEY: misc_feature
<222> LOCATION: (17)..(17)
<223> OTHER INFORMATION: Xaa can be Ala or Thr or Ser or Gly
<220> FEATURE:
<221> NAME/KEY: misc_feature
<222> LOCATION: (18)..(18)
<223> OTHER INFORMATION: Xaa can be Leu or Met
<220> FEATURE:
<221> NAME/KEY: misc_feature
<222> LOCATION: (23)..(23)
<223> OTHER INFORMATION: Xaa can be Ala or Thr
<220> FEATURE:
<221> NAME/KEY: misc_feature
<222> LOCATION: (24)..(24)
<223> OTHER INFORMATION: Xaa can be Ala or Leu
<220> FEATURE:
```

```
<221> NAME/KEY: misc_feature
<222> LOCATION: (26)..(26)
<223> OTHER INFORMATION: Xaa can be Tyr or Phe
<220> FEATURE:
<221> NAME/KEY: misc_feature
<222> LOCATION: (27)..(27)
<223> OTHER INFORMATION: Xaa can be Arg or Glu
<220> FEATURE:
<221> NAME/KEY: misc_feature
<222> LOCATION: (31)..(31)
<223> OTHER INFORMATION: Xaa can be Ser or Val or Gly or Ala
<220> FEATURE:
<221> NAME/KEY: misc_feature
<222> LOCATION: (32)..(32)
<223> OTHER INFORMATION: Xaa can be Val or Met or Ile
<220> FEATURE:
<221> NAME/KEY: misc_feature
<222> LOCATION: (35)..(35)
<223> OTHER INFORMATION: Xaa can be Arg or Ser or Leu or Tyr
<220> FEATURE:
<221> NAME/KEY: misc_feature
<222> LOCATION: (36)..(36)
<223> OTHER INFORMATION: Xaa can be Tyr or Trp or Cys

<400> SEQUENCE: 17

Met Xaa Pro Tyr Xaa Thr Xaa Xaa Xaa Ala Glu Xaa Ala Xaa Gly Arg
1               5                   10                  15

Xaa Xaa Thr Trp Ala Glu Xaa Xaa Trp Xaa Xaa Tyr Ser Ala Xaa Xaa
            20                  25                  30

Pro Asp Xaa Xaa Leu
        35

<210> SEQ ID NO 18
<211> LENGTH: 30
<212> TYPE: PRT
<213> ORGANISM: Artificial
<220> FEATURE:
<223> OTHER INFORMATION: Consensus of SEQ ID NOS:1-16 with X defined
<220> FEATURE:
<221> NAME/KEY: MISC_FEATURE
<222> LOCATION: (2)..(2)
<223> OTHER INFORMATION: Xaa can be Ile or Met or Leu
<220> FEATURE:
<221> NAME/KEY: MISC_FEATURE
<222> LOCATION: (4)..(4)
<223> OTHER INFORMATION: Xaa can be Tyr or Trp
<220> FEATURE:
<221> NAME/KEY: MISC_FEATURE
<222> LOCATION: (5)..(5)
<223> OTHER INFORMATION: Xaa can be Ala or Gly or Pro or His
<220> FEATURE:
<221> NAME/KEY: MISC_FEATURE
<222> LOCATION: (6)..(6)
<223> OTHER INFORMATION: Xaa can be Thr or Ser
<220> FEATURE:
<221> NAME/KEY: MISC_FEATURE
<222> LOCATION: (7)..(7)
<223> OTHER INFORMATION: Xaa can be Ala or Thr or Leu or Val or Ile
<220> FEATURE:
<221> NAME/KEY: MISC_FEATURE
<222> LOCATION: (8)..(8)
<223> OTHER INFORMATION: Xaa can be Ala or Gly or Thr or Glu or Pro
<220> FEATURE:
<221> NAME/KEY: MISC_FEATURE
<222> LOCATION: (9)..(9)
<223> OTHER INFORMATION: Xaa can be Glu or Asp or Ala or Gly
<220> FEATURE:
<221> NAME/KEY: MISC_FEATURE
<222> LOCATION: (11)..(11)
<223> OTHER INFORMATION: Xaa can be Ser or Glu or Val or Gln
<220> FEATURE:
<221> NAME/KEY: MISC_FEATURE
<222> LOCATION: (12)..(12)
<223> OTHER INFORMATION: Xaa can be Gly or Ala or Ile or Val or Leu
<220> FEATURE:
```

```
<221> NAME/KEY: MISC_FEATURE
<222> LOCATION: (14)..(14)
<223> OTHER INFORMATION: Xaa can be Val or Leu
<220> FEATURE:
<221> NAME/KEY: MISC_FEATURE
<222> LOCATION: (15)..(15)
<223> OTHER INFORMATION: Xaa can be Gly or Asn or Ser or Glu
<220> FEATURE:
<221> NAME/KEY: MISC_FEATURE
<222> LOCATION: (17)..(17)
<223> OTHER INFORMATION: Xaa can be Thr or Ser or Gly or Ala or Pro or
      Asn
<220> FEATURE:
<221> NAME/KEY: MISC_FEATURE
<222> LOCATION: (18)..(18)
<223> OTHER INFORMATION: Xaa can be Met or Leu
<220> FEATURE:
<221> NAME/KEY: MISC_FEATURE
<222> LOCATION: (20)..(20)
<223> OTHER INFORMATION: Xaa can be Trp or Pro or Tyr or Arg or Thr or
      Phe or Leu or Ala
<220> FEATURE:
<221> NAME/KEY: MISC_FEATURE
<222> LOCATION: (21)..(21)
<223> OTHER INFORMATION: Xaa can be Ala or Leu or Phe
<220> FEATURE:
<221> NAME/KEY: MISC_FEATURE
<222> LOCATION: (23)..(23)
<223> OTHER INFORMATION: Xaa can be Thr or Ala or Ser
<220> FEATURE:
<221> NAME/KEY: MISC_FEATURE
<222> LOCATION: (24)..(24)
<223> OTHER INFORMATION: Xaa can be Ala or Leu or Ile or Val
<220> FEATURE:
<221> NAME/KEY: MISC_FEATURE
<222> LOCATION: (26)..(26)
<223> OTHER INFORMATION: Xaa can be Tyr or Phe or Leu
<220> FEATURE:
<221> NAME/KEY: MISC_FEATURE
<222> LOCATION: (27)..(27)
<223> OTHER INFORMATION: Xaa can be Glu or Arg or Asn or Asp or Lys
<220> FEATURE:
<221> NAME/KEY: MISC_FEATURE
<222> LOCATION: (28)..(28)
<223> OTHER INFORMATION: Xaa can be Trp or Tyr
<220> FEATURE:
<221> NAME/KEY: MISC_FEATURE
<222> LOCATION: (29)..(29)
<223> OTHER INFORMATION: Xaa can be Ser or Thr

<400> SEQUENCE: 18

Met Xaa Pro Xaa Xaa Xaa Xaa Xaa Xaa Ala Xaa Xaa Ala Xaa Xaa Arg
1               5                   10                  15

Xaa Xaa Thr Xaa Xaa Glu Xaa Xaa Trp Xaa Xaa Xaa Xaa Ala
            20                  25                  30

<210> SEQ ID NO 19
<211> LENGTH: 921
<212> TYPE: DNA
<213> ORGANISM: Zea mays

<400> SEQUENCE: 19
atgatcccct acgcgactgc ggcggaggcg gagggagcac tggggcgcac catgacgtgg      60
gctgagacag catggtacga gtactcggcg gtgatgccag attcctggct gcactgccac     120
accacattta tcctgttcgt catctacagc atcgccccgc tgcccctgct actcctagag     180
cagttcgctc cgtccgtcgt gctgccgtac aagctgcagc ccggtacg gctgccccg        240 gcagcctccc tcagctgcta catggacgcg gcctgcatct ttccgctcgc cgttggcctt     300
cagttcgtct cctatcctgc ggtcgccaag atactaagga cccgaatggg actgccgttg     360
ccgtcggtga gggagaccat cgcgcagcta gtcgtatact ctctagtgga ggattacctc     420
```

-continued

```
agctactgga tgcaccgtct gctgcacacc cagtggtgct acgagaagat ccaccgcgtc      480
caccacgagt tcacggctcc tacaggcttc gccatgtcgt acagccactg ggccgagaac      540
gtcgtccttt ctatcccggc cttggccggc ccagtgctcg tgccatgcca tgtcaccacg      600
cagtggctat ggttctccat ccgcctaatt gagggcatta acacgcacag cggttaccat      660
ttcccgttca gcccttgcag gctgattcca ttctacggag gggctgcata ccatgactac      720
catcactatg caggaggccg tagccaaagc aactttgcac ccctgttcac ctactgtgat      780
tatttatata ggacagacaa aggctacaga taccacaagc taaagcaaga gaagctgaag      840
agtctagcag aaaatagtgc ggataaagga ggcaactact cattcgacga agggaaaaag      900
aacagatatt tttgtgcctg a                                                921

<210> SEQ ID NO 20
<211> LENGTH: 882
<212> TYPE: DNA
<213> ORGANISM: Zea mays

<400> SEQUENCE: 20
atgatgccct acggcacggc ggcggaggca gaggcggcgc tggggcgctc catgacctgg       60
gcagaggccc tgtggttccg gtactcagcg gggatgccgg acctgtgtct gacgtggcac      120
gtctccctcg tctacctcgt cttgtacgcg ttggttccgc tgccggtcat ggttatccag      180
aagctcgcgc cggggtacgc cctgcggcac aagctgcagc ccggggtgcc ggagccctcg      240
ccggtttcca cctacgtcga atacataagg acagcaggg gcgtcaccct ggccgccttg      300
ggcccgttcc cgctcatcta ctccatcgca ttcaagctgt tcggggtccg gacgggactc      360
cctttgccgt cggtctggga gactgcgacg cacctggcgg tgtattcgct ggtggaggac      420
tacacgtcgt actggctcca ccgcttcctg cacaccaggt gggggtacga aagatccac      480
cgcgtccacc acgagaagac ggcgccgtcc gggttcgccg ccgcctacgc cacgggcact      540
gagctcagct tgtacctcac cacgctcttc cttgggccgg cgatcgtgcc cagccacgtc      600
accacgcact ggctcttgtt ctccatccgc ataatggagg ccttcgacac acacagcggg      660
taccacttcc cgttcagcct cgcgaggttc atcccgttct acggtggcgc ggaattccac      720
gactaccatc actacgccgg agagaagacc aggagcaatt tcagttccgt gttcacgtac      780
tgtgattata tatgggac aaacaaaggc tacatgtacc acaagagaag cctagccgag      840
ctgaagacga aggaggccga acacagcggg aaagaagact ga                         882

<210> SEQ ID NO 21
<211> LENGTH: 855
<212> TYPE: DNA
<213> ORGANISM: Oryza sativa

<400> SEQUENCE: 21
atgctcccgt acgcgacggc ggcggaggcg gaggcggcgg tggggcgggg cctgacgtgg       60
gcggaggcgg cctggttccg ctactcggcg gccatcccgg actactgcct ctactgccac      120
acgtcccca tcctcctcct cgtctacacc ctcgcgccgc tccccctcgc gctgctcgag      180
ctccgccgcc acctgccgct gccgcacaag ctgcagcccg cgtgcgcca cccgccggcc      240
gccttcctcc ggtgctacgc tgccaccgcg cgcgtgctgc tcctgccgt cgggccggtc      300
cagctgcgcgt cgttccctgc ggtgagggcg tggggatac ggacggggct gccgctgccg      360
tcggcggggg agacggcggc gcaggtggcg gtgtacctgc tggtggagga ctacctgggc      420
```

```
tactggatcc accgcctgct gcacacgccg tgggcctacc accacatcca ccgagtccac    480
cacgagttca ccgcgcccat gggctacgcc gccccgtacg cccactgggc cgagatcctc    540
atcctcggct tcccggcctt cgccggccca gccatcgtgc cgtgccacat gaccaccttc    600
tggctctggt tcgtgcttcg ccacctcgag gccatccaca tccacagcgg gttcaagttg    660
ccgttcgatc cgaccaagta tatcccgttg tatggaggag tggagtacca tgactaccac    720
catttcgtgg gaggacacag ccagagcaac ttctcttctg tcttcacttt ctgtgattac    780
atctacggga ctgacagagg ctacagatac cataaggcaa gcttgtcaaa gatgagaata    840
tttgttagag cttag                                                    855

<210> SEQ ID NO 22
<211> LENGTH: 907
<212> TYPE: DNA
<213> ORGANISM: Hordeum vulgare

<400> SEQUENCE: 22
atgctgccgt acgcgacgac cggcgatgcg gaggcggcgc tcggccgcgc cctgacgtgg     60
gcggaggccg cgtggctccg ctactcggcg tccgtgccgg accgctacct ccactggccc    120
aacatcgcca tcacattggt cgtctacacg ctggcgccgc tgccgctcgc cctcttcgac    180
ctcgccgccc cggccgtcgc cgcgccgtac aagctgcagc ccaaggtgca gcacccgccc    240
gccaccttct ccgctgcta catggacgcc gttcgggtct cgctgctcat catcgggcca    300
taccagctca tctcctatcc cgccgcaaag ataatggaca tacggacggg acttccattg    360
ccgtcaatgg gggaaatagc agcgcaactg acggtatact tcttggtgga agactatctg    420
aactactggc tccatcggct gttgcacacc aaatggtgct atgaaaagat ccaccatgtt    480
caccatgagt tcacggcgcc catggcctat gccgcatggt atggacactg gctgagatg    540 ctcatccttg cggggcccct ccttggccgg ccctgcactc gtccatgcc atgttaccac    600 gctctggatc tggtttgcag cacgtttggt tgagagcctc aacatacata gcggatttaa    660
gttgccattc aacgctgaga agtacatacc attctacgga ggggcagagc accatgacta    720
ccatcactac ataggaggac agagcaagag caacttcgcc cctgttttca cctactgtga    780
ttacatatac ggaacggata aaggctacag atatcacaag gcaaccctgg caaagctgaa    840
ggagttggca ggaaacgagg ttcagaaagg agtcgacaac ggattcaaca gcggaaagca    900
ggagtag                                                             907

<210> SEQ ID NO 23
<211> LENGTH: 906
<212> TYPE: DNA
<213> ORGANISM: Zea mays

<400> SEQUENCE: 23
atgctgccct acgcgacggc ggcggaggcg gaggcggcgc ttggccggcc catgacgccc     60
gccgaggcgc tgtggttccg gtacaccgcg ggggtgtccg actaccacct ctactgctgc    120
aacatcctct cctccttcgt cgtcttcacg gtggcccgc ttcccatcgc gctcctcgag    180
ctccgggccc cggccgcggt ctcgccgtac aaactgcagc cgcgggtgcg gctctccagg    240
gccgagttcg tccggtgcta caaggacgtc ctccgcatct tcttcctcgt catcggcccg    300
ctccagctcg tctcctaccc ggcggtcaag tttgtgggaa ttcacacgaa gttgcctttg    360
ccgtcccttg cggagttggc agcacagcta ctggtgtact tccttgttga ggactacctc    420
aattactgga tccacaggtt tctccacggg gagtgggggt accagaatat ccaccgtgtt    480
```

```
caccatgagt tcactgcgcc aataggattc gcagctccat atgcacactg ggctgaggtg      540
ctgatactcg gcatcccctc cttcgtcggg ccagccattg ttccaggcca catgatcaca      600
ttctggctct ggattatact ccgtcaggtg gaggctatcg agacacatag cggctttgat      660
ttcccattca ccccgacaaa gtatattcca ttctatggag gagcagaata ccatgactat      720
catcattatg taggaggcca gagccaaagc aattttgctt ctgttttcac ttactgtgat      780
tacttatatg gcactgacaa aggttacaga ttccacaaaa catacctagc aaagctgaag      840
gatctggggc ataatgatgg ccagaaagga gacggcagcg acccagcta tgtgaaactg      900 gattag                                                                906

<210> SEQ ID NO 24
<211> LENGTH: 900
<212> TYPE: DNA
<213> ORGANISM: Allium porrum

<400> SEQUENCE: 24
atgatcccct atccatctct gacagctgca gaagcggccc tgaaccgtcc gctaacctac       60
gccgaaacca tttggttcaa ttactccgcc acaataccg atccgttgct gtattaccac      120
aatacgattt tccttttttgt tattttcacg ctagtacctc tccctttggc tcttctcgag      180
ctctattggc cgtctgtttt gaagccgttc aagatccagc cgaaggtgta cctgtcgaaa      240
tctgagtttt tggaatgtta taagaatgtc attaaggttt tcttcttagt tgtttgcccg      300
cttcagcttc tgtcgtatcc tactgttaag ttcgtgggaa taaggactgg gctaccatta      360
ccatcagtat gggaagttgc atctcaatta gcagtgtact tcttgttgga ggattttgga      420
aattattgga ttcacagatg gctacatgga aaatgggggt acgagaagat tcacaaagtt      480
catcatgaat atactgcacc aataggtttt gctgctcctt acgcccattg ggctgaggtg      540
ttgatccttg gtattccatc gtttcttgga cctgctattg ttcctggaca catgattact      600
ctttggttat ggatagctct gaggcaaatt gaggcactgg ataccatag cgggtacgac      660 ttcccctttga gttttaccaa gttcattcct ttctatggag gcgctgaata tcatgattat      720
catcattatg ttggagggca aagccagagc aatttcgctt ctgtgtttac gtattgtgac      780
tacgtatatg gaactgacaa gggttacagg tatcgaaagg catgcctctc gatgatgaag      840
gaagaatcgg aaaaccaaaa cggagttgag aattcttttc agaaccagaa atctgattga      900

<210> SEQ ID NO 25
<211> LENGTH: 897
<212> TYPE: DNA
<213> ORGANISM: Arabidopsis thaliana

<400> SEQUENCE: 25
atgattcctt acgctacagt cgaagaagct tcaatcgcac tgggacgaaa cctcacacgt       60
ctcgaaactc tatggttcga ttactccgcc acgaagtccg attactatct ctactgtcac      120
aacattttgt tcttgttcct cgtcttctct ctcgttcctc tccctctcgt tttcgtcgaa      180
ttggctcgat ctgcttctgg tttgtttaat cggtataaga tccagcctaa ggttaattac      240
tctttatctg atatgttcaa atgttacaaa gacgtcatga cgatgtttat cctcgtcgtt      300
ggtccattgc aactcgtttc ttatccttcg attcagatga ttgagatacg atctggatta      360
ccattaccaa caattacaga gatgctgtca cagttagtag tctacttctt gatagaagac      420
tacactaact actgggtaca tagattcttt catagtaaat ggggatacga taagattcat      480
```

| | |
|---|---|
| cgagttcatc acgagtacac agctcctata ggatatgctg ctccttatgc acattgggct | 540 |
| gaagttttgc ttctcggaat cccgacgttt atgggaccag ctattgctcc tggtcatatg | 600 |
| ataaccttt ggttgtggat tgctttaagg caaatggaag ctattgagac tcacagtgga | 660 |
| tatgattttc catggagtcc aacaaaatac atcccttct acggtggtgc tgagtaccat | 720 |
| gactatcatc actacgttgg aggacaaagt caaagcaact tcgcttcagt gttcacgtac | 780 |
| tgtgattaca tttatggaac tgacaagggt tacagattcc aaaagaagct tcttgagcag | 840 |
| atcaaggagt cgtcgaagaa gagcaacaag cataacggag gaataaaatc cgattag | 897 |

<210> SEQ ID NO 26
<211> LENGTH: 894
<212> TYPE: DNA
<213> ORGANISM: Arabidopsis thaliana

<400> SEQUENCE: 26

| | |
|---|---|
| atgatcccat acgcaacaat cgaagaagcg tcgatcgcat tatctcgaaa cctcacatgg | 60 |
| ctagagactc tctggttcga ttactccgcc accaaatccg attactacct ctactgccac | 120 |
| aacattctct tcctcttcct catcttctct ctcgttcctc tccctctcgt tttcatcgaa | 180 |
| tcatctcaat ccacctcaga tttgttcaat cgctacaaaa tccaaccaaa agtgaaaaac | 240 |
| tcattctcat cgatgttcaa atgttacaaa gacgtcatga agatgttcat cctcgtcgtt | 300 |
| ggtccattac aactcgtttc ttatccttcg attcaggttg attttgtttt tcgtgtgttg | 360 |
| aaacagatga ttgagatacg aagtggatta ccattaccat catgtatgga gattgtagca | 420 |
| cagttagtgg tttacttctt ggtagaggat tatactaatt actgggttca tagattcttt | 480 |
| cattgtaaat ggggttatga aagtttcat catattcatc atgagtatac agctcctatt | 540 |
| ggttatgctg ctccttatgc tcattgggct gaggttttgc ttcttggcat tcccacgttt | 600 |
| cttggacctg ctattgctcc tggtcatatg attaccttt ggttgtggat tgctttacga | 660 |
| cagattgagg ctatcgaaac tcatagcgga tatgatttcc catggtctct gacaaagtac | 720 |
| attccatttt atggtggagc tgagtatcat gattaccatc actacgttgg aggacaaagc | 780 |
| cagagtaact ttgcttcagt ttttacttac tgcgattaca tctatggaac tgataaaggt | 840 |
| taccgattcc agaagaagct tcttcagcag gtaaataaat actccataaa ctga | 894 |

<210> SEQ ID NO 27
<211> LENGTH: 876
<212> TYPE: DNA
<213> ORGANISM: Arabidopsis thaliana

<400> SEQUENCE: 27

| | |
|---|---|
| atgatccctt atccaaccgt agaagatgcg tccgtggcgt taggacgaaa ccttacttgg | 60 |
| ttcgagacgg tttggttcga ttactcagcc accaaatcca atttccatgt atattgccac | 120 |
| accattctgt ttctcttcct tgtcttttca ctagctcctt ttcctcttgt gattgtcgaa | 180 |
| tggaccggtt ggttcgatca gtttaagatt cagaagaagg ttaagtattc gttgtctgat | 240 |
| atgttccaat gttataaaga agtcatgaag ttgttccttc tcgtcgtcgg cacattgcaa | 300 |
| atcgtttctt atccttccat ccagatggtt gggattcgaa gtggtttgcc attaccatcg | 360 |
| ttaatggaga tagtagcaca attagtggtt tacttcttga tagaagatta cactaactac | 420 |
| tggatccata gatggatgca ttgcaaatgg ggttacgaga agattcatcg aatccatcat | 480 |
| gagtacacat cacctatcgg atacgcatcg ccgtatgcgc attgggccga gatttttgatt | 540 |
| cttgggattc cgacgtttct tggaccggca attgctcctg gccatataat gacgttttgg | 600 |

```
ttatggatat ctttacgaca attcgaggcg attgagaccc acagcggata tgattttcca      660
tggagtgtga caaaattaat tccattttac ggtggacctg agtatcatga ctaccatcac      720
tacgttggag acaaagcca gagcaacttt gcttcggttt tcacttactg cgattacatt      780
tatggaactg ataaaggcta tcgaatccat aagaagcttc ttcatcatca gattaaagag      840
gaagctgaag agaagagagt aaggaaacac gattag                                876

<210> SEQ ID NO 28
<211> LENGTH: 900
<212> TYPE: DNA
<213> ORGANISM: Arabidopsis thaliana

<400> SEQUENCE: 28
atgatcccat acgcaacaat cgaagaagcg tcgatcgcat tatctcgaaa cctcacatgg       60
ctagagactc tctggttcga ttactccgcc accaaatccg attactacct ctactgccac      120
aacattctct tcctcttcct catcttctct ctcgttcctc ccctctcgt tctcatcgaa       180 tcagctcaat ccacctcaga tttgttcaat cgctacaaaa tccaaccaaa agtgaaaaac      240
tcgttctcat cgatgttgaa atgttacaaa gacgtcatga agatgttcat cctcgtcgtt      300
ggtccattac aactcgtttc ttatccttcg attcagatga ttgagatacg aagtggatta      360
ccattaccat catgtatgga gattgtagca cagtttgtgg tttacttctt ggtagaggat      420
tatactaatt actgggttca tagattcttt cattgtaaat ggggttatga gaagtttcat      480
catattcatc atgagtatac agctcctatt ggttatgctg ctccttatgc tcattgggct      540
gaggttttgc ttcttggcat tcccacgttt cttggacctg ctattgctcc tggtcatatg      600 attaccttt ggttgtggat tgctttacga cagattgagg ctatcgaaac tcatagcgga      660
tatgatttcc catggtctct gacaaagtac attccatttt atggtggagc tgagtatcat      720
gattaccatc actacgttgg aggacaaagc cagagtaact ttgcttcagt ttttacttac      780
tgcgattaca tctatggaac tgataaaggt taccgattcc agaagaagct tcttcagcag      840
atgaaggaga agtccaagaa gagcaacaag ctggttaatg gaggagagaa attcgattag      900

<210> SEQ ID NO 29
<211> LENGTH: 897
<212> TYPE: DNA
<213> ORGANISM: Brassica napus

<400> SEQUENCE: 29
atgatccctt acgcaacgat cgaagaggcc tctctggcgt taggccgaaa cctcacgacc       60
ctcgagactc tctggttcga ttactccgcc acgaagtcag attactacct atactgccac      120
aacatcctct tcctcttcct catcttctcc ctcgtccccc ccctctcgt cttcgtcgaa       180 ttggcgcgat ccgcctcggg atggttcgat cggtacaaga ttcagcccaa ggtcaagaac      240
tccttctccg acatgttccg ctgctacaga gatgtaatga agatgttcat cctcgttgtc      300
ggccctttgc agctcgtgtc ctaccccttca atccagatga ttgagattcg gagtgggttg      360
ccgttaccgt ctttcgggga gattgcggcg cagttagtgg tgtacttctt ggtggaggac      420
tatacgaact attgggttca tagattcttt catagcaagt ggggttacga gaagattcat      480
catatacatc atgagtacac tgctcctata gggtacgctg cgccttatgc gcattgggct      540
gaggttttgc ttcttggggt tccgacgttt cttggacctg ctattgctcc tggacacatg      600
attaccttct ggttgtggat tgctttgcgc cagattgaag ccattgagac tcacagcgga      660
```

```
tatgattttc catggacact gacgaaattc attccattct atggtggagc tgagtatcat    720
gattaccatc attacgttgg aggacaaagc caaagcaact ttgcttcagt tttcacttac    780
tgcgattaca tctatggaac tgacaaaggt taccgattcc aaaagaagtt tcttcagcag    840
atcaagcagg agtccaagaa gagcaacatg cagaatggag gagataagtt agattag      897

<210> SEQ ID NO 30
<211> LENGTH: 894
<212> TYPE: DNA
<213> ORGANISM: Glycine max

<400> SEQUENCE: 30
atgctcccct acgcttccat cccggaggcc gtggcggcgc tgggccgcaa cctcaccttc     60
gcggagaccc tctggttcaa ctactccgcc gccaagtccg attacttcct ctactgccac    120
aacattctgt tcctcttcct cgtcttctcc ctcgtccccc tccccctcgt cttcctcgaa    180
ttcaagcgct ctccttcgt ctcttcccac aagatccaac caaagtccg cttgtccctg      240 gccgaaacct tcaagtgcta caaagacgtc atgcgcatgt tcttcctcgt cgtcggcccc    300
ctccaactca tctcttaccc ttccatccag atgattggga tcaggacggg cttgccatta    360
ccttcgtggc gggagatcct ctcgcagctt ctggtgtact ttctcgtaga ggattacacc    420
aattactgga tccacaggtt tctgcacaac gattgggggt acgagaagat tcaccgcgtc    480
caccacgagt accatgcgcc cattggattc gccgcgccct atgcccactg gccgagatc     540 ttgatcctcg ggattccctc ctttcttggg cctgccatgg ttcctggcca cattatcacc    600
ttctggctct ggatagcctt gcgccagatt gaagccattg acacgcacag cgggtatgac    660
tttcctagga gtatcacaaa atatattcca ttttatggtg gtgctgagta tcatgattac    720
catcattacg ttgaagaca agccaaagc aatttttgctt cagttttcac atactgtgat    780
tacatctatg gaactgacaa ggggtatagg tatcagaaaa aaatacttca gaagttgaag    840
gaagagttgg caaatggtgt tgagcagaac ggaggattat acaagactga ctga          894

<210> SEQ ID NO 31
<211> LENGTH: 764
<212> TYPE: DNA
<213> ORGANISM: Glycine max

<400> SEQUENCE: 31 atgctcccctt accataccct tgaaggagca caagttgcac taggcagagg actaaccctt     60
gctgagacaa tatggttcaa atactctgcc aacaaacctg atttgttct tcattgccac     120 aacactctat tcttgtgctt atttactct atagctccaa ttcctttcgt attaatggag     180
cttagtggga tgagaagct aaacaaacac aaaattcagc cctcggttaa gagatcattc     240
aaggaaatgt tcaagtgcta caaagatgtc atggagacct tgtcattgc agttagccca     300 ctacagataa tttcttatcc caccatcaag tggattggga tcagaactgg tttgtcattg    360
ccatcaggct gggagttatt ttggcaatta tttatttact ttgtcataga agatttttcg    420
aattattgga ttcataggat gctccattgc aagtgggcat ttgagaagat tcacaaggtc    480
catcatgaat atgtagcacc aattgggctc tcagcacctt atgcccattg gccgagata     540 atcatattgg gtatcccct cgtttctagg cccagcactg gttcctggc atataacaac    600 ctattggcta tggttcattt tgcgacagct agaagccatc gagactcata gcgggtatga    660
tttttcttgg gaggcccaca aaatatatac cattttatgg agggcctgca taccatgact    720
accatcacta cgttggtgga aaaagtcaaa gcaactttgc ctca                     764
```

<210> SEQ ID NO 32
<211> LENGTH: 918
<212> TYPE: DNA
<213> ORGANISM: Hordeum vulgare

<400> SEQUENCE: 32

| | | | | | |
|---|---|---|---|---|---|
| atgctcccgt | gggcgacggc | ggcggaggcc | gaggcggcgc | tgggccggcc | catgacgccc | 60 |
| gcggaggcgc | tctggttccg | gtggaccgcc | gggacgcccg | actacggcct | ctactgcctc | 120 |
| aacatcctct | cctcctcct | cgtcttcacg | ctcgcgccgc | tccccgtcgc | gctcctcgag | 180 |
| ctccgcgcgc | cgcgggccgt | cgggccgtac | aagctgcagc | ccgggtgcg | cctctcgcgg | 240 |
| gccgacttcc | tcaagtgcta | cggggacgtc | atgcgcatct | tcttcctcgt | catcggaccg | 300 |
| ctccagctcg | tctcctaccc | cgccgtcaag | atggtgggga | tccacaccgg | actgccgctg | 360 |
| ccgtctctgg | gggagatggc | ggcgcagctg | gtggtctact | tcctggtcga | ggactacctc | 420 |
| aactactgga | tccaccggct | gctgcacggt | gagtgggct | atgagaagat | ccaccggatc | 480 |
| caccacgagt | acaccgcgcc | cattggcttc | gcagcgccat | acgctcactg | gcagaggtg | 540 |
| ctcatacttg | gcatcccctc | cttcgctggc | ccggccattg | caccaggcca | catgattacc | 600 |
| ttctggctct | ggattatact | tcgtcagatg | gaagccattg | acacacacag | cggttttgat | 660 |
| ttcccattca | gcctgacaaa | gtatattccg | ttctatggag | gagcagaatc | ccatgattat | 720 |
| catcactacg | ttggaggcca | aagccagagc | attttttgctt | cggttttcac | gtactgtgat | 780 |
| cccctgtgtg | gcaccgacag | aggctacaga | ttccacaggg | cttccttacc | aatgttgagg | 840 |
| gccctggccc | ccccgccgc | caagaaagat | gccccatgg | gtttcagttc | cgcgaagggg | 900 |
| gattacgtgg | tcttatag | | | | | 918 |

<210> SEQ ID NO 33
<211> LENGTH: 906
<212> TYPE: DNA
<213> ORGANISM: Oryza sativa

<400> SEQUENCE: 33

| | | | | | |
|---|---|---|---|---|---|
| atgctgccct | acgcgacggc | ggcggaggcg | gaggcggcgc | tggggagggc | gatgacggcg | 60 |
| gcggagtcgc | tgtggttcag | gtactcggcg | gggatcccgg | actacgtcct | cttctggcac | 120 |
| aacatcctct | cctcttcgt | cgtcttcacg | ctcgcgccgc | tccccgtcgc | gctcctcgag | 180 |
| ctccgcgcgc | cggccgccgt | ggggccgttc | aagctgcagc | ccaaggtgcg | gctctcccgg | 240 |
| gaggagttct | tccgctgcta | cagggacgtc | atgcgcctct | tcttcctcgt | catcggcccg | 300 |
| ctccagctcg | tgtcctaccc | taccgtcaag | atggtgggaa | tccacacagg | ctgccactg | 360 |
| ccgtcgctgg | gggagatggc | ggcgcagctg | ctggtgtact | tcctggttga | ggactacctc | 420 |
| aactactgga | tccatcggtt | gctacatggg | gagtgggct | atgagaagat | ccaccgtgtc | 480 |
| caccatgagt | tcacggcacc | cattggattc | gccgcgccat | atgcacactg | gctgaggtg | 540 |
| ctcatcctcg | gcatcccctc | ctttgtcggg | ccagcgcttg | cacctggtca | catgatcacc | 600 |
| ttctggctct | ggattgtact | ccgccagatg | gaggccatag | agacacacag | cggctttgat | 660 |
| ttcccgttca | acctgacaaa | gtatattcca | ttctatggag | cgcagaata | ccatgattat | 720 |
| catcactatg | ttggacgcca | gagtcagagc | aatttcgctt | ctgttttcac | gtattgtgat | 780 |
| tatctatatg | gaaccgacaa | aggttacaga | taccataagg | cgtaccaagc | aaagatgaag | 840 |
| gctctggggc | aaacggaagg | cgagaaagca | gatagcaatg | gattgagcta | cgcgaagttg | 900 |

<210> SEQ ID NO 34
<211> LENGTH: 906
<212> TYPE: DNA
<213> ORGANISM: Triticum sp.

<400> SEQUENCE: 34

```
atgctcccgt gggcgacggc ggcggaggcc gaggcggcgc tggagcgcgc catgacggcc      60
gcggaggcgc tctggttccg gtggaccgcg gaggcgtccg actactacct ctactgcctc     120
aacatcctct tcctcctcgt cgtcttcacg ctcgcgccgc tccccgtcgc gctcctcgag     180
ctccgcgcgc cgcgggccgt cgggccgtac aagctgcagc cccgggtgcg gctctcgcgg     240
gccgagttca tcaagtgcta cggcgacgtc atgcgcatct tcttcctcgt catcggcccg     300
cttcagctcg tctcctaccc cgccgtcaag atggtgggaa tccacaccgg actgccgctg     360
ccgtctctgg gggagatggc ggcacagctg ctggtctact tcctggttga ggactacctc     420
aactactgga tccaccggct gctgcacggt gagtgggggct atgagaagat ccaccggatc     480
caccatgagt acaccgcgcc cattggcttt gccgcgccat acgcacactg gcagaggtg      540
ctcatacttg gcatcccctc cttcgctggg ccggccattg caccaggcca catgataaca     600
ttctggctct ggattatact tcgtcagatg aagccattg atacacacag cggttttgat      660
ttcccattca gcctgacaaa gtatattcca ttctatggag gagcagaata ccatgattat     720
catcactacg ttggaggcca agccagagc aatttttgctt ccgttttcac gtactgtgat      780
tacctatatg ggaccgacag aggttacaga ttccacaagg cttacttagc aaagttgaag     840
gatctggcgc aagcgacgg cgagaaagaa ggtgccgacg gattcgctta tgcaaagttg     900
gattag                                                                906
```

<210> SEQ ID NO 35
<211> LENGTH: 1384
<212> TYPE: DNA
<213> ORGANISM: Oryza sativa

<400> SEQUENCE: 35

```
ctcgaggtca ttcatatgct tgagaagaga gtcgggatag tccaaaataa aacaaaggta      60
agattacctg gtcaaaagtg aaaacatcag ttaaaaggtg gtataaagta aaatatcggt     120
aataaaaggt ggcccaaagt gaaatttact cttttctact attataaaaa ttgaggatgt     180
ttttgtcggt actttgatac gtcattttg tatgaattgg tttttaagtt tattcgcttt     240
tggaaatgca tatctgtatt tgagtcgggt tttaagttcg tttgcttttg taaatacaga     300
gggatttgta taagaaatat cttaaaaaa acccatatgc taatttgaca taattttga      360
gaaaaatata tattcaggcg aattctcaca atgaacaata ataagattaa aatagctttc     420
ccccgttgca gcgcatgggt attttttcta gtaaaaataa aagataaact tagactcaaa     480
acatttacaa aaacaaccccc taaagtccta agcccaaag tgctatccac gatccatagc      540
aagcccagcc caaccccaac caacccaacc cacccccagtc cagccaactg gacaatagtc     600
tccacacccc ccactatca ccgtgagttg tccgcacgca ccgcacgtct cgcagccaaa      660
aaaaaaaaaa gaaagaaaaa aagaaaaag aaaaacagaa aggtgggtcc gggtcgtggg      720
ggccggaaac gcgaggagga tcgcgagcca gcgacgaggc cggccctccc tccgcttcca     780
aagaaacgcc cccatcgcc actatataca tacccccccc tctcctccca tcccccaac       840
cctaccacca ccaccaccac cacctcctcc ccctcgctg ccggacgacg agctcctccc      900
```

```
cctctccccct ccgccgccgc cggtaaccac cccgcccctc tcctcttttct ttctccgttt      960 ttttttttccg tctcggtctc gatctttggc cttggtagtt tgggtgggcg agaggcggct     1020
tcgtgcgcgc ccagatcggt gcgcggggagg ggcgggatct cgcggctggg gctctcgccg     1080
gcgtggatcc ggcccggatc tcgcggggaa tgggctctc ggatgtagat ctgcgatccg      1140
ccgttgttgg gggagatgat gggggttta aaatttccgc catgctaaac aagatcagga      1200 agagggaaa aggcactat ggtttatatt tttatatatt tctgctgctt cgtcaggctt       1260
agatgtgcta gatctttctt tcttctttt gtgggtagaa tttgaatccc tcagcattgt      1320
tcatcggtag tttttctttt catgatttgt gacaaatgca gcctcgtgcg gagctttttt     1380
gtag                                                                 1384
```

<210> SEQ ID NO 36
<211> LENGTH: 1316
<212> TYPE: DNA
<213> ORGANISM: Zea mays

<400> SEQUENCE: 36

```
ctgccacatc ggcatgtact tagggcgcta gctctccccc gctagacacg tagcactctg       60
ctacacccct cattgtacac ctggatcctc ttcttacgcc tataaaagga aggaccagga      120
ccctcttaga gagggttggc cgcgcgggga cgaggacgag acaggcgctc tcttggggcc      180
gctcgcttcc ctctcccgcg tggacgcttg taactcccta ctgcaagcgc acccgacctg     240
ggcgcggggc gaacacaaag gccgcgggat tcccacctct ctcacgccgg tctccggccg     300
cctcgcttct ctcccctttcg cgctcgccct cgcgctcgac ccatctgggc tggagcacgc   360
gacgacactc actcgtcggc caagggacc ccccggtctc ggaacgcgac actatctttt    420
cacacttaga agctggcaag aaggtcaaac aaataaggtc ttatcgtgta tattattttt     480
gcattgcaga tagagtggag tttgaaataa aaggtgagat agcaggagtg gaaatgggct    540
caaaaattta tactataaaa ttgaatgatc aaatcgaatt aagatcggac tttatttgta   600
ttcattcttg aactaaaatt atttaactat cataatttat tgtggataaa catttggacc   660
acgattcatt gccatcgata ggaggtgttg taagagagcc agaaagctta ggacatgtaa   720
cccgattaaa taaagagtct tttgaagtgt ccctaagggc tacgtgaaaa aaaatcaaga  780
gacatactct ttgtgaagag tctgtctcta cacaaatctc tatataagtt gtgtctcaat  840
tacattatta tctagagact cagtgttgta tcacgtagtc ttttagtggt ctcttttatt  900
tgaaatccgt tgcagagtcc cttatgtgca gagtttggac atcccacgcg gtagaagcga   960
cgtggcagtt gccacagtat actgacgtgt gggcccagaa aaccccactg tcaatggaga   1020
aagaccatcc aaagcacaga gacttctatt ttattcgtga ctcttccaga atcccgacca  1080
tcccacacag agccacggac gcgggacgcc tacgcctcgc cgcgcccggg gccccgcaca  1140
gtccacagcc tttcagaacc ttccgtcgcc ttccagaaga acagaagccc accgtcgcc   1200 accaatataa atcgcccctc cagatcggca ctccgcacac caagaatcac atcacacagc  1260
gaaccgagaa accaacacag caacaagcaa agcagcgatc cgacatccga gagatg       1316
```

<210> SEQ ID NO 37
<211> LENGTH: 764
<212> TYPE: DNA
<213> ORGANISM: Zea mays

<400> SEQUENCE: 37

```
gtggagtggt ggacactagt gccgcggttc atctgacacg tgtcgccacg tgccgccatg      60
gcagcacctc agcccggccg gcgggccgac tgacgtcttg ggcaaagcgg cgagcgacgc     120
aggcggcgaa agccatccga tttgacccct cgctagaccc ttcaagaacg aacgctgtgc     180
tgctcagatc agaccgtgtc tgcctcaaag cgatgccagg acgccacgtc caagcaaagc     240
acccgatgcc attgccacct cccagcactc acgcgtgagc gtgactataa aaaacgcacc     300
ctctgcatcc gccccgtct gcctgcccta ccgaatcttt cgccgtccca tcagcccagc      360
aattcttcgc tgttcgagga cccctcggtt tcgaccgaag cccagcaagc cgaccacaca     420
ccgctgccgt tggttccgtc caagagatg ggcaagtcct ggtcgctcat cagccacctc      480
cacaccgtcg ccgggtagtt tcactgttcc ctcgcagttc gttttccgat tcctcctcgt     540
ccatctattg ggctcgctcg acgctggatg cctgacgtgt gcgtttgctg cttctttgtc     600
ttgtctgtcc ctccctcccg tttcgcaggc caagcatcac cctgctgtac cctctgtaag     660
ttccttcatc accctaataa tagcagggac cagttttacc agtgcagcag tgaccgacca     720
cggtccacgg catacgtgag ctgagagcat cgtgctggga catg                      764

<210> SEQ ID NO 38
<211> LENGTH: 1380
<212> TYPE: DNA
<213> ORGANISM: Zea mays

<400> SEQUENCE: 38
cgacctgcag gcggccgcga attcactagt gattactata gggcacgcgt ggtcgacggc      60
ccgggctggt aagacttaaa atcaacaat atcttcacat gacttaatta taatgtcttg     120
cttgagacgt tgttttttgct actacataag ataaagttca aataaatgca tggtggagtt    180
cagcctaggc aaagtgatgg tccgaatgat taacacccca agcaagacat tataagtcat    240
gtgaagatct gcaagacgtg ctaagagtct ctgacacacc aacaagtgga agcccgaaca    300
aacaaaaacg aagccatcaa agttgagata agaggtgga taaattgaaa attgtctcat      360
gattttggat atactcaaat cgacatgact tcatctctaa actatagaac ttttgatttg     420
cttttcaaaa agtccaagat caacaaaacg tgttggtggg tgcgggtttg gttcttaacc     480
caataggttt tttctcgtgt gtatgaaaag gttgtaccca tgtgtgaccg agccagacag     540
gggtacgggc aaaccgaagg gaaaccactt aggtggatcc cttggctagc ctgagactga     600
cacaccataa gtgatcggcc gcttttaact acgcctggtg ccgagccaca atagagatgt     660
cggtctgtct cccacttatg acctacgaac ccctcgtact atggctcatc tatgggtcgt     720
gtgccccttg gcttactgcg cactcatgcc ctatcaaggc taggccagag tgcgtaggcc     780
gctttcagag atcactcggt gaaaaaatca ctcggtgatg aaaccggcga actgtcgttg     840
ggtgggtggg tcttactatc aaagaaaacg tattccagca aacgtattcc actctccaca     900
aaataaacat ttctgttcgg ttacctaggt gaggcatcct gtaagaactt ggctgtgttt     960
agtcacagca aacgtatacc actctccaca aaataaaata aaaacgggt cagtgaagct     1020 gcaattaatc ccttctcttg cttgctggtt gctgccaggg aaatggcatt agtgtttgtt    1080
cccgttccga agaccgcagc aaccccggga atcggaaacg cctgcccct gcagcaccaa     1140 agaccgtacc aaccccgca atcgcagttc gcaaaccaaa ctaatttgtg tacacaaacc     1200
ggccccgtct cggttctatt ctataaaacc cccgccagac cgctggcttg ttccgtcgcc     1260
tccgctgtcc gctgcacaga ctgtagtacc ggggcagggg caggggcagg gcacaaaca     1320 gagccacacc acacacagac cccacctacg ctacgctacg cgcgtgctgg gcgagtgatg     1380
```

<210> SEQ ID NO 39
<211> LENGTH: 574
<212> TYPE: DNA
<213> ORGANISM: Zea mays

<400> SEQUENCE: 39

| | | | | | |
|---|---|---|---|---|---|
| gtcctaattg | gtactcctga | gatactatac | cctcctgttt | taaaatagtt | ggcattatcg | 60 |
| aattatcatt | ttacttttta | atgttttctc | ttctttaat | atattttatg | aattttaatg | 120 |
| tattttaaaa | tgttatgcag | ttcgctctgg | acttttctcg | tgcgcctaca | cttgggtgta | 180 |
| ctgggcctaa | attcagcctg | accgaccgcc | tgcattgaat | aatggatgag | caccggtaaa | 240 |
| atccgcgtac | ccaactttcg | agaagaaccg | agacgtggcg | ggccgggcca | ccgacgcacg | 300 |
| gcaccagcga | ctgcacacgt | cccgccggcg | tacgtgtacg | tgctgttccc | tcactggccg | 360 |
| cccaatccac | tcatgcatgc | ccacgtacac | ccctgccgtg | gcgcgcccag | atcctaatcc | 420 |
| tttcgccgtt | ctgcacttct | gctgcctata | atggcggca | tcgaccgtca | cctgcttcac | 480 |
| caccggcgag | ccatcgag | aacacgatcg | agcacacaag | cacgaagact | cgtttaggag | 540 |
| aaaccacaaa | ccaccaagcc | gtgcaagcat | catg | | | 574 |

<210> SEQ ID NO 40
<211> LENGTH: 571
<212> TYPE: DNA
<213> ORGANISM: Zea mays

<400> SEQUENCE: 40

| | | | | | |
|---|---|---|---|---|---|
| ctcgagggta | ctcctgagat | actataccct | cctgttttaa | aatagttggc | attatcgaat | 60 |
| tatcatttta | cttttaatg | ttttctcttc | ttttaatata | ttttatgaat | tttaatgtat | 120 |
| tttaaaatgt | tatgcagttc | gctctggact | tttctgctgc | cctacactt | gggtgtactg | 180 |
| ggcctaaatt | cagcctgacc | gaccgcctgc | attgaataat | ggatgagcac | cggtaaaatc | 240 |
| cgcgtaccca | actttcgaga | agaaccgaga | cgtggcgggc | cgggccaccg | acgcacggca | 300 |
| ccagcgactg | cacacgtccc | gccggcgtac | gtgtacgtgc | tgttccctca | ctggccgccc | 360 |
| aatccactca | tgcatgccca | cgtacacccc | tgccgtggcg | cgcccagatc | ctaatccttt | 420 |
| cgccgttctg | cacttctgct | gcctataaat | ggcggcatcg | accgtcacct | gcttcaccac | 480 |
| cggcgagcca | catcgagaac | acgatcgagc | acacaagcac | gaagactcgt | taggagaaa | 540 |
| ccacaaacca | ccaagccgtg | caagcaccat | g | | | 571 |

<210> SEQ ID NO 41
<211> LENGTH: 733
<212> TYPE: DNA
<213> ORGANISM: Oryza sativa

<400> SEQUENCE: 41

| | | | | | |
|---|---|---|---|---|---|
| tagcatatat | aaaatcattt | gtcagagtga | acaacacat | ccaaattaat | gacaaatata | 60 |
| aattactaat | ctactttgat | ccatctcatc | atttttaaag | aaaatactaa | aatccattaa | 120 |
| aagatcattt | tggaaaatta | aactttat | gaaaataaac | taactcatgt | aaaattatac | 180 |
| cgttttcctg | ttacatgtac | aggatataaa | ttaacagcgc | gccttttggc | gcgctgattt | 240 |
| tctagtcgaa | aagttaaacc | ggggtataag | tgtagcacct | tcgctccact | caaagaaaat | 300 |
| gtaagccgaa | gacttgagaa | gcttccagaa | tccagagatc | gcagcagaaa | aggagcgaac | 360 |
| aaggcaaacc | tctcaaagga | aaaagaaaa | ataataaagg | aggaaacctg | tcaaacacca | 420 |

-continued

| | |
|---|---|
| ccctatgaca agtgggtccc actcgaacca accgtacggc cccccacccc aaacccgctc | 480 |
| cccccctcgct ccgaaaatat ccacctctct agatctttct cgtcgcaaac gcccttccgc | 540 |
| ccccgcctcg ccgcgcccat tccaccacct ttccgaacct tccactccct tccagactcc | 600 |
| accccacgt caccccctatt taaaccccctc ctccaccga gcaatcaagc gacaagatcg | 660 |
| agaagccaca aaccccagcg cgatccgagg tagaagaaga agaagaagaa gaagaagaag | 720 |
| aggcgatcga gag | 733 |

<210> SEQ ID NO 42
<211> LENGTH: 1019
<212> TYPE: DNA
<213> ORGANISM: Oryza sativa

<400> SEQUENCE: 42

| | |
|---|---|
| aatataccat tcgctaaaaa atttgatttt tctatgacgg agaaagcagt agtgtaagca | 60 |
| gagcgcccgt aaacatatcc tcacttttgg ttcatctcat atttttgtaa gatggaggaa | 120 |
| acatgagtga aattagagca ccctgtaaac atatcctcat tttggttcgt ctatcagtca | 180 |
| cgtaactttg ttatttctgt cggttaccta gtactaatac ctaagatgat aatccactgt | 240 |
| aatgggaaga tgagcacggt tttatatctg aaactgaaaa tgggtctgtt ggtcataaaa | 300 |
| cttactacct ccgtttcgaa atatatcaaa ctagcttgta ttagattaga cacgatctat | 360 |
| tattcaattt ggacagagtc catatagcta tgatatgctt actatttcat attgctttca | 420 |
| tgaacttaac ttaaagtttt ggaccacaat gaaagtttca gttcatatca tatggcatac | 480 |
| tacttctatt ctttttttt tgttaaaaaa aaactggagc tctcaatttt tttaaagttt | 540 |
| gtcctgttac aattttaatc agttctttat tattcctctc cacatcaaca ttttttcctc | 600 |
| gatgatccgg ttccctttg acctcactgc actgtcccag atctctcatt aatccaaccc | 660 |
| agaaaaaaaa aacagtacaa aataaaatac acaagattca acaaagcaac ctgacctggt | 720 |
| cggtgctgta ccacgtggca tctcccctcc atgtcccaat cacttcgaga gacaaaagaa | 780 |
| acactcctcc agtggcatcc tgccatgtgt cctccattct tgtacttaat ctcttcttat | 840 |
| ttaaggcctc ataatctctt gctttccctt ccctagtaaa tcaaagaaca caaagcatcc | 900 |
| aaaacaacac caggaaactt cttttcaatc gatcactcca ctggtgagta gtgagtggct | 960 |
| agtgactggt cagttcatca cttgtgaagg ttttgcaatc aggaaaagtt cagaagatc | 1019 |

<210> SEQ ID NO 43
<211> LENGTH: 1500
<212> TYPE: DNA
<213> ORGANISM: Oryza sativa

<400> SEQUENCE: 43

| | |
|---|---|
| tttgatttgg gacaaaaggt tggtgaaatg gacatatttt cacatatata tatgctatat | 60 |
| ttttcttctc agtttaccga aaagatgtac ccttatatct cgtcatcgat tttgggtcag | 120 |
| gccagaaaac cattggtaac agaatatatg catagttttc tttatcaata aaattaatgt | 180 |
| tttatttaaa aatcgataaa ggaacttttt acaaaattag gctagaaatg gtctgtctat | 240 |
| tatgacaagg taaacttttg cgacattaat ttggatggca acttcaacaa ttcaaattgt | 300 |
| cgttgtccac aaatctcttg gttgtagaag acccacgcgt ctgcaacatt tttgcgccga | 360 |
| aaacttaata cataaacttg atttgttggg atacatggtg cagaagatac gatcattaat | 420 |
| aattcaaaca gtgcatttca tggtccaact gactgccacg tcattgaacc cgtaatcatt | 480 |
| cgctaagcca aatcaaattg gcctcaaatg aattttcagc acgacttttt acgccccaaa | 540 |

```
aacctagtac tccctccagt tggaaatgta ccctaccaag aaacttgtgt ccgtcacgac      600
gcctgtatca tcaatctagt cctcttttgt aacaaaataa ttttagaaga tttcttttaa      660
tgccgtagaa attaaattaa tcctaatgaa aatcatgtaa aactcacccg ttataaaatg      720
tcactaaccc cctacacggt tggtgtcctc tttgtagccg aaatgcctcc tctttggcca      780
ctgcatctcc acccattttt caaacatctc caactaactt tttgttccat ttgcaaaaat      840
gcaaaatgcg aaatgttaac ttcacacaca ccccctacc actacaaaac tctcaccaac      900
cccaatctag ctatcagttc agaaagcacc ttcccttctt tccctattag agcaagtcta      960
atagtacagc tcactactag cttcaattta tctataacca atctaatagt caattcatac     1020
aatagttgct tattatacta ttaatatatg gtctcacctg tcatacacac agtgtgtctt     1080
atagtccgtg ctgcagctgg ctacatatct gtagcctgct agtcttctct ctcatcgttt     1140
atctcattaa aatatgttta tagctggcta atagcttgct aatagcatgc tattgtacct     1200
gctcttacca ccttctttcc cttttggcaa atggcaatga gtgcaaaaat gcttggaaaa     1260 ataaccccc ccccccacc cccacctgat tatttccagt agggccaaaa tccgggccca      1320
cgtccgcaac ccatgtgggc cccacatccc ccacaccaac cctctgcacc caaaatcccc     1380 atcccccac tatatataat ccccgccgtt ggatcatcgc cctcagcaga gcagcgcatc      1440
tgcatccaaa accaaaccca aactcgtctt ctccaccgga gcagagcagc ggcggcggca     1500

<210> SEQ ID NO 44
<211> LENGTH: 1180
<212> TYPE: DNA
<213> ORGANISM: Oryza sativa

<400> SEQUENCE: 44
aaaacctctt ctttaacatg taaacgacct ggaggatgtc aactctgaca cgctggcgaa       60
atcatccacc tatgtctttg ccgcggtata ggatgaacat gggtagagaa aaaaatcggg      120
gtgatccaaa gtgcaataga cgtgacccaa aaagtgtaat tcactaaaaa aaacttacca      180
acgaagcaat gctttggcag tgattttttac ctttcagtca tgggcatgac ctgcattgta      240
aaataacgtg gttgtgaatt caaactcaaa tgtgtttttc tttcacaagt tgccgttaaa      300
aatatgtttc gcaagagact cactgctccc agtgaaagca gtgaattgaa gcattcccga      360
aacccactgg aatgatctag tactcactct acgatgtaca gtgaagtaat acttcaaaac      420
tggtgtaatt tggtatgcca aaaggactcc atagtttcac gacatatttc caaacggttc      480
aggatcagta ctgcccatct gcctggggcc cacactagcg ggcaattggt tctcgtagtt      540
tctcgttctc aatcaatcat tccatactcg ctatcccctc catcacagaa taaatgcaac      600
aatgagtttc cgtgtacaaa tttaatcgtt cgtcttattt aaaatatttt ttaaaaaact      660
aaaaaacaaa agtcacgcat aaagtactat tcatgttttta taatctaata acagtataaa      720
tactaatcat aaaaaaaaat tcaaataaga tggacgatta agttgaaaca ctgaaattca      780
tggctgcttt tgttttgaga ctgagggagt acacgataag atttgatcgc aatcaaagta      840
acctacatca agaagcaag atatgtgggg gaaaaatgaa tactctagag caaattaagg      900
tgagccccgc tttgtagagg ctgatggagt actggagcga cggaagcgaa gcagatcgag      960
tgtgctgtaa agcgaaacga gcaagaacca gagaagtcca gagatttcag gacagattag     1020
ttgtgaacct ataatatcc tgcctcattc cccaacctcc atccatcgag ccaagactga     1080
agcatttgat cgagctccaa acaaacactc gttccaaact tcctccaatc cacttcatac     1140
```

```
aaagaaacct aagcagctag cgatccacga caaaccaaca                    1180
```

<210> SEQ ID NO 45
<211> LENGTH: 339
<212> TYPE: DNA
<213> ORGANISM: Oryza sativa

<400> SEQUENCE: 45

```
gttcgtgact tttggcaagg gatcgaatcg gaagcgaatg ggtgggccca aaacgggccg     60
gttattttac tgggactaaa gatatcggcc catctgaatt gtgcgttccg ccggataagg    120
gataactgaa ggcggcgctc agtcccgcgc cttctgaacc cttcccgtgg aaggggcata   180
cagccttgca gcggcagctt ccggaagctt ctgaattctt ctccaagatt tgccgcgacg   240
ataaatcctc tcgtttctcc gctcgctgat tcattctcaa cgcaaaatcc aaagataag    300
cacagttacg cggcgagagc gagagaggag tggagagcc                          339
```

<210> SEQ ID NO 46
<211> LENGTH: 991
<212> TYPE: DNA
<213> ORGANISM: Oryza sativa

<400> SEQUENCE: 46

```
tgcttgccct tgtcctcatg tacacaatca gcttgcttat ctctcccata ctggtcgttt     60
gtttcccgtg gccgaaatag aagaagacag aggtaggttt tgttagagaa ttttagtggt    120
attgtagcct attttgtaatt tgttgtact ttattgtatt aatcaataaa ggtgtttcat    180
tctattttga ctcaatgttg aatccattga tctcttggtg ttgcactcag tatgttagaa    240
tattacattc cgttgaaaca atcttggtta agggttggaa catttttatc tgttcgtgaa    300
acatccgtaa tattttcgtt gaaacaattt ttatcgacag caccgtccaa caatttacac    360
caatttggac gtgtgataca tagcagtccc caagtgaaac tgaccaccag ttgaaaggta    420
tacaaagtga acttattcat ctaaaagacc gcagagatgg gccgtgggcc gtggcctgcg    480
aaacgcagcg ttcaggccca tgagcattta ttttttaaaa aaatatttca aacaaaaaa     540
gagaacggat aaaatccatc gaaaaaaaaa actttcctac gcatcctctc ctatctccat    600
ccacggcgag cactcatcca aaccgtccat ccacgcgcac agtacacaca catagttatc    660
gtctctcccc ccgatgagtc accacccgtg tcttcgagaa acgcctcgcc cgacaccgta    720
cgtggcgcca ccgccgcgcc tgccgcctgg acacgtccgg ctcctctcca cgccgcgctg    780
gccaccgtcc accggctccc gcacacgtct ccctgtctcc ctcccaccat gccgtggcaa    840
tcgagctcat ctcctcgcct cctccggctt ataaatggcg ccaccaccct tcacctgctt    900
gcacaccaca gcaagagcta agtgagctag ccactgatca gaagaacacc tcgatctccg    960
agagttttttt ttcagcttta gcttaagcag g                                  991
```

<210> SEQ ID NO 47
<211> LENGTH: 368
<212> TYPE: DNA
<213> ORGANISM: Zea mays

<400> SEQUENCE: 47

```
atctctctct ctctctctaa aagaaggaac acgtatcggt agatcgattc cagacgctta     60
ccatcgcatc gttatcatag agttaaaatc gtctgtgtcg cgtaacattt ctgaaaataa    120
tttcggaaga tgaagataat gtttctgtta cgtaattttc cgtcccttgt tgttcacatg    180
tgccgtaccca cgtgtcagag tgagagatgt accagtataa agaagcgcag agcccccaag    240
```

```
agccggagct gccatgaggc ccgaacagtt gaagctacta gcgtgtagct agggaagaga    300
agcgcgcgag tagctagcag acgtacgtag gcagaagcct agctgggttt gaagggcccc    360
gatcgatg                                                             368

<210> SEQ ID NO 48
<211> LENGTH: 2091
<212> TYPE: DNA
<213> ORGANISM: Zea mays

<400> SEQUENCE: 48
atccacgctc gctcgggtgt cgggtcagat cgatccagtt ggcgcacgta ataatccttt     60
tccccagaag gagtcgaacc cctcctcccc gtccaatcca atcaaagcga ccaatcgact    120
ggctgtccta cacacacaca aaaccgaccg aggcgacaca ccgcagcagt gatcattctg    180
agcatttgca gaaaaggag aacgtcccga atcctggtg gttgtattgt gtgattgctc     240
actcagtccg tgcagggtca gggtgaagcc aagccaacaa cccaacgctc gctgggagta    300
gggtccaccg gatttattgg cagtacatcg ctgtttggtc ctcctgccct tcgcttattt    360
tttaattcgg cagacgtgca cagacagggc accaccggac caaggaaggg cgcacaccgt    420
cgtcagtcac caggtgggtg tgatcagcag ccgcttctct tgtgctgctt tatagcgtat    480
gaaattccag tgtccctgtt ccacctgcat gcaattggtt tgactgaaca acatgatagc    540
aagtgatact atatatattt ttatagagga acacagtgaa aaaatattta gtattattac    600
gtgcatgaaa ttgtattcac agttatccct gatgcaacgc aattgttcaa tatatagcag    660
tatatattat acgaagtata tatgtatatc taattttatg agaccgggag aaggtgtatt    720
cacagtacag tgcagggcca tgccatgca gcccttgggg cctgaaaagg gtcgcgtgaa     780
gtggccaacg ctgtgcaatt gcaaccaaac aaacttttgg tggcggggtc cctgtccctg    840
gccggctttg cccacaggcc acagcgcatc acaccaccgc tttatagcgc caccccacca    900
ccctcgtctc tcccccgtc gagcacacaa cacaccctcc tcgtcctcca atccaatcaa     960
cctggtagac tcgcttcgct tctcccccca gctcggacgg agctcctcgc agcagccgcc   1020
gatcaacctg cgctcgggct cagcgctgga aggtgagagc tcagtgcctc gtcccgcccg   1080
ccccaaatct ggttcttgtg ctggctctgg ctgtgcgctg cacgaattct gcatctggtt   1140
ctttcgagac gcaattcccg gaccgtgggc tttggtttcg gaggggggccg agagtaaggc   1200 gttaggactt tctccgagct gcaaggccgc tcgtcgttgc ggcatttttc gtttcgcttg   1260
tcctgtgatg agagatgtgc atttcccttt ggcgggctta ccgttccctg ctcgtctgta   1320
tgtgtgtatg tttgtgtgac cttttccctca acgccaggct cttctccccct cttgctgttt   1380 ctttcagcag tacagacgcg catctgtaca gcgcctttct tcggtcctgg gttatgattg   1440
atccgttaac agttggtcac caagtgctgg ctgtttaata tgtactataa gcttcttggt   1500
gccgctgcct ctgcctatac gactttatgc gctgcctgca caagtctcag ccatctgtgg   1560
gaacgtgtgt ctctcaccta cctttcatat tgcactagct ggattgaatc attctgcttt   1620
ggagagatgt ccggtcattt ttttttaaat cattttcatc tcgcgtacta gttttgttt    1680 tgttttgcga gagagtaatt ttttttttaat atttactgtc tcctgtccca tttgctgttt   1740
ctttacccag aaatttccac cagattcagt caaacgaaac tcctgtgctc ttttttttct   1800
ccctttcaaa agggtgtgta accgactacc gactcagata atataagtgc ggtcacatat   1860
cacatgatat catctcgcct ctctcccttc tcctgtgttt tatttttcctt ttttctaacc   1920
```

```
acagcgtgat gaacttcttt ttttttttggg gggggggggg ggggtaacta cagcttagcg    1980
aacatgaatg ggtagtttta caactaatgc aacggctggt tcactgaaca actgtaggtg    2040
ttggaagaga atagcctgaa ggttcacagt aaccttcatc tgtcggaagc c             2091
```

<210> SEQ ID NO 49
<211> LENGTH: 1106
<212> TYPE: DNA
<213> ORGANISM: Zea mays

<400> SEQUENCE: 49

```
atccacgctc gctcgggtgt cgggtcagat cgatccagtt ggcgcacgta ataatccttt      60
tccccagaag gagtcgaacc cctcctcccc gtccaatcca atcaaagcga ccaatcgact     120
ggctgtccta cacacacaca aaaccgaccg aggcgacaca ccgcagcagt gatcattctg     180
agcatttgca gaaaaaggag aacgtcccga atcctggtg gttgtattgt gtgattgctc      240
actcagtccg tgcagggtca gggtgaagcc aagccaacaa cccaacgctc gctgggagta     300
gggtccaccg gatttattgg cagtacatcg ctgtttggtc ctcctgccct tcgcttattt     360
tttaattcgg cagacgtgca cagacagggc accaccggac caaggaaggg cgcacaccgt     420
cgtcagtcac caggtgggtg tgatcagcag ccgcttctct tgtgctgctt tatagcgtat     480
gaaattccag tgtccctgtt ccacctgcat gcaattggtt tgactgaaca acatgatagc     540
aagtgatact atatatattt ttatagagga acacagtgaa aaaatattta gtattattac     600
gtgcatgaaa ttgtattcac agttatccct gatgcaacgc aattgttcaa tatatagcag     660
tatatattat acgaagtata tatgtatatc taattttatg agaccgggag aaggtgtatt     720
cacagtacag tgcagggcca tggccatgca gcccttgggg cctgaaaagg gtcgcgtgaa     780
gtggccaacg ctgtgcaatt gcaaccaaac aaacttttgg tggcggggtc cctgtccctg     840
gccggctttg cccacaggcc acagcgcatc acaccaccgc tttatagcgc cacccccacca    900 ccctcgtctc tccccccgtc gagcacacaa cacaccctcc tcgtcctcca atccaatcaa     960
cctggtagac tcgcttcgct tctcccccca gctcggacgg agctcctcgc agcagccgcc    1020
gatcaacctg cgctcgggct cagcgctgga aggtgttgga agagaatagc ctgaaggttc    1080 acagtaaccct tcatctgtcg gaagcc                                         1106
```

<210> SEQ ID NO 50
<211> LENGTH: 1597
<212> TYPE: DNA
<213> ORGANISM: Zea mays

<400> SEQUENCE: 50

```
gatccacgct cgctcgggtg tcgggtcaga tcgatccagt tggcgcacgt aataatcctt      60
ttccccagaa ggagtcgaac ccctcctccc cgtccaatcc aatcaaagcg accaatcgac     120
tggctgtcct acacacacac aaaaccgacc gaggcgacac accgcagcag tgatcattct     180
gagcatttgc agaaaaagga gaacgtcccg aaatcctggt ggttgtattg tgtgattgct     240
cactcagtcc gtgcagggtc agggtgaagc caagccaaca acccaacgct cgctgggagt     300
agggtccacc ggatttattg gcagtacatc gctgtttggt cctcctgccc ttcgcttatt     360
ttttaattcg gcagacgtgc acagacaggg caccaccgga ccaaggaagg gcgcacaccg     420
tcgtcagtca ccaggtgggt gtgatcagca gccgcttctc ttgtgctgct ttatagcgta     480
tgaaattcca gtgtccctgt tccacctgca tgcaattggt tgactgaac aacatgatag      540 caagtgatac tatatatatt tttatagagg aacacagtga aaaatatatt agtattatta     600
```

```
cgtgcatgaa attgtattca cagttatccc tgatgcaacg caattgttca atatatagca      660
gtatatatta tacgaagtat atatgtatat ctaattttat gagaccggga aaggtgtat       720 tcacagtaca gtgcagggcc atggccatgc agcccttggg gcctgaaaag gtcgcgtga       780 agtggccaac gctgtgcaat tgcaaccaaa caaacttttg gtggcggggt ccctgtccct      840
ggccggcttt gcccacaggc acagcgcat  acaccaccg  ctttatagcg ccaccccacc      900
accctcgtct ctccccccgt cgagcacaca acacaccctc ctcgtcctcc aatccaatca      960
acctggtaga ctcgcttcgc ttctccccc  agctcggacg gagctcctcg cagcagccgc     1020
cgatcaacct gcgctcgggc tcagcgctgg aaggtgttgg aagagaatag cctgaaggtt     1080
cacagtaacc ttcatctgtc ggaagccctc cgccgccgcc ggtaaccacc ccgcccctct     1140
cctctttctt tctccgtttt tttttccgtc tcggtctcga tctttggcct tggtagtttg     1200
ggtgggcgag aggcggcttc gtgcgcgccc agatcggtgc gcgggagggg cgggatctcg     1260
cggctggggc tctcgccggc gtggatccgg cccggatctc gcgggaatg  gggctctcgg     1320 atgtagatct gcgatccgcc gttgttgggg gagatgatgg ggggtttaaa atttccgccg     1380
tgctaaacaa gatcaggaag aggggaaaag ggcactatgg tttatatttt tatatatttc     1440
tgctgcttcg tcaggcttag atgtgctaga tctttctttc ttcttttgt  gggtagaatt     1500 tgaatccctc agcattgttc atcggtagtt tttcttttca tgatttgtga caaatgcagc     1560
ctcgtgcgga gcttttttgt aggtagaagt gatcaac                              1597
```

<210> SEQ ID NO 51
<211> LENGTH: 907
<212> TYPE: DNA
<213> ORGANISM: Zea mays

<400> SEQUENCE: 51

```
atccacgctc gctcgggtgt cgggtcagat cgatccagtt ggcgcacgta ataatccttt       60
tccccagaag gagtcgaacc cctcctcccc gtccaatcca atcaaagcga ccaatcgact      120
ggctgtccta cacacacaca aaaccgaccg aggcgcacaca ccgcagcagt gatcattctg     180
agcatttgca gaaaaggag  aacgtcccga atcctggtg  gttgtattgt gtgattgctc      240
actcagtccg tgcagggtca gggtgaagcc aagccaacaa cccaacgctc gctgggagta     300
gggtccaccg gatttattgg cagtacatcg ctgtttggtc ctcctgccct tcgcttattt     360
tttaattcgg cagacgtgca cagacagggc accaccggac caaggaaggg cgcacaccgt     420
cgtcagtcac caggtgggtg tgatcagcag ccgcttctct tgtgctgctt tatagcgtat     480
gaaattccag tgtccctgtt ccacctgcat gcaattggtt tgactgaaca acatgatagc     540
aagtgatact atatatattt ttatagagga acacagtgaa aaaatattta gtattattac     600
gtgcatgaaa ttgtattcac agttatccct gatgcaacgc aattgttcaa tatatagcag     660
tatatattat acgaagtata tatgtatatc taattttatg agaccgggag aaggtgtatt     720
cacagtacag tgcagggcca tggccatgca gcccttgggg cctgaaaagg tcgcgtgaa      780 gtggccaacg ctgtgcaatt gcaaccaaac aaacttttgg tggcggggtc cctgtccctg     840
gccggctttg cccacaggcc acagcgcatc acaccaccgc tttatagcgc caccccacca     900
ccctcgt                                                               907
```

<210> SEQ ID NO 52
<211> LENGTH: 1039
<212> TYPE: DNA

<213> ORGANISM: Zea mays

<400> SEQUENCE: 52

```
gtgagagctc agtgcctcgt cccgcccgcc ccaaatctgg ttcttgtgct ggctctggct      60
gtgcgctgca cgaattctgc atctggttct ttcgagacgc aattcccgga ccgtgggctt     120
tggtttcgga gggggccgag agtaaggcgt taggactttc tccgagctgc aaggccgctc     180
gtcgttgcgg cattttctcgt ttcgcttgtc ctgtgatgag agatgtgcat ttcccttcgg    240
cgggcttacc gttccctgct cgtctgtatg tgtgtatgtt tgtgtgaccct ttccctcaac    300
gccaggctct tctcccctct tgctgtttct ttcagcagta cagacgcgca tctgtacagc    360
gccttcttc ggtcctgggt tatgattgat ccgttaacag ttggtcacca agtgctggct    420
gtttaatatg tactataagc ttcttggtgc cgctgcctct gcctatacga ctttatgcgc    480
tgcctgcaca agtctcagcc atctgtggga acgtgtgtct ctcacctacc tttcatattg    540
cactagctgg attgaatcat tctgctttgg agagatgtcc ggtcatttt ttttaaatca    600
ttttcatctc gcgtactagt ttttgttttg ttttgcgaga gagtaattt ttttaatat    660
ttactgtctc ctgtcccatt tgctgtttct ttacccagaa atttccacca gattcagtca    720
aacgaaactc ctgtgctctt ttttttctcc ctttcaaaag ggtgtgtaac cgactaccga    780
ctcagataat ataagtgcgg tcacatatca catgatatca tctcgcctct ctcccttctc    840
ctgtgtttta ttttccttt ttctaaccac agcgtgatga acttcttttt tttttggggg    900
ggggggggg ggtaactaca gcttagcgaa catgaatggg tagttttaca actaatgcaa     960
cggctggttc actgaacaac tgtaggtgtt ggaagagaat agcctgaagg ttcacagtaa    1020
ccttcatctg tcggaagcc                                                 1039
```

<210> SEQ ID NO 53
<211> LENGTH: 3530
<212> TYPE: DNA
<213> ORGANISM: Oryza sativa

<400> SEQUENCE: 53

```
ggcttcccgc tgtgagagaa gtggctgcct ctcggttctc accaagcagt cgaaaatgcc      60
agaacagcga ccagatagga tcatcgtgcc atgcaggcat gcagcctttg agaactgaaa     120
gagccggtga aagtcctgca aagcgaaaag caaatgaaca aacatctgcc tgtgctgctg    180
cctcgcctcg ctgtccttt ccggtgggtt gccgctgcta acctctgcct ccgcgatacg    240
tgacacgtca tcctccccccc accccacccc atgcttgcac ccccccccc ccccctccct    300
cccttattac caccaccccc ctcctccatc ctctctgct cctccaacct ggctcagttt    360
cctcctgttc ttgagagaac tgaatctgct gtccagctgc tgctccggct ggtctctgag    420
ttgaaggtaa ggttaatcgg tgtctctcag cctgaatgaa tttgtctatc tcctatggct    480
ttgtggtggt tgaattttgc gttctgggga tgttaggacc ttcttgttgg acaatttct    540
gagattctgg cttgctttgg atgggttggg ggaagagtta ggtgcttgct ggtgtgtatt    600
tcttttgcat ttcggttgtc ctgtgaagga tgcgtgttct cggcatttcc agctcattgt    660
gtctttgccc ttcagataac agttatcctc gtgcttttcc ttttcttc agcaaaacat    720
atctggactt ctgtacaagt gcttttttt tcttctttgg acgatatttt gttttgcatt    780
ctagtgattc tgtacaagtg ccatctgata gcatatcatc attcggcaac tggtgatttc    840
ccctatgcgg tctttcatgt acttgcatga ttgaacatat ggcagtgctt ctgtcggatg    900
ctatcgatgt tttacttgcg aaaggccggg gaacttttg cagatcttga ggttttagt    960
```

```
agtgatgcag tcattcaaaa agataacctt gtgctggtcc ttttgccttt cggctgcact    1020
tgcatgtgcg ttttctcaga gatgctgcat ctccagctca gcttctgtca tcagtcatta    1080
gtcattgcca tcttttatgt ggataaagtc aaagttaatt tagcaccgct gttttggagt    1140
tgtttggtca ttttatatat tttcatcagg tgttgtttac tgttcctggt actaaaattt    1200
cgaatttaca aatgactacc tcattctcct ttcttttttt ccttttttcct tgtggcagac   1260 cggttcctga agaatattc ttttcatgaa atgtacttcc ggttttttaa atagaatgat     1320
taaattacag taggatgaat aactaaattt gtcgatatgc cttgtaccgg tactccttgt    1380
tagttcttag tgaatctatg tatactattg cttgtcaaat tgtgaatttt actatcagct    1440
gtatgtatgt ctattgaaga actctcaaca gttctaactt cctaagatgt tttaatcaat    1500
tcttgctacc aacctggata cagtattctc cgtagttttt tcttcatttt tttttttaaag  1560 agatctattg agagtccttg gtacccatct tctgtagaat tgtccatgtg aacagttgct    1620
tcaagatttc tgctgcatct gtgatacggt atcactgata ctgtagtgat cagatccaaa    1680
acacatatat agttcgccac cattctaaaa cacatgtttg tgtgatcaga tctagctcgc    1740
caccatatat agttcaggtt ttcaagttgt aatatcactt gccttttgcg atagatatga    1800
caacacactt tgtgtcaggc tgtcccaatt ttctctgaat tttctctcat atatcatgat    1860
ttagttatgg cttttgttcc ttgacatttc aatgtctaat tgtccaatgt taagtaaatc    1920
cttttcatag cctgatttat tgaatacttg caggtacttg aataacttga aggttcctag    1980
gaaccttcat ttgttggaag atgtataggg ctaagagggc tgcattatct ccaaaggtga    2040
agcgccgtgt agggaagtat gagctcgggc gcaccattgg agaaggaacc tttgcaaagg    2100
tccggtttgc gaagaacact gaaaatgacg aaccagttgc tatcaaaatc cttgacaagg    2160
agaaggttca gaagcacaga ttggttgaac agattaggcg tgaaatttgt actatgaagt    2220
tagtaaagca tcctaatgtt gttcggctgt tcgaggtcat gggaagtaaa gcaagaatt     2280 tcattgttct ggaatatgtt actggaggag agctctttga aatcattgca actaatggaa    2340
ggttgaagga ggaggaagca cgaaaatact ttcaacaact tatcaatgca gttgactact    2400
gccacagtag gggtgtgtac cacagagact tgaagttaga aaatttgctg cttgatgctt    2460
ctggaaacct gaaagtatct gactttggtt tgagtgcttt aaccgagcaa gtgaaggctg    2520
acggtttgct gcacacgaca tgtggaactc ctaattatgt tgctccagag gtgattgagg    2580
acagaggcta tgatggggca gctgcagata tctggtcttg tggggtaatc ctttatgttc    2640
tgcttgctgg gttttttacca tttgaggatg acaacatcat tgctctttat aaaaagatct   2700
ctgaagctca gtttacctgt ccctcttggt tttctactgg agctaagaag ctgatcacca    2760
gaattctgga tcccaaccct acaactagga tcaccatttc tcaaatactg gaagatcctt    2820
ggttcaaaaa gggttacaaa ccgcctgtat ttgacgagaa atatgaaact gttttgacg     2880 atgtcgatgc tgcttttgga gactccgaag accggcatgt caaagaagaa actgaagatc    2940
agcctacctc tatgaacgcg tttgaactca tttcactgaa tcaggcactg aatctggaca    3000
atttgttcga ggcaaaaag gagtataaaa gagagacaag attcacatca caatgtcctc     3060
caaaagaaat tatcaccaag attgaagaag ctgcaaagcc acttggattt gatattcaaa    3120
agaaaaatta caagatgcgc atggagaacc tgaaagcagg tagaaaaggc aatctcaatg    3180
ttgcaactga ggttttccaa gtagctccat ccttacatgt ggttgagctc aagaaggcaa    3240 aggggggacac tctggagttc caaaaggtgc cattctttga caccggaaat ttcgctattt    3300
```

-continued

```
ccaacttgct atttactgcc aagtttaacc aaaatcaatt ctgctgtgaa acaacagttc   3360
tacagaaccc tgtcgaccca gctcaaggac gtggtctgga agtgcgacgg cgaggtcgaa   3420
ggcaacggcg ccgcggcgtg aacgtggttt ttgccatggc tttcggggca ccggttcttc   3480
gtgtacatag ctgctctgcc atcatcaatg gggtgttcgc cgtagagtag              3530
```

<210> SEQ ID NO 54
<211> LENGTH: 769
<212> TYPE: DNA
<213> ORGANISM: Rice tungro bacilliform virus

<400> SEQUENCE: 54

```
gatctcctac aaaagggagt agtaatattt aatgagcttg aaggaggata tcaactctct     60
ccaaggttta ttggagacct ttatgctcat ggttttatta acaaataaa cttcacaacc    120 aaggttcctg aagggctacc gccaatcata gcggaaaaac ttcaagacta taagttccct    180
ggatcaaata ccgtcttaat agaacgagag attcctcgct ggaacttcaa tgaaatgaaa    240
agagaaacac agatgaggac caacttatat atcttcaaga attatcgctg tttctatggc    300
tattcaccat taaggccata cgaacctata actcctgaag aatttgggtt tgattactac    360
agttgggaaa atatggttga tgaagacgaa ggagaagttg tatacatctc caagtatact    420
aagattatca aagtcactaa agagcatgca tgggcttggc cagaacatga tggagacaca    480
atgtcctgca ccacatcaat agaagatgaa tggatccatc gtatggacaa tgcttaaaga    540
agctttatca aaagcaactt taagtacgaa tcaataaaga aggaccagaa gatataaagc    600
gggaacatct tcacatgcta ccacatggct agcatcttta ctttagcatc tctattattg    660
taagagtgta taatgaccag tgtgcccctg gactccagta tataaggagc accagagtag    720
tgtaatagat catcgatcaa gcaagcgaga cgtcaaactt ctaagagag                 769
```

<210> SEQ ID NO 55
<211> LENGTH: 697
<212> TYPE: DNA
<213> ORGANISM: Zea mays

<400> SEQUENCE: 55

```
cggcccgggc tggtaaatat cggaatatta gcatgtcaac ttgcactctc taaggctcct     60
ttggaaagca ggatttaga aaaaaaaatc atataaattt tttacatgaa tcagtttatt    120
ttcggattat gaaatatttt ctcataacag tataacacat attttgtata taagttatta    180
tgttattata tataaccgtt gcaacgtacg ggcattcacc tagtaaagaa agaagattaa    240
ttattctctg gtggagattg tgcccgagcc cgaaggtcat gatatggacg ttgcaaaccc    300
acttcacgag gggacaaaaa agaaataggg ttaccacttt catcagttaa agggcgtgac    360
atggacgtgt tgaagatccg gcacattccc tgcgaaatat acacgtcatg gtactaacga    420
ggcatgaaac tggccacatg gccatggacg cgtgaagcgt gccatgcatt ggacatgcgg    480
catccgaact tctgaagatc atatcagaga gacactgatg tacgaactgc cgtaacattc    540
tattctatat atcccctcag tcctgttcc agttctcgtt aagctagcag caccaagttg    600
tcgaacactt gcctgctctt gagctcgatc aagctatcat cagctgcgtc ttgcgcacag    660
caacagcttc ccaactgcaa ccgtagcagc cagatct                              697
```

<210> SEQ ID NO 56
<211> LENGTH: 1455
<212> TYPE: DNA
<213> ORGANISM: Coix lacryma-jobi

<400> SEQUENCE: 56

```
cggtacctcg cgaatgcatc tagatcccct ttccgcgggc aattcgatag gtagaaatcc      60
gccgggttga taccectgca atcgtagcgt gatgagggtg tgaatgttgc cgatgtgtgg     120
acttcgagga aaatgatagc ccctggaatg ccgagatagc cgaagtcgag gtggtcgtgg    180
tcgggagaca cgcagcagta gcctattctt tggtaggggt cgatgttcaa gcgtcaacga    240
tcggctgggc gacataaaaa ttagcaccag ggtgaccttc ttgcttcttc gatcgtctgg    300
acgtcgagga gccccgcggc agcgcacgcg tctgcaccgt tatggtggcc gcgctcgcga    360
tggaatagaa ggggtaatga tggatccggc caggaaggcc acgacatcga cggatccaac    420
cggcaagacg gcgatccggt taaatagacg acggatctag ctgggaaggt agactctata    480
ttaaatgagg ttgtacatgc cctaataact ttataaatct aatttattca gaggcaaggt    540
agtagtatta tctttcccaa cggatagtta tctgatctgc cgttcagctt gatcgataac    600
tttataaatc taatttattc agaggccggc ggcagcgcac acgtctgcac cagtaatgtt    660
agccgcgcct gtggcgtaat agaagggggta acgatggatc cgaccagaaa ggcctcgaca    720
tcgacggatc cagacggcga tccggtcaaa gagacgacga atctagccga gaaggtagat    780
ctctcgagag agttcatatt aaatgatgtt gtacatgcca taataactct ataaatctaa    840
tttattcata ggcgaaggta gtagtattat ctttcccagc ggatcgttat ctgatctgcc    900
gttcagcttg atcgatccac gtcgtttgat ctcggcgagc agcacatggc ggctcttctt    960
gtgtacaggt ctcactctct gctacttcag tgcaaggcgg agtgaacgca cacaataacg   1020
tgagtattgt gggaactacc ttgtagatgc aaacgatgta aatccacctg ctccaccaag   1080
tgcccgcccg gctctatcca ttccattcgt caacatgcag gttcaagact ggcccgtgct   1140
ggaccagtga gcggtgccgg tggaccccaa tgcaagcgaa gcgagtgacc atcggggaag   1200
cctcccgtgc tgcccccaca tggcttgcct gaatgcctct ctctcgccgc agtgccctct   1260
ctctctcctc ctcctctccg tcgaagggcg tcacgagagc ccagagggca tccgaggccc   1320
ccaccccacc ccttcctccc gtgtatataa gcagtggcag ggtgagcgtc tctcctcaga   1380
ccaccactgc gccattggcc agctagagcc aaccagaaga gcttgcagtt actgagagtg   1440
tgtgagagag agagg                                                   1455
```

<210> SEQ ID NO 57
<211> LENGTH: 5365
<212> TYPE: DNA
<213> ORGANISM: Artificial
<220> FEATURE:
<223> OTHER INFORMATION: various organisms

<400> SEQUENCE: 57

```
aggattttc ggcgctgcgc tacgtccgcg accgcgttga gggatcaagc cacagcagcc      60
cactcgacct tctagccgac ccagacgagc caagggatct ttttggaatg ctgctccgtc    120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240
ttcacgccct tttaaatatc cgattattct aataaacgct cttttctctt aggtttaccc    300
gccaatatat cctgtcaaac actgatagtt taaactgaag gcgggaaacg acaatctgat    360
ccccatcaag ctagcttctg caggtcctgc tcgaggtcat tcatatgctt gagaagagag    420
tcgggatagt ccaaaataaa acaaaggtaa gattacctgg tcaaaagtga aaacatcagt    480
```

```
taaaaggtgg tataaagtaa aatatcggta ataaaaggtg gcccaaagtg aaatttactc      540
ttttctacta ttataaaaat tgaggatgtt tttgtcggta ctttgatacg tcattttgt       600 atgaattggt ttttaagttt attcgctttt ggaaatgcat atctgtattt gagtcgggtt      660
ttaagttcgt ttgcttttgt aaatacagag ggatttgtat aagaaatatc tttaaaaaaa      720
cccatatgct aatttgacat aattttgag aaaaatatat attcaggcga attctcacaa       780
tgaacaataa taagattaaa atagcttttcc cccgttgcag cgcatgggta ttttttctag     840
taaaaataaa agataaactt agactcaaaa catttacaaa aacaaccct aaagtcctaa       900 agcccaaagt gctatccacg atccatagca agcccagccc aacccaaccc aacccaaccc     960
accccagtcc agccaactgg acaatagtct ccacacccc ccactatcac cgtgagttgt      1020
ccgcacgcac cgcacgtctc gcagccaaaa aaaaaaaag aaagaaaaaa aagaaaaaga      1080 aaaacagca ggtgggtccg ggtcgtgggg gccggaaacg cgaggaggat cgcgagccag      1140
cgacgaggcc ggccctccct ccgcttccaa agaaacgccc cccatcgcca ctatatacat     1200 accccccct ctcctcccat ccccccaacc ctaccaccac caccaccacc acctcctccc      1260
ccctcgctgc cggacgacga gctcctcccc cctcccctc cgccgccgcc ggtaaccacc     1320
ccgcccctct cctctttctt tctccgtttt tttttttccgt ctcggtctcg atctttggcc   1380
ttggtagttt gggtgggcga gaggcggctt cgtgcgcgcc cagatcggtg cgcgggaggg     1440
gcgggatctc gcggctgggg ctctcgccgg cgtggatccg gcccggatct cgcggggaat    1500
ggggctctcg gatgtagatc tgcgatccgc cgttgttggg ggagatgatg gggggtttaa    1560
aatttccgcc atgctaaaca agatcaggaa gaggggaaaa gggcactatg gtttatattt     1620
ttatatattt ctgctgcttc gtcaggctta gatgtgctag atctttcttt cttctttttg     1680
tgggtagaat ttgaatccct cagcattgtt catcggtagt ttttcttttc atgatttgtg    1740
acaaatgcag cctcgtgcgg agcttttttg taggtagacc atggtcccct acgcgactgc   1800
ggcggaggcg gagggagcac tggggcgcac catgacgtgg gctgagacag catggtacga    1860
gtactcggcg gtgatgccag attcctggct gcactgccac accacattta tcctgttcgt   1920
catctacagc atcgccccgc tgcccctgct actcctagag cagttcgctc cgtccgtcgt    1980
gctgccgtac aagctgcagc cccgggtacg gctgcccccg gcagcctccc tcagctgcta   2040
catgacgcgc gcctgcatct ttccgctcgc cgttggcctt cagttcgtct cctatcctgc    2100
ggtcgccaag atactaagga cccgaatggg actgccgttg ccgtcggtga gggagaccat    2160
cgcgcagcta gtcgtatact ctctagtgga ggattacctc agctactgga tgcaccgtct   2220
gctgcacacc cagtggtgct acgagaagat ccaccgcgtc caccacgagt tcacggctcc    2280
tacaggcttc gccatgtcgt acagccactg ggccgagaac gtcgtccttt ctatcccggc    2340
cttggccggc ccagtgctcg tgccatgcca tgtcaccacg cagtggctat ggttctccat   2400
ccgcctaatt gagggcatta acacgcacag cggttaccat ttcccgttca gcccttgcag    2460
gctgattcca ttctacggag gggctgcata ccatgactac catcactatg caggaggccg    2520
tagccaaagc aactttgcac ccctgttcac ctactgtgat tatttatata ggacagacaa    2580
aggctacaga taccacaagc taaagcaaga gaagctgaag agtctagcag aaaatagtgc    2640
ggataaagga ggcaactact cattcgacga agggaaaaag aacagatatt tttgtgcctg    2700
agcgtacgaa gaataatcaa ggctattact tcgtcctgtt cgaagggccc gggggatcca    2760
ctagttctag ctatatcatc aatttatgta ttacacataa tatcgcactc agtctttcat    2820
ctacggcaat gtaccagctg atataatcag ttattgaaat atttctgaat ttaaacttgc    2880
```

```
atcaataaat ttatgttttt gcttggacta taatacctga cttgttattt tatcaataaa    2940
tatttaaact atatttcttt caagatatca ttctttacaa gtatacgtgt ttaaattgaa    3000
taccataaat ttttattttt caaatacatg taaaattatg aaatgggagt ggtggcgacc    3060
gagctcaagc acacttcaat tcctataacg gaccaaatcg caaaaattat aataacatat    3120
tatttcatcc tggattaaaa gaaagtcacc ggggattatt ttgtgacgcc gattacatac    3180
ggcgacaata aagacattgg aaatcgtagt acatattgga atacactgat tatattaatg    3240
atgaatacat actttaatat ccttacgtag gatcgatccg aattcgcgac acgcggccgc    3300
tctagaacta gtggatcccc cccttaatta agggggctgc aggaattcat aacttcgtat    3360
aatgtatgct atacgaagtt atagcttggt cgagtggaag ctagctttcc gatcctacct    3420
gtcacttcat caaaggaca gtagaaaagg aaggtggcac ctacaaatgc catcattgcg    3480
ataaggaaa ggctatcatt caagatgcct ctgccgacag tggtcccaaa gatggacccc    3540
cacccacgag gagcatcgtg gaaaagaag acgttccaac cacgtcttca aagcaagtgg    3600
attgatgtga tacttccact gacgtaaggg atgacgcaca atcccactat ccttcgcaag    3660
acccttcctc tatataagga agttcatttc atttggagag gacacgctga aatcaccagt    3720
ctctctctac aagatcgggg atctctagct agacgatcgt ttcgcatgat tgaacaagat    3780
ggattgcacg caggttctcc ggccgcttgg gtggagaggc tattcggcta tgactgggca    3840
caacagacaa tcggctgctc tgatgccgcc gtgttccggc tgtcagcgca ggggcgcccg    3900
gttcttttg tcaagaccga cctgtccggt gccctgaatg aactgcagga cgaggcagcg    3960
cggctatcgt ggctggccac gacgggcgtt ccttgcgcag ctgtgctcga cgttgtcact    4020
gaagcgggaa gggactggct gctattgggc gaagtgccgg ggcaggatct cctgtcatct    4080
caccttgctc ctgccgagaa agtatccatc atggctgatg caatgcggcg gctgcatacg    4140
cttgatccgg ctacctgccc attcgaccac caagcgaaac atcgcatcga gcgagcacgt    4200
actcggatgg aagccggtct tgtcgatcag gatgatctgg acgaagagca tcaggggctc    4260
gcgccagccg aactgttcgc caggctcaag gcgcgcatgc ccgacggcga ggatctcgtc    4320
gtgacgcatg gcgatgcctg cttgccgaat atcatggtgg aaaatggccg cttttctgga    4380
ttcatcgact gtggccggct gggtgtggcg gaccgctatc aggacatagc gttggctacc    4440
cgtgatattg ctgaagagct tggcggcgaa tgggctgacc gcttcctcgt gctttacggt    4500
atcgccgctc ccgattcgca gcgcatcgcc ttctatcgcc ttcttgacga gttcttctga    4560
gcgggactct ggggttcgat ccccaattcc cgatcgttca acatttggc aataaagttt    4620
cttaagattg aatcctgttg ccggtcttgc gatgattatc atataatttc tgttgaatta    4680
cgttaagcat gtaataatta acatgtaatg catgacgtta tttatgagat gggtttttat    4740
gattagagtc ccgcaattat acatttaata cgcgatagaa aacaaaatat agcgcgcaaa    4800
ctaggataaa ttatcgcgcg cggtgtcatc tatgttacta gatcggggat cgggccactc    4860
gaccaagcta taacttcgta taatgtatgc tatacgaagt tatcgcgcca aatcgtgaag    4920
tttctcatct aagccccat ttggacgtga atgtagacac gtcgaaataa agatttccga    4980
attagaataa tttgtttatt gctttcgcct ataaatacga cggatcgtaa tttgtcgttt    5040
tatcaaaatg tactttcatt ttataataac gctgcggaca tctacatttt tgaattgaaa    5100
aaaaattggt aattactctt tcttttctc catattgacc atcatactca ttgctgatcc    5160
atgtagattt cccggacatg aagccattta caattgaata tatcctgccg ccgctgccgc    5220
```

```
tttgcacccg gtggagcttg catgttggtt tctacgcaga actgagccgg ttaggcagat    5280
aatttccatt gagaactgag ccatgtgcac cttcccccca acacggtgag cgacggggca    5340
acggagtgat ccacatggga ctttt                                         5365
```